US 8,539,840 B2

(12) United States Patent
Ariessohn et al.

(10) Patent No.: US 8,539,840 B2
(45) Date of Patent: Sep. 24, 2013

(54) AEROSOL COLLECTION APPARATUS AND METHODS

(75) Inventors: Peter C Ariessohn, Lake Tapps, WA (US); Igor V Novosselov, Seattle, WA (US); Evan Dengler, Seattle, WA (US)

(73) Assignee: Enertechnix, Inc, Maple Valley, WA (US)

( * ) Notice: Subject to any disclaimer, the term of this patent is extended or adjusted under 35 U.S.C. 154(b) by 322 days.

(21) Appl. No.: 13/099,295

(22) Filed: May 2, 2011

(65) Prior Publication Data

US 2012/0174650 A1     Jul. 12, 2012

Related U.S. Application Data

(63) Continuation-in-part of application No. 12/364,672, filed on Feb. 3, 2009, now abandoned.

(60) Provisional application No. 61/026,376, filed on Feb. 5, 2008.

(51) Int. Cl.
    *G01N 3/02*     (2006.01)
(52) U.S. Cl.
    USPC .......................................................... 73/860
(58) Field of Classification Search
    None
    See application file for complete search history.

(56) References Cited

U.S. PATENT DOCUMENTS

| | | | |
|---|---|---|---|
| 3,901,798 A | 8/1975 | Peterson | |
| 4,321,822 A | 3/1982 | Marple | |
| 4,452,068 A | 6/1984 | Loo | |
| 4,670,135 A | 6/1987 | Marple | |
| 4,764,186 A | 8/1988 | Langer | |
| 4,767,524 A | 8/1988 | Yeh | |
| 4,827,779 A | 5/1989 | Marple | |
| 5,425,802 A | 6/1995 | Burton | |
| 5,469,061 A | 11/1995 | Linehan et al. | |
| 5,498,271 A | 3/1996 | Marple | |
| 5,533,406 A | 7/1996 | Geise | |
| 5,693,895 A | 12/1997 | Baxter | |
| 6,062,392 A | 5/2000 | Birmingham | |
| 6,082,185 A | 7/2000 | Saaski | |
| 6,087,183 A | 7/2000 | Zaromb | |
| 6,110,247 A | 8/2000 | Birmingham | |
| 6,170,342 B1 | 1/2001 | John | |

(Continued)

OTHER PUBLICATIONS

Weber et al, 2001. A particle-into-liquid collector for rapid measurement of aerosol bulk chemical composition. Aerosol Sci Tech. 35:718-727.

(Continued)

*Primary Examiner* — Peter J Macchiarolo
*Assistant Examiner* — Alex Devito
(74) *Attorney, Agent, or Firm* — K Karel Lambert; Lambert Patent Services LLC

(57) ABSTRACT

An apparatus or device for collecting aerosol particles from a gas stream, having a collector body enclosing a collector channel, a particle trap in the collector channel, and an injection duct for injecting a discrete microdroplet of an elution reagent. The particle trap may be a centrifugal impactor, a bluff body impactor, or an electrostatic impactor. Aerosol particles are deposited on the surface during collection and are subsequently eluted with a microdroplet or a series of microdroplets as a concentrated liquid sample so that the sample can be analyzed in situ or conveyed to a detector for analysis. The collector serves as an aerosol-to-liquid conversion module as part of an apparatus for detecting and analyzing aerosol particles, and may be used in an integrated environmental threat assessment system, for example for characterization of aerosolized chemical and biological weapons, or for industrial or environmental monitoring.

27 Claims, 40 Drawing Sheets

(56) References Cited

U.S. PATENT DOCUMENTS

| | | |
|---|---|---|
| 6,363,800 B1 | 4/2002 | Call |
| 6,435,043 B1 | 8/2002 | Ferguson |
| 6,506,345 B1 | 1/2003 | Lee et al. |
| 6,520,034 B1 | 2/2003 | Masquelier |
| 6,660,363 B1 | 12/2003 | Barthlott |
| 6,698,592 B2 | 3/2004 | Kennings |
| 6,732,569 B2 | 5/2004 | Ondov |
| 6,938,777 B2 | 9/2005 | Call |
| 7,201,879 B2 | 4/2007 | Hill |
| 7,261,008 B2 | 8/2007 | Saaski |
| 7,578,973 B2 | 8/2009 | Call |
| 7,704,294 B2 | 4/2010 | Ariessohn |
| 7,875,095 B2 | 1/2011 | Ariessohn |
| 7,909,910 B2 | 3/2011 | Benner |
| 2002/0098097 A1 | 7/2002 | Singh |
| 2004/0023411 A1 | 2/2004 | Fenn |
| 2004/0069047 A1 | 4/2004 | Coyle et al. |
| 2004/0232052 A1 | 11/2004 | Call |
| 2005/0214168 A1 | 9/2005 | Lin |
| 2006/0110818 A1 | 5/2006 | Hill |
| 2006/0171844 A1 | 8/2006 | Sioutas |
| 2008/0022853 A1 | 1/2008 | Ariessohn |
| 2009/0288475 A1 | 11/2009 | Ariessohn |
| 2010/0062415 A1 | 3/2010 | Schwoebel |

OTHER PUBLICATIONS

Orsini et al 2003. Refinements to the particle-into-liquid sampler for ground and airborne measurements of water soluble aerosol composition. Atmospheric Environ 37:1243-59.

Min, JY, authorized officer. 2009. International Search Report for PCT/US2009/033095, 3 pages, published Nov. 25, 2009 by WIPO as Intl Publ No. WO2009/134495A3R4.

Fair RB et al 2004. Integrated chemical:biochemical sample collection, pre-concentration, and analysis on a digital microfluidic lab-on-a-chip platform. Proc SPIE vol. 5591.

Gridin et al 1997. A renewable liquid droplet method for on-line pollution analysis by multi-photon ionization. Anal Chem 69:2098-2102.

Peng et al. (1995) Generating particle beams of controlled dimensions and divergence: II. Experimental evaluation of particle motion in aerodynamic lenses and nozzle expansions. Aerosol Sci Technol 22:293-313.

Loo BW et al. Dichotomous virtual impactors for large scale monitoring of airborne particulate matter, In (Byh Liu, ed) Fine Particles: Aerosol generation, measurement, sampling and analysis (1976) pp. 312-349.

$R_C = 0.5 \times ID$ $R_C = 0.66 \times ID$

PARTICLE COLLECTION EFFICIENCY vs FLOW RATE (2 mm CHANNEL)

COLLECTION CHANNEL DIAMETER vs VOLUME

| Diameter (mm) | Volume (uL) |
|---|---|
| 0.10 | 0.002 |
| 0.20 | 0.02 |
| 0.30 | 0.06 |
| 0.50 | 0.29 |
| 0.60 | 0.51 |
| 0.75 | 0.99 |
| 1.00 | 2.36 |
| 1.50 | 7.95 |
| 2.00 | 18.85 |

IMPROVED RECOVERY OF E coli B WITH (w/SSL) AND WITHOUT (w/o) SACRIFICIAL SUBSTRATE UNDERLAYER

*Fig. 23*

441 INTAKE

440a
AEROSOL CONCENTRATOR MODULE

BULK FLOW → 442

6 ↓

450a
AEROSOL COLLECTOR MODULE

→ 7

444a

30
LIQUID SAMPLE ANALYSIS MODULE
460a

**Detection of Aerosolized E. coli O157:H7
by Microdroplet Elution from Impactor
followed by RT-PCR in an Integrated Device**

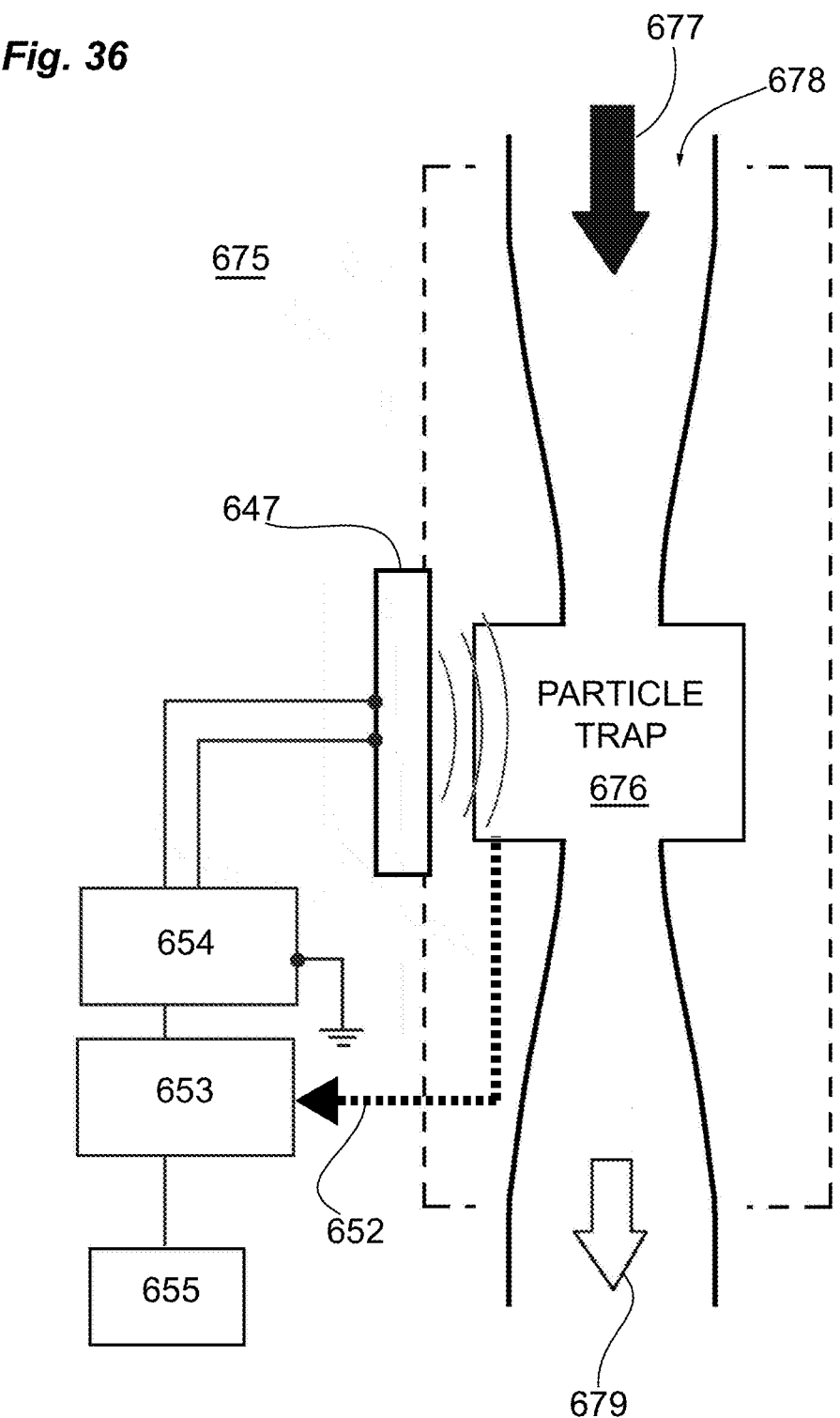

AEROSOL COLLECTION APPARATUS AND METHODS

RELATED APPLICATIONS

The present application is a Continuation-In-Part of U.S. patent application Ser. No. 12/364,672 titled "Aerosol Collection and Microdroplet Delivery for Analysis", filed 3 Feb. 2009, now abandoned, which claims the benefit of priority under 35 USC 119(e) Provisional Pat. Appl. No. 61/026,376 filed on 5 Feb. 2008, said patent documents being incorporated herein in entirety for all purposes by reference.

GOVERNMENT SUPPORT

The United States Government has rights in this invention pursuant to Grant No. NBCHC060109 awarded by the Department of Homeland Security, and Grant No. 1R43ES016390-01 awarded by the National Institutes of Health.

BACKGROUND

Aerosols from natural, anthropogenic and industrial sources have long been recognized as a potential threat to human health; to that list of sources we now must add airborne chemical or biological warfare agents as a source of potentially lethal exposure or terrorist threat. Effective sampling and collection of aerosol particles is a critical first step in the detection and identification of these hazards. Identification methods such as immunological or nucleic acid assays typically require the aerosol sample to be suspended in a liquid medium. There is therefore a need for a "front-end" device adapted to collect these aerosols and prepare or deliver them in a concentrated suspension or solution for analysis.

Higher concentration of aerosol particles in a liquid sample achieves greater sensitivity for many analyses. Today's micro analytical instruments require microliter or nanoliter sample volumes, and larger volumes of liquid are difficult to process. Moreover, currently available aerosol collectors cannot readily be adapted to perform sample preprocessing prior to analysis, a significant disadvantage for integrated sampling and detection platforms. Sample preprocessing includes processes such as dissolution of sample matrix, lysis of suspect cellular contents, or preliminary screening to trigger more exhaustive analysis, process steps which speed threat detection and avoid unnecessary analyses.

Current aerosol collection devices that provide liquid samples for analysis, such as wetted wall cyclones, wetted rotating vane impactors, and liquid impingers, are inefficient and produce large volume liquid samples, and are not well adapted to concentrating an aerosol. Large sample volumes are suitable for use with assays using 96- or 384-well plates, but the current trend is towards smaller scale, more-automated procedures using microfluidics, which demand much smaller sample volumes. Liquid impingers and wetted wall collectors of the prior art cannot simply be miniaturized because of the drying effects of evaporation during operation and the difficulty in holding in place a small volume of a liquid under a stream of high velocity gas.

For example, in US Pat. Appl. Doc. No. 2004/0232052 to Call, a "liquid jet" (see FIGS. 19 and 20A of US 2004/0232052) is applied so that samples are "blasted off the collection surface" (p. 22, para. 0238) into a sample container. Such a procedure can only result in losses of sample and increased dilution, and is likely not workable.

Thus there remains a need for a collector capable of efficiently concentrating an aerosol from a large volume of air into a few microliters or nanoliters of a liquid sample. In this regard, the field of microfluidics has revolutionized many aspects of chemistry and microbiology and is an enabling technology for the development of a wide range of detection and identification methods. Following the pioneering work of Wilding (U.S. Pat. Nos. 5,304,487, 5,376,252, 5,726,026, 5,955,029, 6,953,676), continuous and intermittent-flow microfluidic devices have been developed that carry out nucleic acid and immunological analyses in integrated devices fabricated on silicon or glass substrates. Digital microfluidic devices employ technologies such as electrowetting, diaelectrophoresis, or microhydraulics to move, mix, combine and split microliter and nanoliter volumes and allow chemical and biological assays to be automated and carried out at very small scales. These advances offer substantial advantages in speed and accuracy while greatly reducing the need for operator involvement and minimizing reagent volumes. However, the problem of developing an effective "front-end" interface for ambient aerosol particle concentration, collection, and delivery in a nano- or microvolume to "back-end" analytical instrumentation has not been addressed.

Aerosol pre-concentration, prior to sample collection, offers a significant advantage when coupled to an analytical method. Using a variety of devices known in the art as "virtual impactors", aerosol particles to be sampled from a larger volume of air are concentrated into a particle-enriched gas stream of smaller volume (the "minor flow" or "particle-enriched flow") while the bulk of the sampled air, depleted of particles, (also termed the "major flow", "bulk flow", or "particle-depleted flow") is discarded. Such an aerosol concentrating device is described in US Pat. Appl. Doc. No. 2008/0022853, entitled "Aerodynamic Lens Particle Separator", and is co-assigned to the Applicant. Other air-to-air concentrators include virtual impactors such as the US Army's XM2 virtual impactor, those described in U.S. Pat. Nos. 3,901,798, 4,670,135, 4,767,524, 5,425,802, 5,533,406 and 6,698,592, and others.

An aerosol-to-liquid collection and delivery system that accepts raw or concentrated aerosols and delivers resuspended or solubilized aerosol particles in small droplets of fluid will serve as the front end to a number of biochemical or physical detection platforms. Initial demand is expected to be primarily in the security, military, and biomedical fields, but also in environmental and industrial sampling and monitoring applications, and will be driven to smaller sample volumes by technological advances in the development and integration of detection platforms and assays, including and not limited to both in situ and downstream assays for particles and particle constituents.

However, particle traps become fouled with accreted deposits when overloaded in extended use and typically are protected by upstream filters that prevent entry of oversized materials such as dust, fibers, or aerosolized salt crystals which would otherwise block gas flow. Accumulation of micron- or submicron-sized particles can also result in blockage. As a result, these devices must be continuously monitored for performance, for example by monitoring backpressure and/or continuity of flow. This problem has adversely impacted the wider use of particle traps for a variety of industrial and security applications in favor of particle collection devices that rely on wetted wall or liquid impingement technology, both of which are comparatively less sensitive and less portable.

Similarly, "air-to-air aerosol concentrators" such as aerodynamic lenses and virtual impactors, which are frequently used to fractionate and concentrate particles in a gas flow prior to collection or detection, are also hampered by fouling considerations. For example, particle deposits can accumulate around the mouth of a virtual impactor, often termed a "skimmer", where the gas flow is split into a "minor flow" enriched in particles and a "major flow" (sometimes termed "bulk flow") depleted of particles. Particle accumulation on the surfaces of these devices, particularly on surfaces and in channels around the skimmer mouth, unacceptably alters device performance. These are not the intended particle collection surfaces, but nevertheless become progressively fouled. Unfortunately, deterioration of performance accelerates over time: i.e., as deposits become larger the fouling rate increases in a vicious cycle.

Removal of particle deposits can be technically difficult. The channels used in inertial impactors may be looped and have small dimensions. A mechanical arm such as a pipe cleaner inserted into the channel to clean the channel must be thin and flexible, and excess force in cleaning can result in formation of a packed mass that cannot be physically removed. Disassembly for cleaning, such as by removal of cathodic and anodic plates of an electrostatic precipitator, can be inconvenient or not possible. Aggressive chemical cleaning solutions can damage the smoothness of the channel surfaces. Also, aggressive cleaning methods will likely result in destruction of the structure and/or composition of the captive particles, defeating a basic purpose of particle collection and sampling for analysis, and hence are not satisfactory.

Call, in U.S. Pat. No. 6,938,777, describes a method for removing concentrated "spots" of deposited particles from an impactor surface, which involves first transporting the surface bearing the spot from the collection device, and then subjecting the spot to a blasting jet of fluid or using a mechanical scraper to dislodge the spot. In practice, the impactor surface is formed on a moveable solid support, for example in the form of a roll of tape or a rotating disk, so that the impactor surface can be translocated from the collection apparatus, and the method is thus not generally applicable. Where the internal surface cannot be removed from the aerosol collector, such as the internal surfaces of particle traps or virtual impactors or for sampling of particles entrapped within an enclosed particle trap, no solution is provided.

In U.S. Pat. No. 7,578,973, Call goes on to point out that particulate "wall loss," i.e. unintended deposition of particles on various surfaces of virtual impactor structures (especially the curved or bent portions) remains a challenging problem (Col 2, lines 24-36).

Thus, there is a need in the art for a method and apparatus to clean particle traps and aerosol concentrators such as virtual impactors, either in response to a change in gas flow associated with accumulation of particles therein, or periodically as prophylaxis against accumulation of particles. Preferably the method also facilitates particle sampling.

SUMMARY

This invention addresses problems associated with concentrating, collecting and microeluting captured aerosol particles, or their constituents, from particle traps in very small volumes and problems associated with operating aerosol concentrator, collector and monitoring equipment without deterioration of performance.

A first collector module of the invention is designed so that aerosol particles are collected in a particle trap, which may be an inertial impactor or an electrostatic precipitator, within a collector channel, and a microdroplet or series of microdroplets are then introduced so as to contact a correspondingly small surface of the particle trap. The elution microdroplet is closely confined within the collector channel, which may be of microfluidic or near-microfluidic dimensions. The aerosol particles deposited in the trap are eluted as a liquid suspension or solution in a discrete microdroplet volume. In another aspect of the invention, the sample material is reacted or treated in situ in preparation for analysis or analyzed in situ by physical, chemical, biochemical or molecular methods, "in situ" indicating that the reactions, treatment or analysis of the liquid sample are conducted in the particle trap.

Using these methods and apparatus, we have discovered that an impacted aerosol particle sample can be eluted from microfluidic-scale impactor surfaces in a constrained space with a very small droplet or a series of droplets of elution fluid, even nanoliter-sized droplets, enabling large concentration factors and increased sensitivity and robustness in detection of aerosol particles or their constituents of interest. The foremost technical advantage is the ability to achieve extremely high concentration factors and prepare the collected sample material for analysis in extremely small droplets in near real time.

Impaction on an impactor surface is an attractive method of capturing aerosol particles and aerosol particles from a concentrated particle stream at high velocity. The velocity of impaction may approach or exceed 50 m/s, depending on the desired particle size cut-off, and sample materials impacted at such velocities typically resist removal from the impactor. However, unless first eluted from the impactor surface, these adherent sample materials are not generally accessible for many kinds of analyses. Inability to elute the sample material in a liquid volume can result in failure to detect a bioaerosol, particulate toxin or other aerosol particle of interest. Surprisingly, "micro-elution" is successfully achieved by confining the elution fluid to a very small volume in contact with a correspondingly small impactor surface. This phenomenon is relevant to both inertial impactors and electrostatic precipitators.

The ability of these devices to collect large numbers of aerosol particles in a short time and deliver them in very small fluid volumes offers the possibility to greatly enhance the speed and sensitivity of existing detection methods. A method of this approach includes (i) directing a concentrated gas stream containing aerosol particles, typically received from a virtual impactor or other air-to-air concentrator, into an enclosed collector channel with small internal dimensions, (ii) impacting the aerosol particles in a particle trap within the collector channel, thereby reversibly adhering the particles to a small impactor surface, (iii) periodically eluting captured aerosol particles as a suspension or a solution from the surface in a liquid sample by injecting a discrete microdroplet volume or a series of microdroplet volumes of an elution reagent into the particle trap and contacting the liquid with the impactor surface, then (iv) optionally performing in-situ sample pretreatment of the collected particles, for example by mixing a reagent with the liquid sample, (v) optionally performing in-situ analysis of the sample by physical, chemical, biochemical, or molecular methods, or (vi), optionally conveying the liquid sample out of the collector channel to a sampling port. The microdroplet volume is a discrete volume, indicating that the fluid is not a continuous stream of flow. In one aspect, a discrete volume of ten microliters or less, more preferably 1000 nanoliters or less, is applied to the impactor surface. Impactor surfaces include centrifugal impactors, bluff body impactors, and electrostatic precipitators. Forces responsible for impaction of the particles include inertial forces and electrostatic forces.

At least one internal cross-sectional dimension of the collector channel proximate to the particle trap impactor surface may be less than 1500 micrometers, thereby confining the microdroplet in contact with the impactor surface. We demonstrate elution here using very small droplet volumes of a liquid reagent. Injection of precisely controlled discrete microvolumes of a reagent fluid into the particle trap can be achieved using ink-jet printing technology, for example.

Transporting or conveying the microdroplet through the collector channel can be accomplished in a variety of ways. These include "pump functionalities" as broadly encompassed herein. Applying a pressure differential, such as a suction pressure applied to the collector channel, is a simple approach. Pump functionalities include microfluidic diaphragm pumps, syringe pumps, piezoelectric pumps, inkjet printing pumps generally, positive displacement pumps, magnetostrictive diaphragm pumps, electrostatic pumps, thermopropulsive pumps, electrokinetic or electroosmotic pumps, and Gibbs-Marangoni pumps, such as are useful for applying a pumping force to a liquid sample in the collector channel, and may be mounted in or on the collector body or placed remotely in a larger apparatus of which the collector module is part. These technologies will be discussed further below.

In various embodiments of the invention, the collector module comprises an inertial impactor, including centrifugal impactors and bluff body impactors. Centrifugal impactors include "u-tubes" and concavoconvexedly curving channels in general. Bluff body impactors divert gas streamlines around an unstreamlined obstruction in the path of the gas stream. In other embodiments, the collector module comprises an electrostatic precipitators.

Also disclosed are integrated detection and identification modules wherein a sampling injector duct is connected at a first end to a "tee" in the collector channel or particle trap and at a second end to a microfluidic assay circuit for further processing and analysis. In one embodiment, the particle trap is an integrated component of a microfluidic analysis circuit. In other embodiments, the particle trap is fitted with an optical window, lightpipe, lens flat, or waveguide for in situ analysis of said discrete liquid sample. In certain embodiments, a sacrificial layer of a soluble substrate is applied to the surfaces of the particle trap before use, so that by dissolving the sacrificial layer in an elution reagent, any aerosol particles captured on the surface of the sacrificial layer are released into the elution reagent. In situ analysis may be for screening purposes, so that samples can be tagged for more in-depth analysis subsequently. Liquid samples collected as described herein may be archived for later use. Apparatus and methods are disclosed, including combinations of aerosol collector modules with aerosol collector modules and liquid sample analysis modules.

The invention addresses the problem of collecting aerosol particles from large volumes of air in very small particle traps, and eluting the captive sample material in very small volumes of a liquid reagent, thus achieving extremely high concentration factors relative to the dispersed aerosol and improving sensitivity and robustness of analyses of the captive aerosol particles and their constituents in an air-to-liquid aerosol concentrator and collector.

An unsolved problem in the field of aerosol analysis and aerosol hazard detection relates to aerosol monitoring equipment that has become blocked or fouled and must be replaced or rebuilt, which can result in down time of critical monitoring systems. We have found that acoustic cleaning "on the fly" removes buildup of particle deposits without the need to interrupt ongoing monitoring. Devices that benefit from acoustic cleaning in response to particle accumulation and fouling include aerosol concentrators, aerodynamic lenses, virtual impactors, inertial impactors, centrifugal impactors, bluff body impactors, and electrostatic precipitators.

Particles in a flowing gas stream are typically concentrated in a part of the gas stream and separated from the gas flow by impaction or precipitation onto a solid surface. During this process, some particles are inadvertently deposited on other internal surfaces of the equipment. The net effect of excessive accumulation of particles on internal surfaces is a deterioration of performance efficiency in capturing particles from the gas stream. Of interest here is the use of acoustic energy to excite the internal solid surface or surfaces of the aerosol monitoring equipment and thereby dislodge particle deposits for cleaning or sampling.

In a first embodiment, acoustic energy is applied to the internal solid surfaces while a gas flow is directed across the surfaces of interest. In this "dry" cleaning method, particles that are dislodged are entrained in the flowing gas and removed from the equipment. Deterioration in performance associated with accumulation of particles can be corrected in most instances. In the case of particles that cannot be cleared in this way, the gas flow direction may be reversed and dry application of acoustic energy repeated.

Surprisingly, periodic application of acoustic energy may also be used preventatively so that performance is not affected during extended use without interruption of monitoring. The benefits of "on the fly" prophylactic insonation treatments can be achieved with very low power consumption and without down time. Intermittent pulsatile application of acoustic energy can prevent fouling over an extended lifetime of use, for weeks or months, and in fact improves particle collection efficiency by routine intermittent application of dry acoustic treatments.

For those instances where particle deposits are resistant to routine dry acoustic treatment, acoustic cleaning may be augmented by injecting a liquid into the internal works. The liquid is contacted with the deposits and acoustic energy is applied to stimulate release of the deposits from the surface or surfaces. Aqueous or non-aqueous liquids and mixtures may be used, optionally in combination with surface active agents. If desired, a liquid-acoustic cleaning cycle may be applied periodically. This "wet" cleaning method requires interruption of the gas flow. However, we have found this disadvantage is offset by the synergy achieved in acoustically sampling accreted particles during a cleaning cycle, which when concentrated in small, discrete volumes of a liquid, are more readily subjected to analysis. The samples of liquid cleaning fluid can be assayed in situ for particles or particle constituents by optical or by radiological methods, or can be conveyed downstream for more complex analyses. Thus the particle monitoring or collection equipment may be configured as a gas-to-liquid concentrator by incorporation of acoustic transducers and a liquid injection capability.

Acoustic energy may be applied to a solid substrate directly, using contacting transducers, or indirectly, using non-contacting air-coupled transducers, and any particles dislodged into a liquid contacting the substrate may be sampled by collecting the liquid. Contacting and/or gas-coupled electro-acoustic transducers may be used, either one or the other, or together.

In a preferred embodiment, the initial cleaning event is a "dry cleaning" treatment, where the equipment is treated with acoustic energy without wetting; then if performance is not restored or residual particle buildup is not acceptable, a secondary "wet cleaning" treatment may be performed. This combination of steps is used to clean the equipment of any particle load that would interfere with subsequent detection events. In this way, a next particle sample can be collected without the need to replace the particle accretion surface, and without damage to the workings of the apparatus. This apparatus can be cycled through dry cleaning, wet cleaning, and wet sampling modes semi-continuously, or a wet cleaning cycle and sampling cycle can be triggered only in response to a signal. The apparatus is otherwise cleaned on the fly using dry ultrasound without interruption of gas flow, an advance in the art.

Where cleaning or sampling is triggered by a change in performance or particle loading, a buildup of particle mass on an internal surface of a particle collector or concentrator may be detected by a change in gas flow in the apparatus, such as a change in velocity or backpressure, or by monitoring a change in light transmittance, absorbance, or reflectance of an internal surface; and a positive signal output from a sensor or detector triggers the acoustic cleaning or sampling treatment. A particular constituent of a particle mass, such as a radioactive emission or a fluorescence may trigger a sampling cycle. If the particle mass is not of interest, it may be cleaned away using dry ultrasound so that the unwanted particle mass is discarded while continuing to monitor gas flow and collect or focus particles. If it is desired to capture a sample of an accumulated particle mass, a liquid is applied to a surface where particles have been deposited and an application of acoustic energy results in release of the captive particulate material into the liquid. The liquid may then be analyzed in situ, conveyed to a downstream analysis module of the apparatus, or exported and captured for remote analysis or archiving.

Any suitable signal can be used to trigger a cleaning cycle. In one embodiment, an ultrasonic flow velocity sensor is used, where increases in flow velocity are associated with stenotic buildup of particle deposits in a particle trap or around a collector channel. The sensor may be the acoustic transducer used to apply acoustic energy for cleaning. In yet another embodiment, a backpressure sensor or densitometer is monitored on the feed side of the inlet port, and increases in backpressure or density are associated with a downstream constriction or blockage. In another embodiment, transmitted, attenuated or reflected light, or fluorescent emissions, are used to monitor particle buildup on an internal surface. Various in situ means for monitoring constituents of particle deposits are known in the art.

Instead of having to replace or service aerosol monitoring and particle collection equipment that has become blocked or fouled, captive particles that are trapped on and fouling aerosol concentrator or collector surfaces may be periodically mobilized and removed by application of a brief pulse of acoustic energy, essentially eliminating the progressive deterioration of performance resulting from fouling as is commonly seen with equipment of this type—with only a very low increase in power consumption. In more severe cases of fouling, wet acoustic cleaning may also be used by supplying a liquid injection system in combination with an acoustic transducer. The hydraulics of this system can be adapted so that particle:liquid concentrates in smaller liquid volumes are conveniently sampled for downstream analysis. In combination, dry acoustic cleaning can be used to routinely clear and discard particulate material that is not of interest, but when the particulate material merits further analysis, as when the particulate material meets certain preliminary analysis characteristics, the wet cleaning cycle functions synergically as a gas-to-liquid particle concentrator, generating a concentrated sample in a discrete liquid volume for further study.

Thus in a first aspect, the invention relates to an aerosol monitoring or particle collection apparatus with an electro-acoustic transducer for on-the-fly dry cleaning of equipment having inside surfaces subject to particle impaction and fouling. These include air-to-air particle concentrators (such as aerodynamic lenses, virtual impactors, skimmers, inlet particle separators, or cyclones) and particle traps (such as inertial impactors, centrifugal impactors, vortex separators, barrier filters, or electrostatic collectors).

An aerosol monitoring or particle collection apparatus of the invention comprises a) an internal channel for conveying aerosol particles in a gas stream flow therethrough, said internal channel having an inlet, an outlet, and a particle accretion surface therein; b) a pressure source for driving said gas stream flow from said inlet to said outlet; and c) an electro-acoustic transducer operatively coupled to said particle accretion surface, said electro-acoustic transducer having a power supply and control circuitry for applying pulses of acoustic energy to said particle accretion surface, said pulses having an on/off pulse duration, repetition rate, duty cycle, amplitude or frequency.

Generally, the electro-acoustic transducer is operatively coupled to the particle accretion surface through a solid body enclosing the internal channel, and the electro-acoustic transducer is a piezoelectric, magnetostrictive, or capacitive electro-acoustic transducer. Optionally the body of the device includes an acoustic waveguide for directing said acoustic energy to the particle accretion surface. However, air coupling may also be used.

Transducers may be ultrasonic or sonic. The acoustic pulses may be modulated, having bandwidth, resonance, harmonics, and soft start characteristics selected for extending the service life of the apparatus for sampling particle deposits. Carrier frequencies may also be used to improve penetration or to carry sensor information in reflective or time of flight sensing systems.

Using control circuitry and sensors, feedback control loops are realized. The on/off pulse duration, repetition rate, duty cycle, amplitude, frequency or other characteristics of the acoustic pulse may be adjusted in response to a change in the gas stream flow or upon direct detection of particle accumulation on a surface. Where the change in flow is associated with fouling, and where the change in flow is measured by a sensor operatively connected to the control circuitry, sensor feedback is used to adjust insonation on the fly. Similarly, where accretion of particles on the particle accretion surface is detected by a sensor operatively connected to the control circuitry, sensor feedback may be used to adjust insonation on the fly.

In a second aspect, the apparatus is also supplied with a hydraulic system for liquid injection and wet acoustic cleaning or sampling. An aerosol monitoring or particle collection apparatus having a wet cleaning mode generally includes a) a sensor operatively disposed to monitor the internal channel for accretion of particles on the particle accretion surface, and for emitting a signal indicative of particle fouling, b) a pneumatic control system under control of control circuitry for interrupting the gas stream flow in response to the signal; and c) a liquid hydraulic system controlled by said control circuitry, wherein said liquid hydraulic system is configured for injecting a discrete liquid volume onto said particle accretion surface and insonating said wetted particle accretion surface in response to said signal. The hydraulic system is supplied with means for removing particle deposits suspended or dissolved by the acoustic pulses in said insonated liquid volume.

While unwanted particle suspensions can be blown out of the apparatus in the gas stream, analysis of particles or particle constituents from time to time is also contemplated. Advantageously, in a third aspect, termed here "wet sampling mode", hydraulic sampling subsystems of the invention are adapted for sampling particle constituents that are suspended or dissolved by insonation in the presence of an injected liquid volume, where the hydraulic sampling subsystem is provided with a pump functionality and ducting for withdrawing a liquid sample of the particle mass and for fluidly conveying the liquid sample for downstream collection, archiving or analysis.

In another aspect, a sensor can be used in situ to detect a target constituent of interest in deposits in a particle trap and the wet sampling mode can be actuated in response to the signal.

Control circuitry is provided in the invention, and may be configured for operating in a dry cleaning mode, a wet cleaning mode, and a wet sampling mode, where the dry cleaning mode involves actuation of said electro-acoustic transducer without liquid injection, the wet cleaning mode involves actuation of said electro-acoustic transducer with liquid injection, and the wet sampling mode involves actuation of said electro-acoustic transducer with liquid injection and liquid sample withdrawal. Functionalities for dry and wet acoustic cleaning cycles may be combined in a single apparatus by providing for the appropriate analog actuators, including any valving, pumps, fluid reservoirs and so forth. Optionally, a wet cleaning mode can be combined with a wet sampling mode. Or wet sampling mode can be combined with dry cleaning mode. The capacity to flexibly maintain, clean, and sample particles from particle collection equipment without interruption or disassembly is an advance in the art.

In one embodiment, dry cleaning is performed regularly at intervals as experience demonstrates are sufficient to prevent particle build-up. In yet another aspect, the invention incorporates a sensor or sensors and control circuitry to trigger dry and/or wet acoustic cleaning in a feedback loop where operating parameters are continuously sensed and cleaning is performed to maintain or restore optimal efficiency: first by dry acoustic cleaning without interruption of gas flow, then if desired by wet acoustic cleaning to remove more stubborn deposits, or to obtain a liquid sample. Wet sampling may be initiated in response to an accumulation of a particle mass or by detection of a target particle constituent, for example by spectroscopic or fluoroscopic characterization of the particle mass in situ in the particle trap prior to sampling. In this way, unnecessary down time and exhaustion of time or resources on uninteresting or information-poor samples are avoided.

BRIEF DESCRIPTION OF THE FIGURES

FIG. 23 shows how modular construction with a collector body of the invention can be used to build an aerosol analytic apparatus integrating various combinations of modules.

FIG. 25 shows how modular construction with a collector body of the invention can be used to build an aerosol analytic apparatus integrating an electrostatic particle trap.

FIG. 27 is typical data showing nucleic acid amplification by PCR with real time detection by molecular beacon technology as applied to detection of an aerosol particle in a microfluidic cartridge having an integrated particle trap collector and associated microfluidic circuitry for PCR amplification of a nucleic acid.

FIG. 36 shows schematically a particle trap with electro-acoustic transducer element and driving circuitry coupled to a lateral face of a particle trap assembly.

Figure 1:
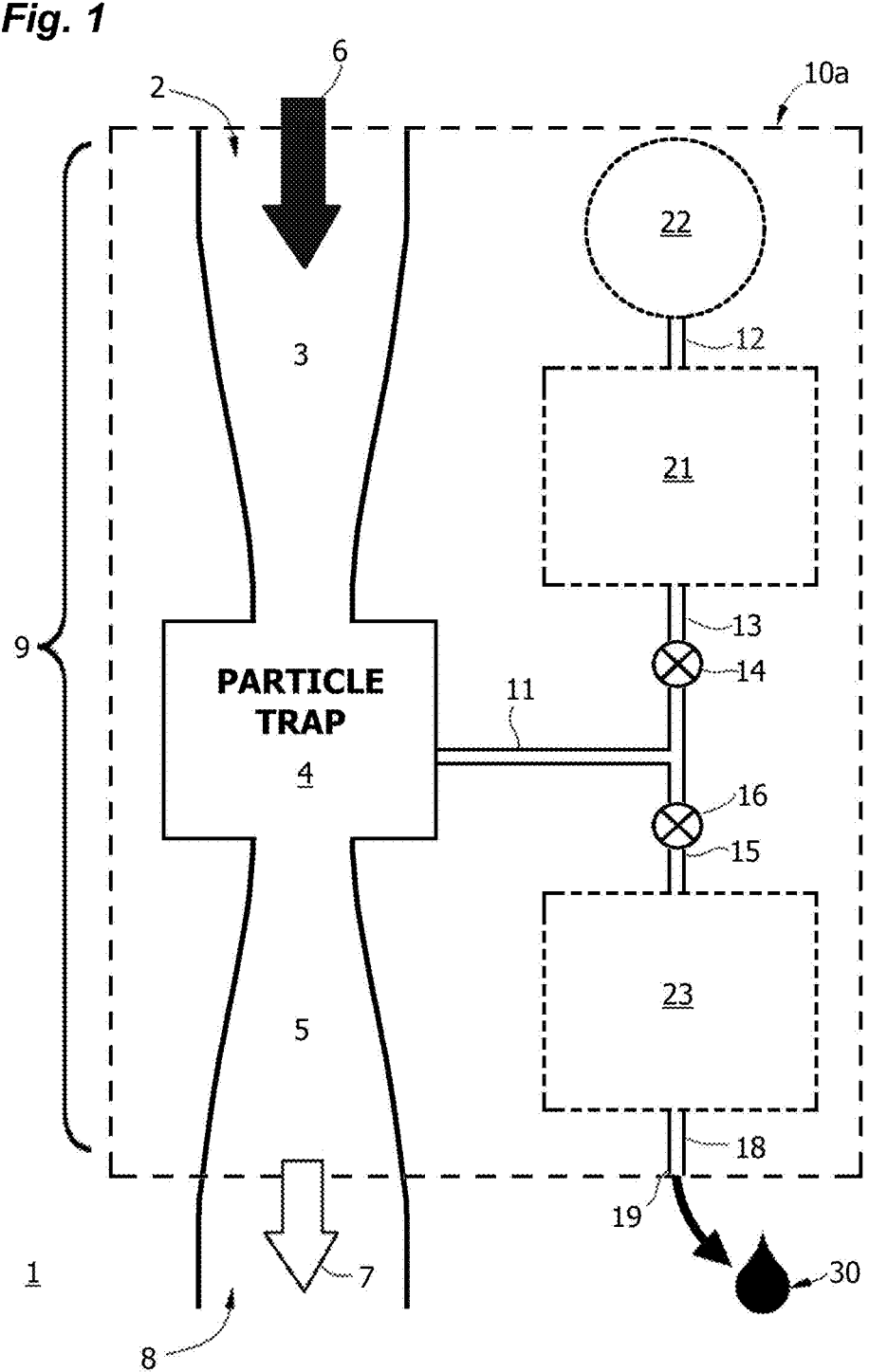
FIG. 1 is a schematic of a first collector module with particle trap.

The drawing figures are not necessarily to scale. Certain elements, features, steps or components herein are shown in somewhat schematic form and some details familiar to those skilled in the art might not be shown in the interest of clarity and conciseness.

DETAILED DESCRIPTION

Throughout the following description and claims, certain terms are used to refer to particular elements, features, steps or components and are defined here as intended by the inventors, i.e. they are intrinsic meanings. As one skilled in the art will appreciate, different persons may refer to the same element, feature, step or component by different names. This document does not intend to distinguish between elements, features, steps or components that differ in name but not in function, action or result. Other words and phrases used here take their meaning as consistent with usage as would be apparent to one skilled in the art.

Definitions

An "aerosol particle" is a generally diminutive or lightweight body of solid, liquid or gel-like matter suspended or dispersed in a gas volume. This can include, without limitation thereto, dust motes, exfoliated skin cells, fibers, spores, vegetative cells, mists, condensates, virus particles, bacteria, yeasts, mucous droplets, microdroplets of saliva and bronchial secretions, pollen grains, fly ash, smog condensate, smoke, fumes, dirt, fogs (as in industrial or agricultural spray application), salt, silicates, metallic particulate toxins, tar, combustion derived nanoparticles, particulate toxins, and the like. The aerosol particle may be a composite, containing both solid and liquid matter. Such particulate bodies can remain suspended in a column of air for long periods of time, can be carried on currents in the air, or can settle onto surfaces from which they may be resuspended by agitation.

Aerosol particles ranging from 0.01 to 25 microns are particularly hazardous. Particles less than 10 microns in apparent aerodynamic diameter pose a respiratory threat, and those less than 2.5 microns are of particular concern, as these can be inhaled deep into the lung. Aerosols include bioaerosols and particulate toxins.

"Aerosol"—refers to a population of small or lightweight bodies termed "aerosol particles" suspended or dispersed in a gas volume. An aerosol is composed of both a gas and a suspended or dispersed solid phase; the solid phase material is sometimes referred to herein as either an aerosol or as an aerosol particle, as will be apparent to be one skilled in the art.

Aerodynamic Diameter—is defined as the diameter of a sphere of unit density (1 g/cm$^3$) that attains the same terminal settling velocity ($v_s$) at a low Reynolds number as the actual particle under consideration. For mathematical modeling purposes, it is convenient to express the behavior of an irregularly shaped particulate specimen as if it were a spherical particle, making it easier to predict, compare and correlate various materials. Typically, the density of a particulate sample is not known during field sampling and calculations are generally performed assuming unit particle density (1 g/cm$^3$).

"Cut size"—The cut size parameter of an inertial impactor, $D_p^{50}$, is defined as the aerodynamic particle diameter at which 50% of the particles entering the impactor are captured on an internal impactor surface. The cut size particle size of a virtual impactor, $Dp^{50}$, is defined as the aerodynamic particle diameter at which 50% of the particles entering the virtual impactor follow the minor flow stream. Similarly, a $D_p^{100}$ would refer to a 100% cutoff.

The behavior of the impactor requires consideration of the Stokes number (Stk), which is the ratio of the particle stopping distance at a mean throat velocity to the throat width, and the Reynolds number (Re) since they govern particle and gas phase flow behavior, respectfully, in the impactor or virtual impactor. Taking $$Stk_{Lc} = \frac{[\rho_p \cdot D_p^2 \cdot C_c \cdot U_o]}{[18 \cdot \mu_f \cdot L_c]}, \text{ and}$$

$$Re_{Lc} = [\rho_f \cdot U_o \cdot L_c]/[\mu_f]$$

where:
$D_p$=particle diameter
$\rho_p$=particle density
$\rho_f$=fluid density
$C_c$=slip correction factor
$U_o$=mean velocity at critical dimension
$\mu_f$=fluid kinematic viscosity
$L_c$=critical throat or slit dimension,
and Re is a Reynold's number for a throat having dimension $L_c$.

Stk is the ratio of the particle stopping distance at a mean throat velocity to the throat or slit width and governs the collection efficiency in impactor theory. The stopping distance is defined as the maximum distance a particle can travel with an initial velocity in still air without any external forces. For Stk>>1, particles should follow a straight line as the gas turns and for Stk<<1, particles should follow the gas streamlines. These operating parameters are degraded by the accumulation of particulate material in the orifices and channels of the aerosol monitoring, concentration, or collection equipment.

"Critical dimension"—by example, a critical dimension ($L_c$) is associated with proximate fouling conditions include the throat or slit of a virtual impactor (where the width or diameter is a critical dimension) and the most narrow dimension of a centrifugal impactor (where the concavoconvexedly bending tube or slit has a critical diameter or depth proximate to the impactor surface). Also critical dimensions are inside clearances between opposing aerodynamic lens elements, entrances to chimney passages, and constrictions in collector manifolds, internal dimensions where fouling is most detrimental to performance.

"Aerosol concentrator module"—includes aerodynamic lens concentrators, aerodynamic lens array concentrators, and micro-aerodynamic lens array concentrators, when used in conjunction with a virtual impactor, skimmer or other means for separating a gas flow into a particle-enriched core flow (also termed "minor flow") and a "bulk flow", which is generally discarded. Also included are cyclone separators, ultrasound concentrators, and air-to-air concentrators generally for generating a flow split, where the "flow split" refers to the ratio of the minor flow to the bulk flow or total flow. The particle-enriched gas stream is delivered to an outlet of the aerosol concentrator module and may be conveyed to an aerosol collector module.

"Aerodynamic lens" (ADL)—is a device having a passage for a gas stream characterized by constrictions (lenses) that have the effect of focusing the particle content of the gas into a core flow region or "particle beam" surrounded by a sheath of particle depleted air. An ADL can further be configured with a virtual impactor (also termed a "skimmer") for separating the particle-enriched core flow (also termed "minor flow") from the sheath flow (commonly termed "bulk flow") which is generally discarded.

"Virtual impactor"—is an air-to-air aerosol concentrator which separates a particle fraction of an aerosol having a higher inertia from a surrounding air mass having a lower inertia, thereby concentrating the particle fraction in a smaller fraction of the gas. In operation, particles in the gas stream are first focused into a particle-rich core flow surrounded by a particle-poor sheath flow. The gas stream is then directed at an obstructing surface, where the obstructing surface includes a smaller orifice at the precise point where the particle rich core flow is targeted to impact the surface, and thus the "particle beam" or "particle ribbon" is admitted through the orifice without impact while the sheath flow is diverted by the obstruction on a new vector away from the core flow. The bulk of the gas stream (sometimes termed the "major flow") is diverted by the obstruction while a smaller fraction of the gas stream (typically termed the "minor flow") containing the particle is admitted through the orifice. Heavier or denser particles exceeding a "cut size" fail to change direction and pass through the virtual impactor mouth. Finer particles remain entrained in the deflected major flow. Particulate "wall loss," i.e., unintended deposition of particles on various surfaces of virtual impactor structures, especially at curved or bent portions and around the mouth of the virtual impactor, remains an unsolved problem because this unwanted particle deposition leads to fouling. Examples of virtual impactors and virtual impactor arrays include U.S. Pat. Nos. 3,901,798; 4,670,135; 4,767,524; 5,425,802; 5,498,271; 5,533,406; 6,062,392 and 7,875,095. ADLs and virtual impactors are described in U.S. Pat. No. 7,704,294 and in U.S. patent application Ser. Nos. 12/964,700 and 13/069618, which are co-assigned.

"Skimmer"—a virtual impactor device for separating a bulk flow from a particle-enriched core flow, generally used in conjunction with an aerodynamic lens to form an aerosol concentrator.

"Particle trap"—as used here, refers to a surface of a collector channel (a particle accretion surface) having the property of reversibly capturing aerosol particles by virtue of their size, inertia or electrostatic charge. Particles are captured by inertial inpaction or electrostatic precipitation, or by filtration on an internal surface or surfaces of the particle trap. Examples of particle traps and particle trap arrays include U.S. patent application Ser. Nos. 12/364,672, 12/833,665 and 13/069,618, which are co-assigned.

"Inertial Impactor"—a particle collector with a body or member having an impactor surface (a particle accretion surface) which is disposed in a gas flow such that streamlines of the gas flow are deflected around the impactor surface but particles with inertia exceeding the cut size of the device collide with the impactor and are captured on it. Inertial impactors of interest here include two classes, "centrifugal impactors" and "bluff body impactors". "Plate impactors" are considered here as a sub-class of bluff body impactors.

"Centrifugal Impactor"—describes a family of particle collectors in which an internal channel or throat for conducting the gas flow is bent or curves. Where the concavedly curving inner wall intersects or impinges on the long axis of gas flow, inertial force will cause more dense aerosol particles to impact what is termed here an "inertial impactor surface" or "centrifugal impactor surface" (i.e., a particle accretion surface), the area of the inside wall surface crossing or impinging on the long axis of flow. In a collector channel, an impactor surface is formed wherever an internal wall of the concavoconvex passage intersects or impinges the long axis of gas flow, deflecting the gas streamlines. The channel geometry for an inertial impactor is generally of tubular geometry (with circular, ovoid, or rectangular cross-section, and may be tapered or complex as described in U.S. Pat. No. 7,704,294 and in U.S. patent application Ser. Nos. 12/364,672 and 12/833,665. More broadly, centrifugal impactors may also include vortex particle collectors.

"Bluff Body Impactor"—Inertial impactors are also formed by flowing a gas stream around an obstacle in the path of the stream so as to cause a sharp change in the direction of the gas stream. In some cases, the gas flow is "split" around the obstacle. The obstacle, which is termed a bluff body, is not streamlined. The bluff body may be for example a pillar or a plate positioned to intersect the gas stream. Higher momentum particles do not deviate with the gas stream around the bluff body and instead collide with the windward surface of the obstacle, termed here an "inertial impactor surface" or "particle accretion surface".

"Electrostatic Precipitator"—refers to a particle collector having a pair of capacitively electrified plates for capturing charged aerosol particles on the plates. The plates are thus particle precipitators. Positive and negatively charged plate surfaces attract and bind oppositely charged particles. Particles may be natively charged or may acquire charge by contact with a source of ions, such sources including but not limited to a "corona wire," a source of ionizing radiation, or a radio-frequency discharge. Surfaces accumulating particles during operation are termed "particle accretion surfaces."

"Particle accretion surface"—an inside surface of a particle concentrator, collector or monitor which is sensitive to fouling by accumulated particles. The inside surface is generally not readily accessible for cleaning without disassembly of the aerosol monitoring, concentration, or collection apparatus.

"Aerosol Collector Module"—refers to an apparatus or subassembly of an apparatus for collecting and eluting captured aerosol particles or constituents thereof in a liquid volume. Aerosol collector modules may contain inertial impactors, centrifugal impactors, liquid impingers, bluff body impactors, or electrostatic precipitators. Fluidic systems are provided for microelution of the captured material as a liquid sample. The aerosol collector module is thus an "air-to-liquid" converter. Combinations of aerosol concentrator modules and aerosol collector modules are also "air-to-liquid" converters, having greater concentrative power than aerosol collector modules alone.

Inelastic collision—a collision with an impactor surface in which the colliding particle retains no kinetic energy after the collision, ie., the particle is captured on the impactor surface. Inelastic collisions may be irreversible or reversible.

Radius of curvature—($R_c$) or "bending radius" as defined here is taken along the centerline of a centrifugal inertial impactor and is generally in the range of greater than 0.5 to about three or ten times the characteristic dimension of the collector tube or channel. A radius of curvature of 0.5×ID, where ID is the "characteristic dimension" (height or internal diameter) of the channel, is not generally possible because the septum separating the arms of the channel at the bend would have no thickness. See also FIGS. 5B and 5C.

Elution—the meaning taken here is from the Latin verb root "luere, to wash out", and refers to a process in which a fluid is used to remove a substance from a location on which it is deposited—and to suspend, or solubilize, the concentrated substance in a liquid sample for analysis. To state that "the aerosol was eluted," indicates that an aerosol deposited in a particle trap was then taken up as a concentrate in a volume of a fluid for analysis. Broadly, as used herein, elution can also refer to the related process of leaching, where a component of a deposited material is solubilized to form a liquid sample. Elution may be enhanced by in situ insonation with a volume of a liquid. We may refer to "micro-elution" to indicate that elution takes place preferably in a "microvolume" of a liquid.

Pump functionality—or member, refers to any utility for pumping a fluid, such as are commonly known in the art.

Microfluidic—by convention, an adjective referring to apertures, channels, chambers, valves, pumps, and other hydraulic components having a cross-sectional dimension of less than 500 microns. Here microfluidic and near-microfluidic features are taken as inclusive of features with a dimension less than 2 mm, more preferably less than 1 mm, or less than 500 micrometers, where changes in flow behavior of liquids becomes obvious.

Microdroplet volume—refers to a discrete volume of a fluid, generally of 10,000 nanoliters or less. May also be termed a "microdroplet", although such volumes are not limited to volumes in the form of free-falling "droplets" per se and are frequently confined in a channel or contacted with a surface.

Nanodroplet—refers to a discrete volume of a fluid, generally of 1000 nanoliters or less, more preferably a few hundred nanoliters. May also be termed a "nanodroplet volume", although such volumes are not limited to volumes in the form of free-falling "droplets" per se and are frequently confined in a channel or contacted on a surface.

The prefix "micro-" generally refers to any component having a sub-millimeter-sized feature and any volume measured in microliters.

The prefix "nano-" generally refers to any component having a sub-micrometer-sized feature and any volume measured in nanoliters.

Glass—a wholly or partially amorphous solid having a glass transition temperature $T_g$: the temperature at which an amorphous solid, such as glass or a polymer, becomes brittle on cooling or soft on heating, and a melt temperature $T_m$. Below the glass transition temperature, $T_g$, amorphous solids are in a rigid glassy state and most of their joining bonds are intact. In organic molecules, particularly polymers, secondary, non-covalent bonds between the polymer chains become weak above $T_g$. Above $T_g$ glasses and organic polymers become soft and capable of plastic deformation without fracture. Above $T_m$, the solid becomes a liquid. Preferred here are glasses that have a solubility in a liquid.

Means for amplifying—includes the "polymerase chain reaction" (PCR) which is described in detail in U.S. Pat. Nos. 4,683,195, 4,683,202 and 4,800,159; in Ausubel et al. Current Protocols in Molecular Biology, John Wiley and Sons, Baltimore, Md. (1989), and in Innis et al., ("PCR Protocols", Academic Press, Inc., San Diego Calif., 1990). Polymerase chain reaction methodologies for nucleic acid amplification require thermocycling and are well known in the art. As means for amplifying also considered are isothermal amplification methods. By adding fluorescent intercalating agents, molecular beacons, and so forth, nucleic acid amplification products, known in the art as "amplicons", can be detected as reaction endpoints or in real time.

Liquid sample analysis module—refers to an apparatus or subassembly of an apparatus having means for detecting an aerosol particle or constituent of an aerosol particle, and having the purpose of detection and/or characterization of the particle or constituent thereof.

Means for detecting—as used herein, as used herein, refers to one or more functionalities for detecting, analyzing and/or characterizing a particle, a particle constituent, or a mass of particles as are generally well known in the art. Means for analyzing may include a) means for performing a liquid chromatographic step; b) means for performing a gas chromatographic step; c) means for performing an affinity binding step; d) means for performing an ionization step; e) means for performing an electrophoretic step; f) means for performing a spectrometric, fluorometric, or photometric step; g) means for performing a mass spectroscopic step; h) a means for performing an electrometric step; i) means for in situ detection; j) a combination of one or more of the above means; or k) other analysis and detection means known in the art. Analytical means can involve visual detection, machine detection, manual detection or automated detection.

"Acoustics" is an interdisciplinary science that deals with the study of sound, ultrasound and infrasound, more generally "sonics". Acoustic waves propagate in solids, fluids or gases as waves or disturbances in the ambient pressure level, and consist of alternating waves of compression and rarefaction. The periodicity of the waves may lead to resonance.

"Acoustic energy" is associated with the amplitude and the frequency of the waves or wave pulses. "Acoustic cleaning" as used here refers to the use of acoustic energy (i.e., "insonation") to clean an inside surface of aerosol monitoring, concentration, or collection equipment.

Acoustic waves carry energy. Carrier waves having a frequency of 2 to 15 KHz may be used where human hearing is not an issue. "Ultrasound", sound above the range detected by the human ear, is defined as having a frequency of greater than about 15-20 KHz, but for practical purposes is generally practiced in the 20 KHz to 20 MHz range. Acoustic waveforms may be continuous or intermittent.

"Electro-acoustic transducer"—a device for conversion of electrical to acoustic energy or vice versa. These transducers may be used to generate a waveform for carrying acoustic energy, generally by consumption of electricity. A first class of electro-acoustic transducers are formed of a piezoelectric material such as lead zirconate titanate (PZT), barium titanate or a polymeric materials such as polyvinylidene fluoride (PVDF). Another class of electro-acoustic transducers may be formed of magnetostrictive materials such as domain-microstructured materials containing terbium, dysprosium, or gallium in a nickel or ferrite crystalline base. Capacitive electro-acoustic transducers (ultrasonic transducers of this variety are termed "CUTs") are also known and are used for non-contact inspection. These devices are composed of a thin pliant membrane film and a rigid conducting backplate to form an electrostatic capacitor. Cyclically applied voltages cause the membrane to vibrate, and hence can generate ultrasound, whereas a change in voltage across the membrane can be used for detection. Metallic or ceramic backplates can be used; the backplate may be machined to improve the acoustic properties of the transducer. The ultrasonic emission may be collimated or focused to a point as desired, for example as described in US Pat. Appl. Doc. No. 2009/0158851. Microfabricated, layered structures having a resonant cavity or cell formed between a thin metallized membrane and a backplate electrode may be formed, the cell having a charged state and a relaxed state and the membrane capable of rapid flexion in the manner of a diaphragm (U.S. Pat. No. 5,287,331).

PZT transducers also may be coupled in air by applying a quarter-wavelength thick impedance matching layer to the front surface, but with loss of bandwidth and with generally poorer efficiency.

Hybrid cells in which the conductive membrane is driven simultaneously in both piezoelectric and electrostatic modes are known, as are resonant cavities having varied depth to achieve broader operating bandwidths (U.S. Pat. No. 6,775,388). Electro-acoustic transducers may be formed as rectilinear slabs, as arrays of elements, as annular arrays, as cylinders, as coin-like disks, as membranes, and so forth. In one class, concavedly spherical transducers are formed having the property of emitting focused acoustic waves, so that energy density of the propagated wave increases to a peak at a point away from the surface of the transducer.

Acoustic waves can be amplitude modulated or frequency modulated. A frequency sweep within the transducer's harmonic bandwidth is particularly useful in mobilizing particles from surfaces. Arrays of transducers having different bandwidths may be used to increase the frequency range.

"Ultrasound"—generally is defined as an acoustic wave having a frequency of greater than about 15-20 KHz, but may usefully extend into the megahertz range, up to perhaps 20 MHz. Ultrasound is a form of energy consisting of alternating waves of compression and rarefaction.

"Couplant"—a medium for transmitting ("coupling") a sound wave from a transducer to a solid surface, often a gel or a liquid.

"Conventional"—refers to a term or method designating that which is known and commonly understood in the technology to which this invention relates.

Unless the context requires otherwise, throughout the specification and claims which follow, the word "comprise" and variations thereof, such as, "comprises" and "comprising" are to be construed in an open, inclusive sense—that is as "including, but not limited to".

The appended claims are not to be interpreted as including means-plus-function limitations, unless such a limitation is explicitly recited in a given claim using the phrase "means for."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Collector Module for Micro-Elution of Captured Aerosol Particles

Turning now to the figures, FIG. 1 is a generic schematic of a collector module 10a for micro-elution of captured aerosol particles. Shown in block form are the functional components of a first embodiment of a particle collection and elution apparatus 1. A particle trap (block 4) is disposed in a collector channel 9, the collector channel, represented here figuratively, consisting of a receiving arm 3 with intake orifice 2 and an outlet arm 5 with outlet orifice 8. A gas stream 6 with aerosol particles enters the collector channel through the intake orifice and transits the particle trap 4. The particle trap may be an inertial impactor, such as a centrifugal inertial impactor or a bluff body impactor, or may be an electrostatic precipitator. The gas stream 7, depleted of particles, exits the collector channel 9 at the base of the module through outlet orifice 8. Aerosol particles accumulate as a mass or sample in the particle trap.

The elution apparatus of module 10a comprises a pump functionality or member (block 21) with associated fluid reservoir 22. The functional components of apparatus 1 with dashed outlines may be mounted within module 10a or may optionally be mounted externally and associated through fluidic connections with module 10a. Fluid from reservoir 22 is injected via microfluidic ducts 13 and 11, optionally with valve 14, into particle trap 4, in the form of a discrete microdroplet volume. Microfluidic duct 11 is termed a microfluidic injection duct. Generally the volume injected is small, and may be less than 10,000 nanoliters, more preferably less than 1000 nanoliters. In the particle trap, the microdroplet volume is contacted with the impactor surface or surfaces of the trap and captive aerosol sample is eluted in the confined structure of the particle trap 4, thereby forming a liquid sample.

The reagent fluid reservoir 22 may be contained in the collector module, or may be in fluidic communication with the injection duct 11 and pump functionality or member 21 but mounted externally.

Reagent fluids include elution reagents, analytical pre-processing reagents, and detection reagents. Elution reagents are formulated to resuspend and solubilize the captured aerosol particle mass. These reagents are generally aqueous, but may include co-solvents such as dimethylsulfoxide, N,N-dimethylformamide, N-methyl-pyrrolidinone, 2-pyrrolidone, acetone, diethylene glycol monoethyl ether, acetonitrile, acetone, methylethylketone, methyl tert-butyl ether (MBTE), tetrahydrofuran, and so forth. The co-solvent is generally miscible with water but if not may be formulated as an emulsion or microemulsion or used without water. Surfactants and wetting agents as are generally known in the art are also suitable for formulation in an elution reagent. Such surfactants may include Tween 20, Brij-72, Triton X100, Pluronic F68 (BASF, Florham Pk, N.J.), n-acyl-glutamate (Amisoft®, Ajinomoto, JP), Envirogem® 360 (Air Products, Allentown Pa.), Eccoterge® AEP-20 (Eastern Color, Providence R.I.), sodium lauryl sulfate, and so forth. A more comprehensive list of surfactants, co-surfactants and wetting agents may be found in McCutcheon's Emulsifiers and Detergents (2008 Edition). Also useful for eluting biological samples are salts and buffers. Analytical pre-processing reagents include for example chaotropic salts or urea, such as described by Boom (U.S. Pat. No. 5,234,809), or alkaline SDS lysis solution containing 200 mM NaOH and 1% SDS, as are known to aid in the lysis of bacterial cells, and also enzymes such as lysozyme, chitinase or mucopolysaccharidases. These reagents serve to prepare the sample in situ for analysis and to release any bioaerosol material from a sample matrix. Detection reagents include antibodies, probes in general, nucleic acid intercalating agents, chromogenic reactants, dyes, hydrogen peroxide for detection of catalase, NADH or NADPH for the detection of dehydrogenases, ATPases, pyrophosphatases, and so forth.

Reagents can be injected into the device in sequence, for example an elution reagent can be injected first, followed by an analytical pre-processing reagent, followed by a detection reagent, or other permutations as are effective in achieving the desired result. In some cases, one reagent serves multiple functions. In some instances, a dry reagent can be placed in the collector channel or particle trap prior to collection of a sample, having the purpose of later being rehydrated by contact with a liquid reagent so as to react with the aerosol sample or a constituent of the sample. While not limiting thereto, dry reagents include a hydrolytic enzyme such as lysozyme or chitinase for digesting a sample, a chromogenic or fluorogenic dye such as ethidium bromide or tetrazolium blue for staining a sample, or an antibody with fluorescent probe conjugate, for example.

Microelution of aerosol particles by dispensing an elution reagent onto the impactor surfaces as provided in the present invention is achieved by any of several species of small pumps or pump functionalities which can deliver fluids through microfluidic channels at very low volumetric flow rates and useful linear velocities. These micro-pumps include piezoelectric dispensors, inkjet printer heads generally, positive displacement pumps, syringe pumps, microfluidic diaphragm pumps, magnetostrictive diaphragm pumps, electrowetting devices, electrokinetic and electroosmotic pumps, thermopropulsive pumps, Gibbs-Marangoni devices, and hybrid devices such as piezoelectric dampeners or diffuser-nozzle heads on a syringe pump. Also contemplated are binary droplet devices.

In one embodiment, piezoelectric microdispensors such as are known in the inkjet printing industry are used to inject measured volumes of a fluid onto the impactor surface. The dispensers are compatible with a broad range of liquids from acetonitrile to 7M urea and have good solvent resistance. Because the responses to a voltage across a PZT wafer, for example, are very reproducible, extremely precise microdroplets or nanodroplets are expelled with each current pulse, which can be supplied as a square wave across the wafer electrodes. By supplying fluid from a reservoir to the pump body, the process can be repeated indefinitely, and results in a stream of droplets. The dispensers thus act as pumps. The volumes achievable are micro-, nano-, and subnano-liter sized droplets. By joining a pair of piezoelectric microdispensors to a common aperture, filling only one with a fluid and then activating the dispensers in alternation, a train of droplets separated by bubbles can be dispensed. Single aperture and multi-head devices of 3 mm OD or less are readily obtained in OEM configurations (Gesellschaft Silizium Mikrosysteme mbH, Groserkmannsdorf DE), for example.

Inkjet printer heads suitable for the present invention also include "Micro Piezo" MEMS microtechnology developed by Seiko Epson (Tokyo JP). See for example US Pat. Appl. Doc. Nos. 2007/0007860 and 2007/0048191. Newer PZT films used in the ink cavities have a displacement of 400 nm depthwise per 55 micron cavity width, acceptable for the requirements of the current invention. Also of interest are bubblejet printer heads described in U.S. Pat. Nos. 6,561,631 and 6,926,386 to Shin. The resulting inkjet heads are so small that it becomes feasible to embed the printer head in the collector module body or in a microfluidic channel in fluid communication with the collector channel, as will be discussed further below.

Piezoelectic actuators may also be used to control syringe pumps to produce the required microvolume flow. Kar (Kar, S et al. 1998. Piezoelectric mechanical pump with nanoliter per minute pulse-free flow delivery for pressure pumping in microchannels. Analyst 123:1435-1441) discloses diffuser/nozzle heads capable of adapting a syringe pump for continuous flow of nanoliter volumes without need for reloading the syringe pump. Syringe pumps, diaphragm pumps, and positive displacement pumps more generally, can be adapted to pump microvolumes of a fluid and can be installed or formed in the collector body or positioned remotely with fluidic connections to the collector channel and to a reagent reservoir.

Magnetostrictive pumps for handling nanoliter volumes are known. Examples are disclosed in U.S. Pat. Nos. 4,795,317, 4,795,318, 4,815,946, 5,129,789, and 7,316,336. U.S. Pat. No. 7,316,336 to Kaartinen is assigned to Fluilogic Oy (Espoo, FI); Fluilogic's Electromagnetic Bellows (EMB) Pump Module is distributed by ViaFlo (Hudson, N.H.) and has no seals or moving parts, dispensing discrete volumes 10 nanoliters to 1450 microliters per actuation and is thus well suited for incorporation in the devices and apparatus of the present invention.

Small pneumatic and electric diaphragm pumps adapted for microfluidic circuits are also known, as for example disclosed in U.S. Pat. No. 5,836,750 (therein termed "mesopumps") and U.S. Pat. No. 6,729,856 and US Pat. Appl. Doc. No. 2007/014522. Passive pumping systems such as by capillary action, bibulous wetting, and so forth are also contemplated.

Thermopropulsive differential heating can also be used to propel micro droplets in microfluidic channels, as described by Handique in U.S. Pat. No. 6,130,098.

"Electrowetting", in which small currents are passed through a droplet containing a conducting ion, is also suitable as a means to propel a droplet, and is a well known and established technology, for example as illustrated in U.S. Pat. No. 6,174,675 to Chow, U.S. Pat. No. 6,749,407 to Xie, and U.S. Pat. Nos. 6,565,727, 6,773,566 and 7,255,780 to Shenderov. This principle forms the basis of fluidic pumps and valves under development by Advanced Liquid Logic (Research Triangle Park N.C.).

In another aspect of the invention, the microfluidics of the microdroplet in the collector channel or on the surface of the impactor is controlled by electrical voltage pulses applied to a grid of electrodes embedded under a hydrophobic dielectric surface. Droplets have been shown to move from lower voltage to higher voltage in the range of 40 to 300 V, as described by Pamula in U.S. Pat. No. 6,911,132 and US Pat. Appl. Doc. Nos. 2006/019433 and 2007/0267294. The force acting on the liquid is a potential-dependent gradient of adhesion energy between the liquid and a solid insulating hydrophobic surface. The operating principle of the devices is a modification of "electrowetting" but avoids electroconduction in the sample liquid. If a droplet of polar liquid is placed on a hydrophobic surface, application of an electric potential across the liquid-dielectric interface reduces the contact angle, effectively converting the surface into an area of lower free surface energy toward which the droplet moves. A droplet of a polar liquid will seek out the lowest free surface energy (also termed the most "hydrophilic surface") and move toward it so as to maximize the contact area overlap with the electric field.

A particle trap having embedded circuit elements or an impactor surface having a microchip treated with a silane such as parylene, a perfluoromer such as Teflon®, a polyxylene polymer such as Lotusan® (Sto Corp, Atlanta Ga.) are suitable for demonstration of this effect, which can be adapted to move a microdroplet along the surface of the impactor, eluting impacted particles like a sticky roller, for example. By design of a track of closely spaced electrode pairs, each activated in turn, a droplet can be rapidly moved across the impactor surface and then collected or analyzed as preferred.

The tendency of a fluid to move to reduce the free energy of interfacial tension has been termed the "Gibbs-Marangoni effect" (the mass transfer of a fluid on or in a liquid layer along a surface tension gradient) and we thus term these devices "Gibbs-Marangoni devices", which include binary droplet devices such as described by Bico and Quere (Bico, J and D Quéré. 2002. Self-propelling slugs. Journal of Fluid Mechanics, 467:101; Bico J and D Quéré. 2000. Liquid trains in a tube. Europhysics Letters, 51:546).

Applying a pressure differential across the collector channel is one simple approach that can be accommodated by providing a suction pressure to a sampling duct in fluidic communication with the collector channel and particle trap. Pressure in the collector channel may be used to draw or push fluid onto the small impactor surface. Thus, also within the sense of "pump functionality" is any application of suction pressure, hydraulic pressure, or pneumatic pressure.

While not shown, pump functionalities may be bidirectional and self-priming, thereby eliminating the need for two pumps. A single, bidirectional pump functionality may be used to both inject a liquid reagent and withdraw a liquid sample from particle trap 4.

Microfluidic valves are also known in the art. Fluid flow may be unidirectional or bidirectional through valves or channels. Microvalves and checkvalves are known and may be adapted to control fluid direction and switching. These include ball valves, pinch valves, drum valves, flap valves, and peanut valves. Such valves and pumps are described in U.S. Pat. Nos. 5,498,392, 5,304,487, 5,296,375, 5,856,174, 6,180,372, 5,939,312, 5,939,291, 5,971,355, 5,863,502, 6,054,277, 6,261,431, 6,240,944, 6,418,968, 6,431,212, 6,440,725, 6,581,899, 6,620,273, 6,729,352, 6,748,975, 6,767,194, 6,901,949, 6,901,949, 5,587,128, 5,955,029, 5,498,392, 5,639,423, 5,786,182, 6,261,431, 6,126,804, 5,958,349, 6,303,343, 6,403,037, 6,429,007, 6,420,143, 6,572,830, 6,541,274, 6,544,734, 6,960,437, 6,762,049, 6,509,186, 6,432,695, 7,018,830, US Pat. Appl. Doc. Nos. 2001/0046701, 2002/0195152, 2003/0138941, 20050205816, and International Patent Publications WO1994/05414, WO 2003/004162, WO2002/18823, WO2001/041931, WO1998/50147, WO1997/27324, and so forth, which taken cumulatively describe various microfluidic devices for fluid processing and analytical operations. These microfluidic fluid control devices are well suited for incorporation in the collector modules and associated particle collection apparatus of the present invention and for directing and controlling elution, pre-processing or detection fluid reagents injected into and liquid sample withdrawn from the collector.

Returning to FIG. 1, the elution apparatus of module 1 further comprises a second pump utility or member 23 and associated microfluidic circuitry for conveying a liquid sample 30 to a sample port 19. The liquid sample contains any eluted aerosol particles or constituents thereof in the microdroplet volume injected into the particle trap. The liquid sample may be a suspension or a solution of the captured aerosol particles or constituents thereof.

The liquid eluate in the particle trap is conveyed via microfluidic ducts 11 and 15, with optional valve 16, to sampling duct 16, where liquid sample 30 is delivered at sample port 19 for analysis or archiving.

As will be discussed further below, delivery of a liquid sample to sample port 19 is optional; analysis may occur in situ prior to delivery, or may substitute for delivery of the liquid sample from the collector module.

Liquid sampling efficiency may be enhanced with the application of ultrasound to the particle trap during injection and withdrawal of fluid reagents, as will be described below.

Downstream analysis may be by physical, chemical, biochemical or molecular means for analysis. Samples collected from the collector module may optionally be archived in individual containers for that purpose, or stored in the collector module. Using networks of microfluidic channels, sample pre-processing by reagent addition may be performed continuously or in batch mode. With increased complexity, sample collection devices may be fabricated with partial or full integration of detection and/or identification capabilities, as will be discussed further below.

Figure 2:
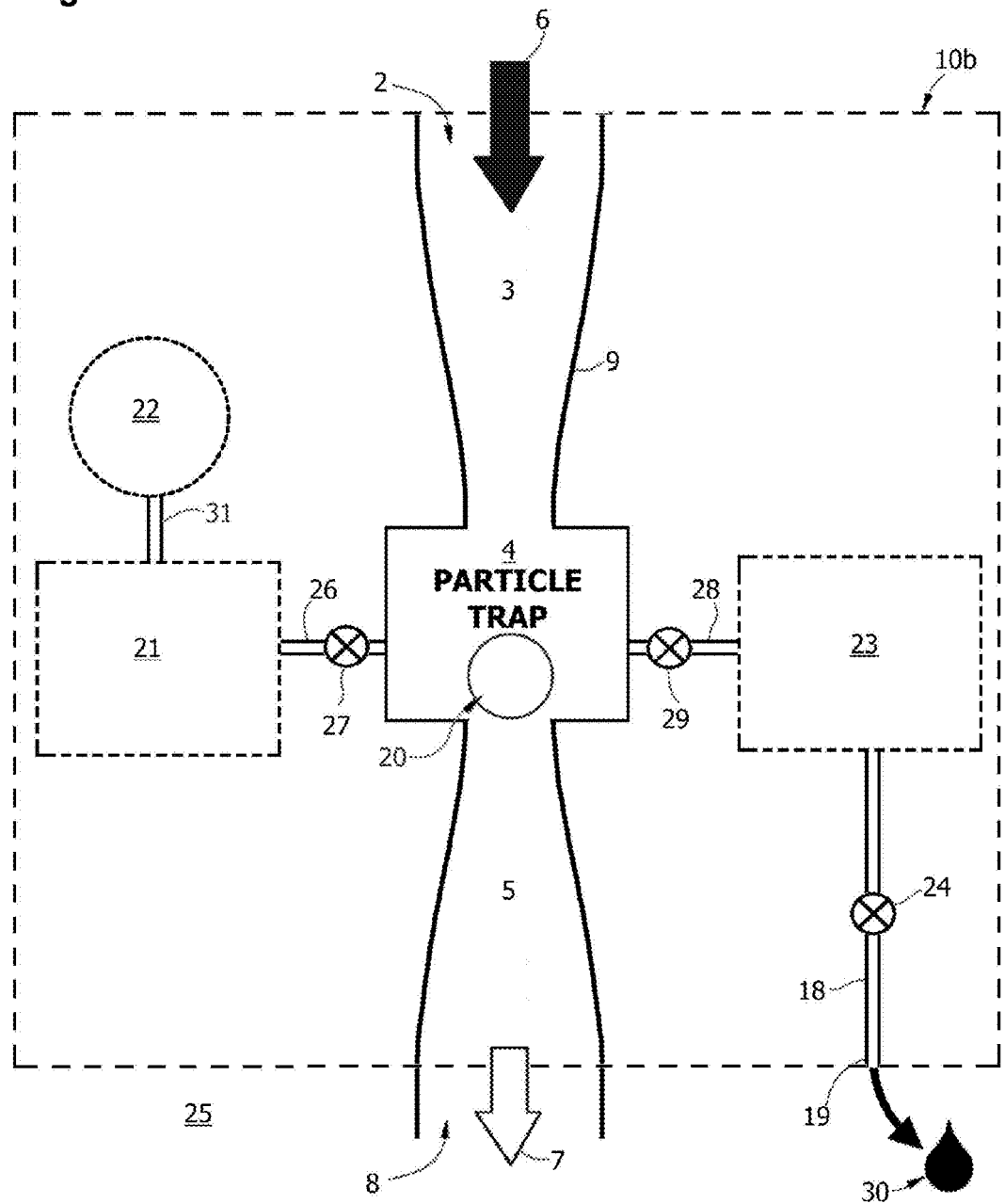
FIG. 2 is a schematic of a second collector module with particle trap.

Turning now to FIG. 2, a second generic schematic of an aerosol collector module 10b for micro-elution of captured aerosol particles is shown. Illustrated in block form are the functional components of a second embodiment of a particle collection and microelution apparatus 25. A particle trap (block 4) is disposed in a collector channel 9, the collector channel, represented here figuratively, consisting of a receiving arm 3 with intake orifice 2 and an outlet arm 5 with outlet orifice 8. A gas stream 6 with aerosol particles enters the collector channel through the intake orifice and transits the particle trap 4. The particle trap may be an inertial impactor, such as a centrifugal inertial impactor or a bluff body impactor, or may be an electrostatic precipitator. The gas stream 7, depleted of particles, exits the collector channel 9 at the base of the module through outlet orifice 8. Aerosol particles accumulate as a mass or sample in the particle trap.

The elution apparatus of module 10b comprises a pump functionality or member (block 21) with associated fluid reservoir 22. The functional components of apparatus 25 with dashed outlines may be mounted within module 10b or may optionally be mounted externally and associated through fluidic connections with module 10b. Fluid from reservoir 22 is injected via microfluidic ducts 31 and 26, optionally with valve 27, into particle trap 4, in the form of a discrete microdroplet volume. Microfluidic duct 26 is termed a microfluidic injection duct. In the particle trap, the microdroplet volume is contacted with the impactor surface or surfaces of the trap and captive aerosol sample is eluted in the confined structure of the particle trap 4, thereby forming a liquid sample.

The liquid sample may be either analyzed in situ, treated for further analysis in situ, or delivered for downstream analysis. For in situ interrogation of the sample, an optical or acoustic window 20, lens flat, or waveguide in the collector body is optionally provided. Techniques that may be used to interrogate the liquid suspension include fluorescence, light absorption, and light scattering measurements of the liquid sample containing the eluted particles inside the collector, for example. Optical or acoustic window 20 may also be used to interface the collector body with an ultrasound transducer so that the liquid sample may be treated to disrupt and release its contents for analysis. The ultrasonic transducer, typically a PZT crystal laminate, may be integrated into the collector body in one embodiment.

For delivery of the liquid sample for downstream analysis, optional pump functionality or member 23 is provided. Sampling ducts 28 and 18, with optional valves 29 and 24 are used to convey the liquid sample from the particle trap to a sampling port 19, where liquid sample 30 is delivered for analysis or archival storage.

Other combinations are conceived. The liquid sample, for example, may be conveyed from the collection module via outlet arm 5. While not shown, pump functionalities may be bidirectional and self-priming, thereby eliminating the need for two pumps. A single, bidirectional pump functionality may be used to both inject a liquid reagent and withdraw a liquid sample from particle trap 4.

Alternatively, the treatment or analysis of the liquid sample may require introduction of additional reagents and the use of additional pumps. These techniques may require more sample manipulation (thermal cycling, mixing with additional reagents, and so forth). A microfluidic network with valve, channels and pumps to conduct these reactions may be incorporated in the collector module or as part of an associated apparatus. A branched microfluidic pathway may be provided so that air bubbles may be interjected between a train of microdroplets. A downstream debubbler may be desired to separate the liquid sample from any injected air, and so forth. Various embodiments containing inertial impactors and electrostatic precipitators will be described in more detail below.

Methods of Use

The apparatus of FIGS. 1 and 2 are essentially representative devices for accomplishing a series of steps and can be described by listing the series of steps performed by the device or apparatus. The cycle of steps may be repeated. Thus in another aspect, the invention is a method. The method can be described in general terms as: (i) directing a concentrated gas stream of aerosol particles through a collector channel, (ii) deflecting that gas stream (inertially or electrostatically) so that aerosol particles are impacted and adhere to an impactor surface, (iii) periodically eluting the aerosol particles from the surface in a liquid sample by contacting a small liquid droplet volume or a series of droplet volumes with the impactor surface, (iv) optionally conveying the resuspended or solubilized aerosol particles to a sampling port for analysis, v) optionally preparing the liquid sample for analysis by treating the liquid sample in situ, and/or vi) optionally analyzing the liquid sample in situ.

The first step is to deliver concentrated aerosol particles to a collector. A complete sampling system may include an upstream aerosol concentrator module incorporating a virtual impactor and aerodynamic lens, or other air-to-air concentrator, and an adapter for sealedly connecting the concentrator module to the downstream collector.

The second step is to impact the particle beam on an impactor so that the particles are captured on the impactor surface. Either centrifugal inertial impactors, bluff body impactors, or electrostatic precipitators may be used for this purpose. These will be discussed in more detail in sections below.

The third step is to inject a small (ie. nanoliter- to microliter-sized) droplet into the collector channel and contact it with the impactor surface or surfaces so that the droplet effectively scavenges the deposited particles (or their chemical constituents) from the collection surface.

Approaches for particle microelution from the impactor surface in an elution droplet include surface modification to alter the surface energy of the collector walls, use of elution fluids containing surfactants, co-surfactants, wetting agents, solvents, co-solvents, or dissolution reagents to enhance the release of particles from the collector walls, or use of an ultrasonic field can be used to assist in dislodging the particles from the collector walls. The collector module bodies of the present invention are readily adapted to be interfaced with a small transducer horn of an ultrasound generator, for example. For biological aerosols in situ lysing is possible via physical, electrical, chemical or thermal treatment of the organisms to release their DNA/RNA.

Dissolution of the aerosol particle to release a constituent, can be achieved, for example, with a chaeotrope such as guanidinium HCl or concentrated urea, optionally with a surfactant such as sodium dodecyl sulfate (SDS) and alkali. Chemical compounds and toxins of non-biological origin in an aerosol [for example excipients used to weaponize a bio-aerosol] can be eluted for analysis by using a solvent such as methanol or acetone (for gas chromatography), aqueous ethanol or acetonitrile (for liquid chromatography), or acid (for inductively coupled plasma mass spectroscopy) as the elution and transport liquid, for example.

Optionally the method can comprise a step in which the liquid sample is conveyed to a sampling port for downstream analysis or archiving. Pump functionalities previously discussed may be used for this purpose.

Optionally, the method can comprise performing a preprocessing step for preparing the sample for analysis, for example by lysis of microbial cells or by release of nucleic acid, or by dissolving a sample matrix such as a mucous particle. Various optional chemical or physical pre-processing treatments are envisaged, including thermal treatments, ultrasonic treatments, particle digestion treatments, hydrolysis treatments, and so forth. These treatments can comprise a chemical treatment contacting said aerosol particle with a second reagent having the purpose of chemically modifying a constituent of the liquid sample; a thermal treatment or an ultrasonic treatment having the purpose of eluting or lysing the captured aerosol particle in the liquid sample; a radiological treatment with microwave or other radiation treatment having the purpose of lysing any captured aerosol particle in the liquid sample; a mechanical treatment with mechanical manipulation (such as mixing or moving) of a liquid sample with captured aerosol particle within the collector channel, in short treatment means for preparing the sample for analysis or for performing pre-analytical processing steps.

Optionally, a step for in situ detection may be employed. In one instance, a biochemical, physical, or molecular characterization of the recovered aerosol contents is undertaken in situ. Various means for detecting a particle or particle constituent are used for this purpose. This may involve determining whether a measurable characteristic of a sample exceeds a threshold value before subjecting the liquid sample to more thorough analysis. A screening step, as would differentiate a sample that is a potential threat from a sample that is a non-threat, is also contemplated in the invention. Analytical procedures can involve various technologies, and include without limitation steps for:

1. inducing fluorescence of specific constituents of the liquid suspension, detecting emitted fluorescent radiation, having the purpose of identifying those constituents of interest based on the spectrum of the emitted light;
2. measuring optical absorption of the liquid suspension at various wavelengths; having the purpose of identifying those constituents of interest, such as tryptophan, NADH or Vitamin B, based on the spectrum of the absorbed light;
3. measuring light scattered from the sample in various directions; having the purpose of quantitating or identifying those constituents of interest based on the spectrum of the scattered light;
4. subjecting the sample to nucleic acid amplification and real-time PCR; having the purpose of identifying those constituents of interest based on the fluorescence of a molecular beacon or probe;
5. subjecting the sample to an immunological assay; having the purpose of identifying those constituents of interest based on an antigen:antibody reaction; and/or,
6. subjecting the sample to at least one spectroscopic measurement technique such as Raman spectroscopy (RS), surface-enhanced Raman spectroscopy (SERS), laser induced breakdown spectroscopy (LIBS), spark-induced breakdown spectroscopy (SIBS), surface plasmon resonance (SPR), or methods using fluorescence of particle constituents, having the purpose of identifying those constituents of interest.

This process of analysis may also involve a step for saving the droplet or droplets, or a part thereof, in a container or an array of containers for later analysis. In one instance, the collector is a disposable module and is removed from the apparatus and transported or saved for analysis off line.

More generally, the method may involve either a) releasing the particles into a liquid to form a suspension, or b) releasing all or some constituents of the aerosol particle, airborne agent, or excipient therein, into a liquid volume to form a solution, and then either a) analyzing the collected liquid sample inside the collector or b) transporting the liquid sample to an off-line detector for further analysis.

Once the aerosol sample, or the desired chemical or biological constituents of the sample, is solvated in the liquid droplet they can be processed in a number of ways. These include steps for:

1. optionally pre-processing the sample fluid in preparation for a subsequent detection step;
2. optionally performing an in situ analysis;
3. optionally performing an in situ assay for detecting a signal above a threshold level that will trigger further analysis;
4. optionally conveying the droplet via a sampling port and pumping means to a detector in fluidic communication with the collector body and performing an analysis downstream;
5. optionally analyzing the liquid sample in an integrated device, the device comprising the collector and a microfluidic circuit with on-board analytical module or modules such as a self-contained microfluidic circuit for performing PCR on nucleic acid extracted from the liquid sample or for performing an ELISA assay on constituents of the liquid sample;
6. optionally archiving the liquid sample, or a part thereof, in a container or an array of containers for later reference; and/or,
7. optionally delivering the entire collector assembly as a aerosol collector module containing the liquid sample to an off-line detector.

The analysis of the captured aerosol particles may be performed inside or outside the collector. The captured aerosol contents may be interrogated in liquid suspension or solution in situ or conveyed to a downstream site for analysis. Techniques that may be used to interrogate the liquid suspension include fluorescence, light absorption, and light scattering measurements of the liquid sample containing the eluted particles inside the collector. An optical window, lens flat, or waveguide in the collector body is provided for this purpose. The detection and analysis of the eluted sample may be performed downstream of the collector by a number of methods which require delivery of aerosol or its chemical constituents in liquid solution or suspension, for example surface plasmon resonance, high performance liquid chromatography/mass spectrometry (HPLC/MS), FABS, ICP/MS (Perkin-Elmer), GC/MS, and so forth. PCR, nucleic acid amplification, antibody techniques, and molecular biological, immunobiological techniques and other means for detection more generally may also be used.

Centrifugal Inertial Impactors

Figure 3:
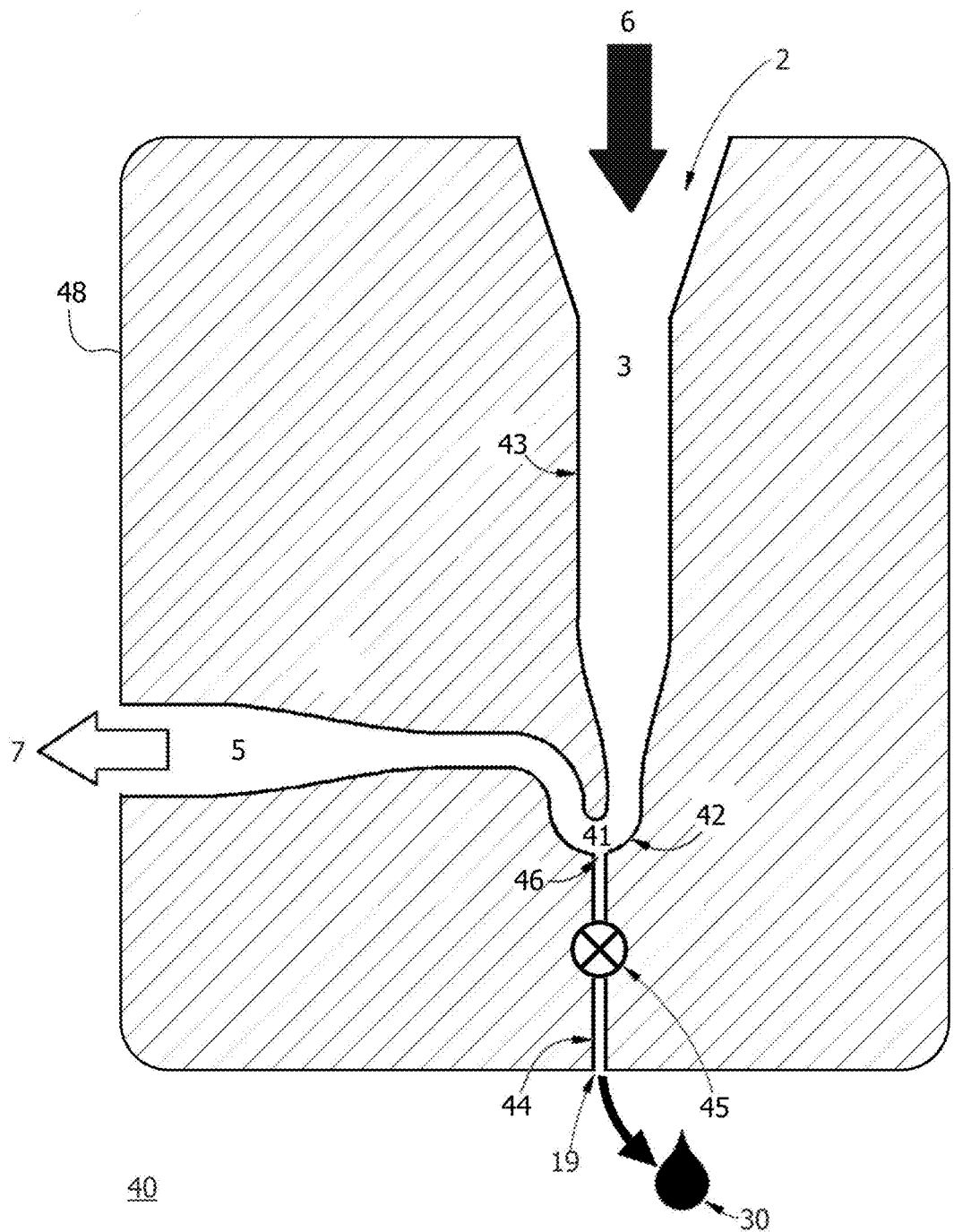
FIG. 3 is a schematic of a collector apparatus with centrifugal inertial impactor and droplet injection and elution mechanism.

FIG. 3 is a schematic of an embodiment 40 of a collector apparatus or module of the invention, where the particle trap 41 is configured as a "centrifugal inertial impactor" having impactor surface 42. While not limited thereto, the collector module 40 is shown as having a plastic solid body 48.

Collector body 48 contains or encloses a collector channel 43 consisting of intake orifice 2, receiving arm 3 and outlet arm 5. A gas stream 6 flows through the collector channel in response, for example, to a suction pressure applied to the outlet arm. Disposed in the collector channel is inertial impactor 42, formed here by a concavoconvex "trap-like" curvature of the collector channel.

In operation, a gas stream 6 with entrained aerosol particles enters the collector channel at the top of the collector body. Aerosol particles not deflected with the gas streamlines in the bending portion of the channel are captured by inelastic impaction on the inertial impactor surface 42. The aerosol-depleted gas stream 7 or "bulk flow" exits the collector body at outlet arm 5. A liquid reagent injected through injection duct 44 and valve 45 contacts and elutes any deposited aerosol particles or constituents thereof in particle trap 41. The resultant liquid sample, containing a solution or suspension of the aerosol particles, is optionally analyzed or treated in situ or is conveyed to an external microfluidic circuit or other analytical means via a sample port 19.

As shown, injection duct 44 joins the collector channel at an injection port (46) or "tee" in the particle trap. It may be preferable to locate the tee downstream from or upstream of the impactor surface. The tee is generally proximate to the inertial impactor surface.

To collect the liquid sample, if desired, an auxiliary pump may be used, or the pump utility may be configured to be bidirectional. In another embodiment, the sample liquid 30 can be conveyed under differential pressure out of the collector body through outlet arm 5. During the sampling process, the gas stream and suction pressure is turned off or redirected using valves or stopcocks. Liquid sample 30 may be analyzed or retained for future analysis. Alternatively, the highly concentrated sample liquid can instead advantageously be analyzed in situ in the collector channel with a suitable analytical apparatus, such as spectroscopic analysis of the sample via an optical window in the collector body.

The collector channel 43 and particle trap 41 are designed so that collision with the impactor surface 42 is substantially an inelastic collision. General expressions for the mathematics of inertial particle impact are well known (see Hinds, W C, "Aerosol Technology: Properties, Behavior and Measurement of Airborne Particles", 1982, Wiley-Interscience). Slip coefficients may be used for calculating cut-off parameters for sub-micron particles. Cut-off size is a useful parameter in comparing inertial impactors. In the collectors of the present invention, we achieve "cut-off sizes" of less than 0.5 microns aerodynamic diameter and sampling flow rates in the range of 0.05 to 10 L/min range, depending on the size of the channel and the application. While this discussion is directed principally to channels with a characteristic dimension of less than 1500 microns, we have also seen that the width of the channel, in the case of a rectangular channel for example, permits flow rates to be increased without modifying the physics substantially.

Collector module 40 can be fabricated by a number of methods, including carefully bending glass capillaries or plastic tubing, by molding mating halves of a plastic body, by lamination of stenciled and laser-cut films, or by what is termed three-dimensional photolithography, in which shapes containing internal structure are built layer-by-layer by laser-patterned photoactivated polymerization of a liquid monomer. The collector channel may be round or rectangular in cross section. In some instances the collector channel is a bent glass capillary impactor. Fabrication of a micro-U-tube of a glass capillary requires achieving a small radius of bending without breaking the capillary or collapsing its inner bore. Good results for bending fused silica capillary are obtained using a technique reported for fabricating a capillary spectrometer vessel (as described in U.S. Pat. No. 5,469,061 to Linehan). The bending is accomplished by holding the capillary upright, slightly inclined from plumb, heating the capillary with a torch, and letting it bend due to the force of gravity. This method produces tight, repeatable bends, for example a capillary (300 microns ID/665 microns OD) can be bent with heating into a U-shape with a radius of curvature of about 1 mm ($R_c$=0.66×ID, where ID is the internal diameter). The capillary does not collapse in the process and can optionally be potted in an epoxy collector body after fabrication. Another approach is to use plastic tubing bent in around a cylindrical peg in a jig. In a preferred method of fabrication, molded parts with mating female "half-channel" or recessed features are joined together to form the collector channel and associated microfluidic ducts.

Figure 4A:
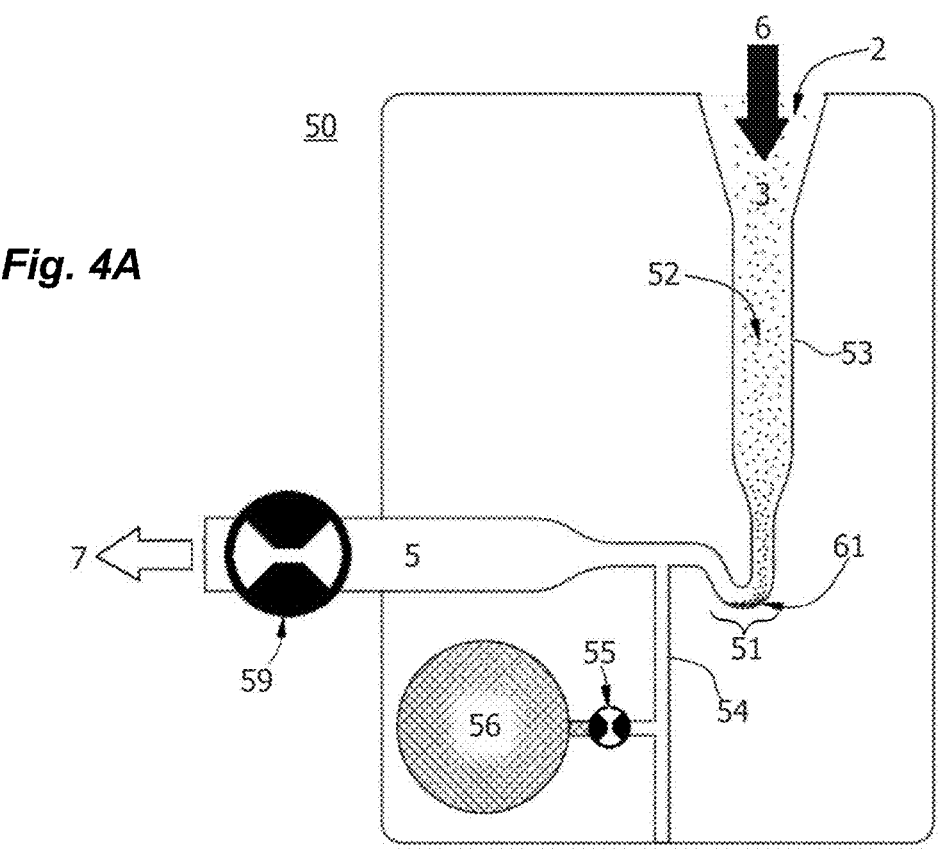
FIGS. 4A through 4D illustrate a process of operating a collector apparatus having a centrifugal inertial impactor and on-board elution fluid reservoir.
Figure 4B:
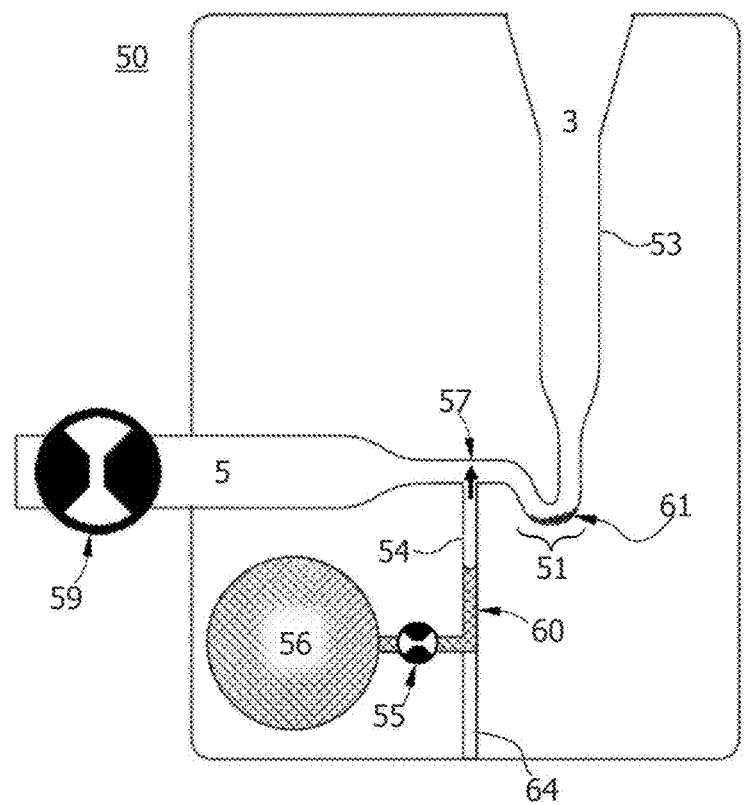

FIGS. 4A through 4D describe use of a collection module 50 with on-board reagent reservoir 56. Dispensing of the reagent occurs by action of a pressurizable diaphragm over the reagent chamber and valve 55. As shown in FIG. 4A, an aerosol stream 6 is drawn in at the top of the collector channel 53 via intake orifice 2, receiving arm 3 and particle trap 51, where aerosol particles are deposited according to the cut-off characteristics of the inertial impactor. Particle-depleted outlet stream 7 exits the outlet arm 5 at an orifice, which is connected to a suction pressure. Outlet arm 7 is provided with a stopcock 59, for turning on and off the vacuum connection. Aerosol particles form a particle deposit 61 on the inside of the particle trap 51 by centrifugal impaction.

Figure 4C:
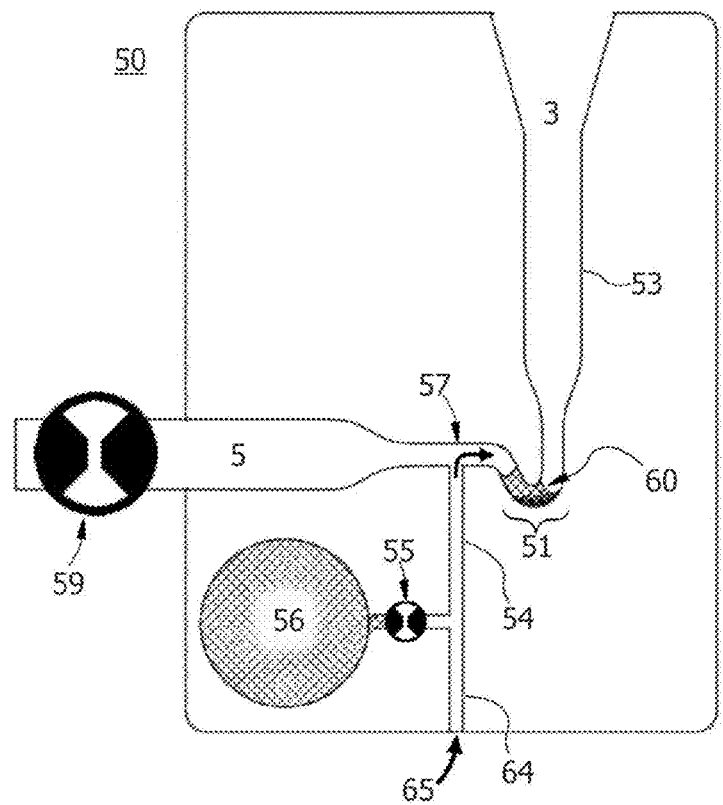
Figure 4D:
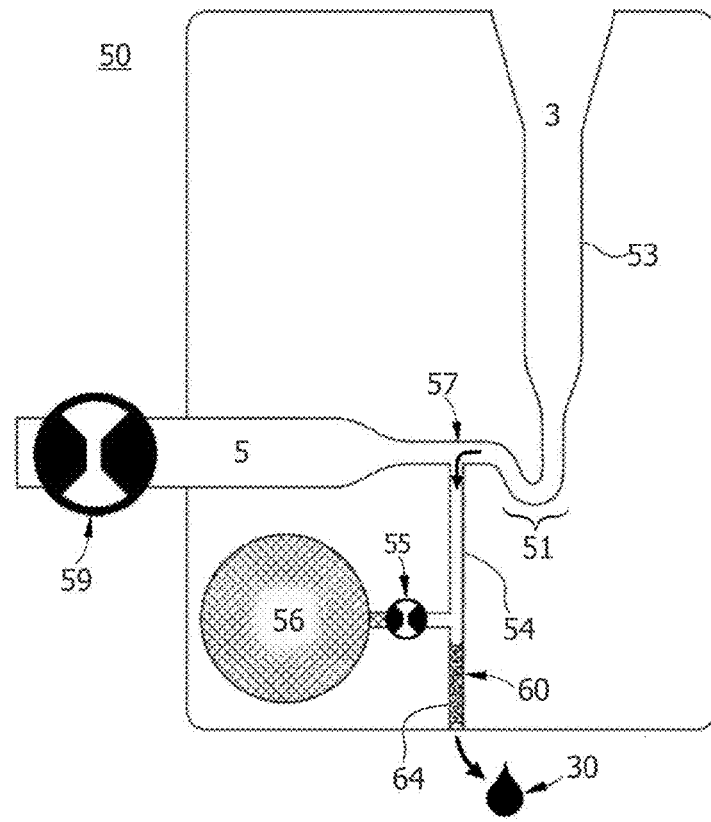

To elute captured particles and collect a liquid sample from the impactor, stopcock 59 is closed (FIG. 4B), valve 55 is opened, and a microdroplet volume 60 of an elution fluid from reagent reservoir 56 is injected into the collector channel via microfluidic injection duct 54 and tee 57. Valve 55 is then closed. The microdroplet 60 is moved onto the impactor surface, thereby contactingly eluting the deposited particles 61 from the impactor (FIG. 4C). A remote micro-syringe pump (not shown) fluidly attached to sampling duct 64 is used, for example, to supply air 65 to push the droplet 60 through injection duct 54, tee 57, and onto the impactor surface. The syringe pump is then reversed, drawing the microdroplet volume 60 out of the collector channel via tee or "injection port" 57 and sampling duct 64 (FIG. 4D), where the liquid sample 30 is collected for analysis or archiving. In this way a highly concentrated aerosol suspension or solution is obtained in a microvolume of liquid sample 30. While not limited by particularities of detail, this method is generally applicable.

By extensive experimentation, we have discovered working inertial impactors that can be designed and fabricated with dimensions and features ranging from 200 to 1500 microns in the collector channel and impactor while operating at subsonic gas stream linear velocities. Aerosol particle deposition on the walls of the collector, depending on the nature of the particles, need not occur solely due to inertial forces acting on the particles; the deposition may be forced or aided by electrostatic forces.

Figure 5A:
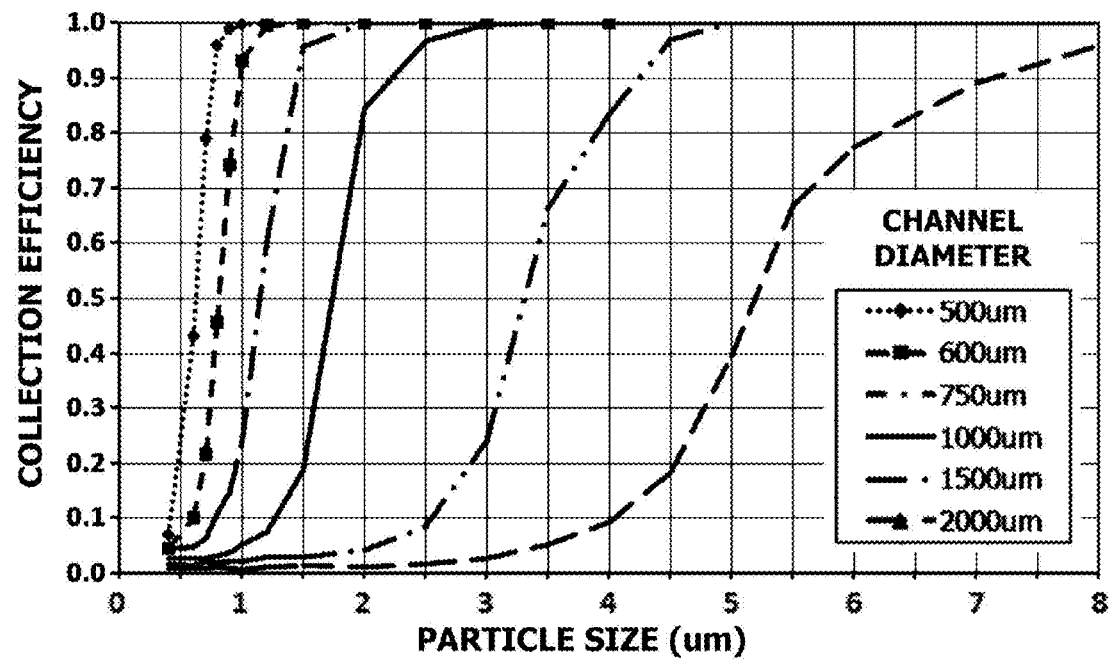
FIG. 5A demonstrates the effect of collector channel diameter on particle capture at a gas flow rate of 0.5 L/min.

FIG. 5A describes the results of calculations showing the effect of collector channel diameter on cut-off size for centrifugal inertial impactors. The cut-off size ($r_p$) corresponds to a collection efficiency of 50% for that particular particle size.

For comparison, all curves are constructed at constant flow rate of 0.5 L/min at STP; shown here are plots for 0.5 L/min in tubular collector channels having, from left to right, diameters of 500, 600, 750, 1000, 1500 and 2000 microns, respectively.

Figure 5B:
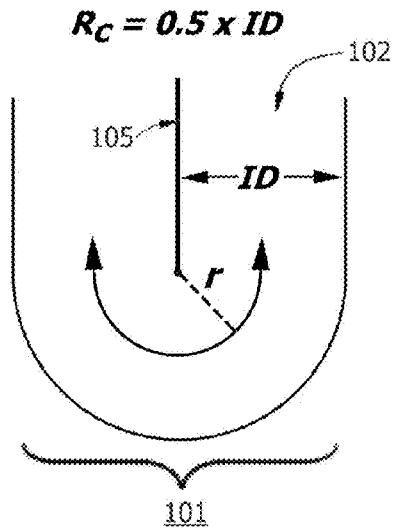
FIGS. 5B and 5C describe particle traps with radius of curvature $R_c$ equal to one-half and two-thirds the internal diameter of the collector channel, respectively.
Figure 5C:
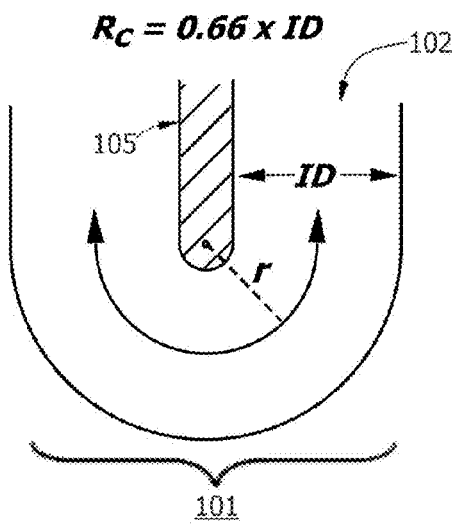

The radius of curvature ($R_c$) for all the illustrated impactors of FIG. 5A is 0.66×ID, a constant; ie. a bending radius of 2/3 the characteristic dimension (channel height or diameter ID). Because the minimum theoretical bending radius is 0.5×ID, these figures represent generally optimized collector geometry for tubular and rectangular channels. Shown in FIGS. 5B and 5C are centrifugal impactor structures having a radius of curvature of 0.5×ID and 0.66×ID respectively. The radius $R_c$ is taken from the axial center of the bend to the centerline of the channel, while maintaining a constant characteristic dimension or internal diameter ID of the channel. Comparison reveals that for an impactor with $R_c$ less than 0.66×ID, the "septum" 105 between the two arms of the impactor is nearing impracticably thin and as $R_c$ approaches 0.5×ID (FIG. 5B), the thickness of the septum 105 approaches zero, a limit that cannot be overcome. Also labeled on the diagram are the receiving arm of the collector 102 and the centrifugal impactor or "particle trap" 101.

The dimensions of the collector and centrifugal impactor are characteristically microfluidic or near-microfluidic dimensions. The dimensions of the particle trap 101, are such that at least one cross-sectional dimension of the collector microchannel and impactor surface is generally smaller than 1500 microns and the radius of curvature as measured along the centerline of the collector channel is generally 0.5 to three or about ten times the height or diameter of the channel. Typically, the "trap" portion of the collector channel forming the centrifugal impactor surface has at least 120 degrees of bending arc, more preferable 180 degrees, although 360 degree loops are also conceived and is generally less than 1500 microns in one dimension. The trap portion may have a radius of curvature which is greater than 0.5 and is generally less than 10. The volume in the trap portion is thus generally less than 10 microliters, and volumes of liquid reagent satisfactory for "microelution" are less than 10 microliters, preferably less than 1 microliter.

Returning to FIG. 5A, the corresponding average gas velocities $V_{dot}$ were calculated to be 42.4, 29.5, 18.9, 10.6, and 4.7 meters per second. The corresponding particle cut-offs (as aerodynamic diameter) were found to be about 0.63 micron for the 500 micron ID trap, 0.81 micron for the 600 micron ID trap, 0.96 micron for the 750 micron ID trap, 1.74 micron for the 1.0 mm ID trap, and 3.31 micron for the 1.5 mm ID trap.

The significance of these figures for capture of bioaerosols is clear. Bacteria such as *E. coli* have an aerodynamic diameter in the range of 0.7 to 1.0 microns, *Bacillus anthracis* spores are in the range of 0.8 to 1.5 microns, and viruses are in the range of perhaps 20 to 120 nm (although viruses are typically aerosolized as larger composite particulates such as bronchial secretions or weaponized particulates containing excipients). Therefore, the ability to detect particles in the sub-micron range, down to 0.7 microns, is critical. As can be seen, centrifugal particle traps having diameters in the range of 200 to 750 microns ID are shown to meet the required criterion for cut-off size at flow rates in the range of 0.5 to 1.0 L/min. It should be recalled that the collector throughput is frequently a minor flow received from an upstream concentrator array, and taking 1000:1 or 2500:1 as maximal reasonably achievable flow splits in air-to-air concentrators at present, suitable collection efficiency and throughput are obtained. Happily then, a useful sub-micron particle size cutoff and flow throughputs of 1250, 2500 L/min, or greater, are obtained with the inertial impactor collectors described in the figure.

In fact, particle traps having an ID or characteristic dimension (typically the height) of the channel of 0.2 mm were also operable in our hands, and achieve sub-micron cut-off sizes with flow rates as low as 0.07 to 0.1 L/min. Larger flow rates may be achieved by widening the channel while maintaining the radius of curvature, as in a rectangular channel having width greater than height. Thus, for practicing the invention, we conceive as useful channels having a characteristic dimension of 50 to 1500 microns and mean flow rates in the collector module of 0.05 to 10 L/min. With wider channels in the collector, and using flow splits of 2500:1 in an upstream air-to-air concentrator, sampling rates of 25 cubic meters per min of air are possible.

Figures 6A, 6B:
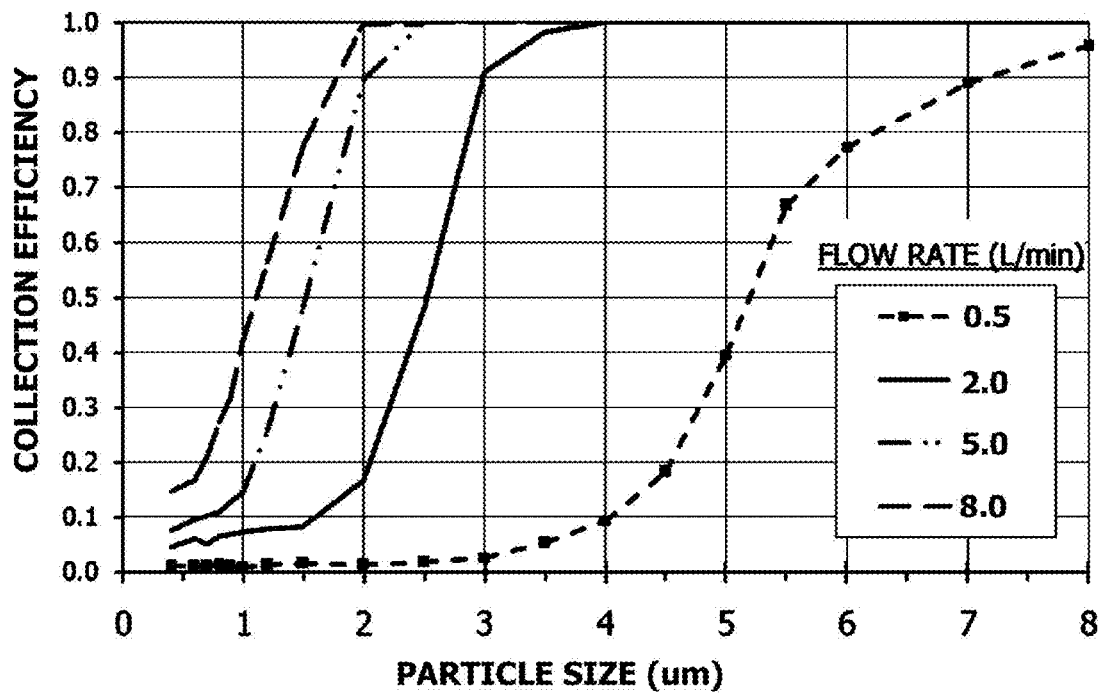
FIG. 6A demonstrates the effect of gas flow rate on particle capture in a larger collector channel.
FIG. 6B is a table showing the effect of collector channel diameter on volume of a particle trap.

In contrast, at 2 mm ID, the performance is reduced. It can be seen from FIG. 5A that the cut-off size in a 2 mm tube at 0.5 L/min is greater than 5 microns; not satisfactory for many applications. Increased velocity $V_{dot}$ does not correct this deficiency. Shown in FIG. 6A is the effect of increased velocity on particle collection efficiency as a function of particle size. It can be seen that as velocity of the gas stream is increased from 0.5 to 8.0 L/min, the particle size cut-off still does not reach the desired sub-micron range. Certain technical difficulties are expected in configuring a 2 mm tube for higher throughput velocities. In contrast, although mean linear velocity of a 0.5 mm impactor trap operated at 0.5 L/min and a 2 mm impactor trap operated at 8 L/min are essentially equal (about 40 m/s), the particle cut-off in the 0.5 mm device is 0.63 microns versus 1.15 microns in the 2 mm device due to the faster maximum linear velocity and laminar velocity profile. These figures assume optimal collector bend radius for each device. Interestingly, for a 300 micron collector channel, the mean linear velocity in the trap is almost 120 m/s at a $V_{dot}$ of only 0.5 L/min, indicating that smaller, sub-millimeter collector channels are qualitatively superior over the 2 mm channel, successfully capturing the required range of particles at split fractions which more efficiently use the upstream capabilities of a compatible aerosol concentrator. Taking 3×ID as the length of the centrifugal trap, where ID is the internal volume of the channel, the volume of the trap segments are readily compared as a function of diameter (here considering only tubular channels). The data is tabulated in FIG. 6B. The volume of the particle trap for channels of 100, 200, 300, 500, 600, 750, 1000, 1500, and 2000 microns ID shifts dramatically from 20 microliters for a 2 mm particle trap to 2 nanoliters for a 100 micron particle trap, essentially a 10,000-fold decrease in volume for a 20-fold decrease in diameter. Thus the synergy of use of a particle trap having microfluidic or near microfluidic dimensions extends not only to the success in capturing sub-micron particles, but also resuspending or solubilizing those particles in a dramatically smaller volume, a microliter volume, and in some cases a nanoliter volume.

Again the technical advance is that with combinations having an inertial collector of the present invention, aerosol particles in a cubic meter of air or more can be reduced to a liquid volume of a few microliters, or even a few nanoliters! The invention is thus a very highly concentrative air-to-liquid converter, generating microdroplet liquid samples of concentrated aerosol particles. What is surprising is that the microfluidic-sized or near-microfluidic sized particle traps can be successfully operated—as demonstrated by the following data is taken from actual experimentation.

Figure 7A:
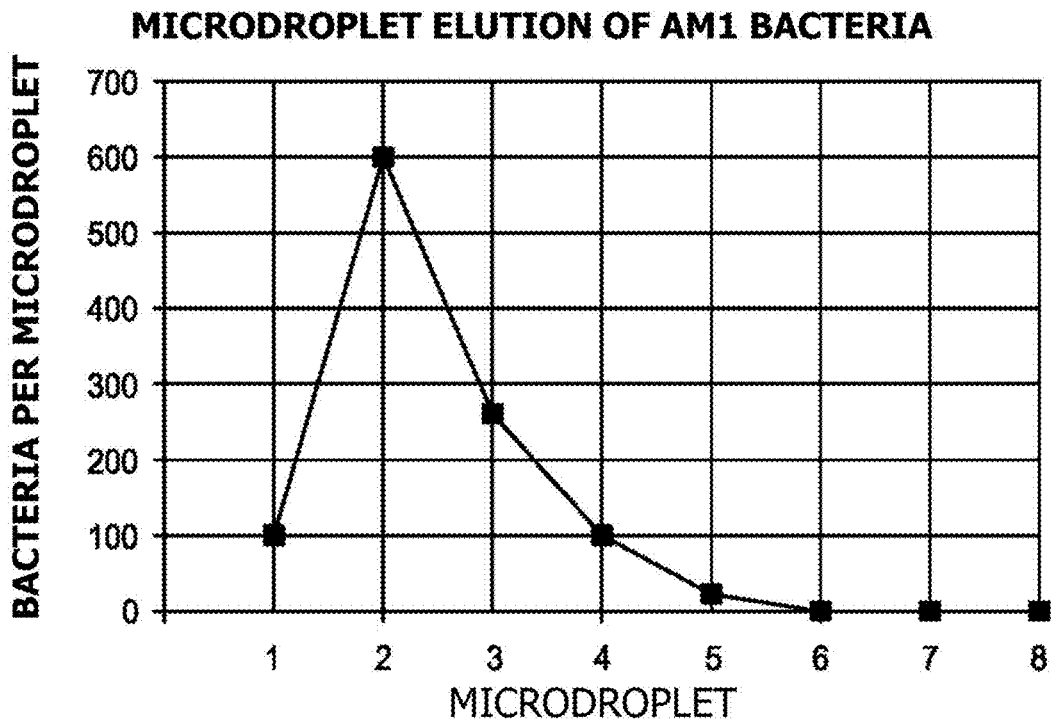
FIG. 7A shows experimental data for recovery of bacterial cells in a centrifugal impactor using 500 nanoliter droplets of saline as an elution reagent.

FIG. 7A shows the results of an experiment in which particles trapped in a centrifugal impactor were eluted with microvolume droplets of a fluid. The particles used in the experiment are viable bacteria of a species (*Methylobacterium extorquens* AM1) not characteristic of ambient air. After aerosolizing and collecting a sample, a series of microvolume droplets was used to elute the bacteria from the impactor surface. In this case, aqueous 0.1% Tween 20 was used as the elution fluid. The volume of each droplet was 500 mL. Each 500 nanoliter droplet was injected into the collector channel and collected separately for analysis by culture. Bacteria per microdroplet represent the number of viable cells recovered in each droplet. As can be seen, after an initial wet out, most of the bacterial cells appear in the second droplet passed through the collector channel. Thus most of the viable bacteria were collected in a single drop! This surprising result demonstrates feasibility of the process conceptualized generally in FIG. 4.

Figure 7B:
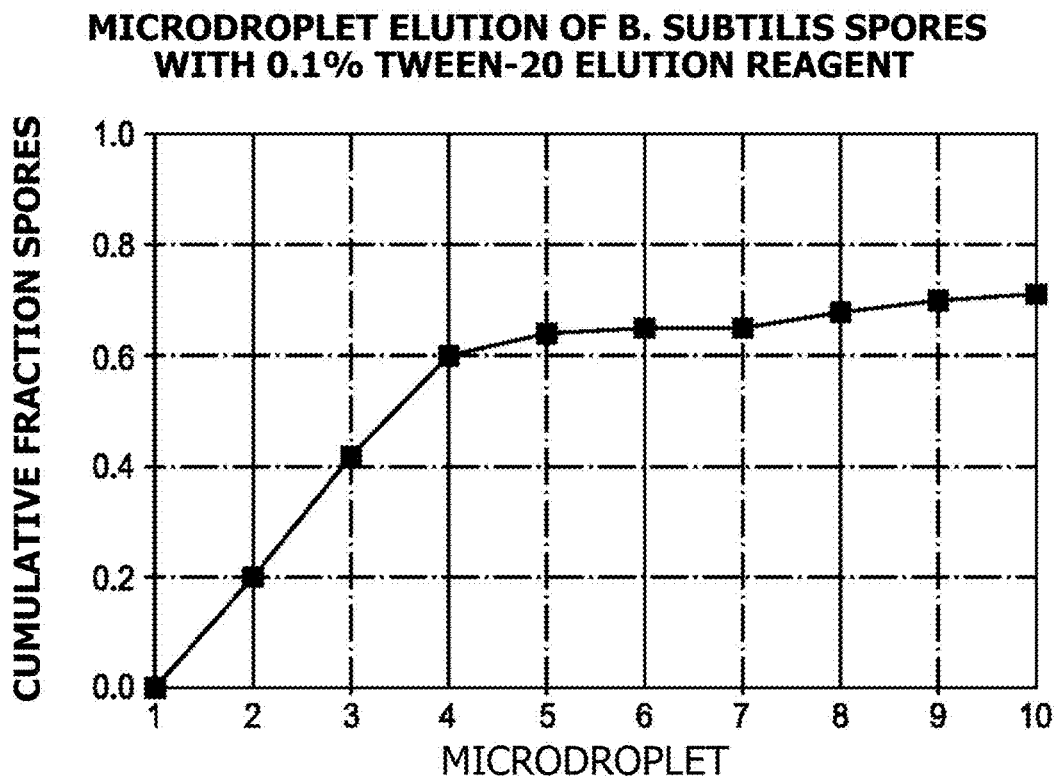
FIG. 7B shows experimental data for recovery of *bacillus* spores in a centrifugal impactor using 500 nanoliter droplets of 0.1% Tween-20 as an elution reagent.
Figure 8A:
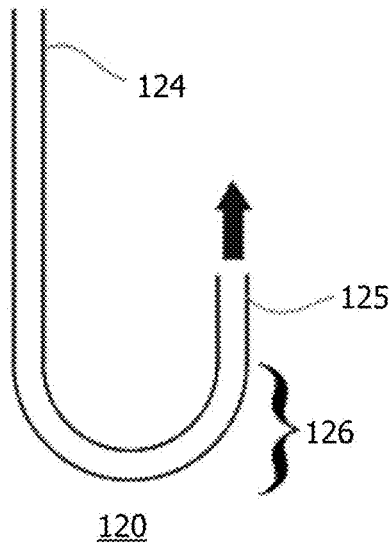
FIGS. 8A to 8D are four views of centrifugal impactor configurations.
Figure 8B:
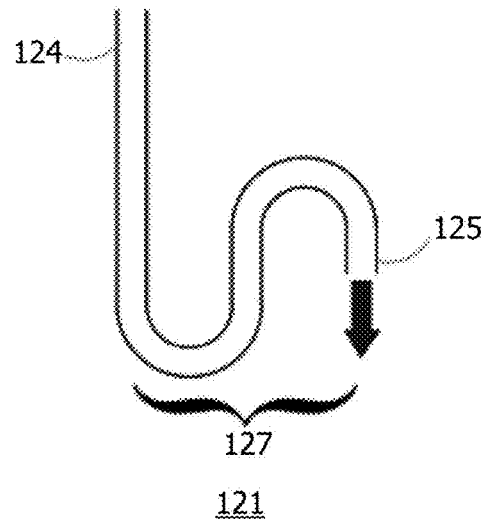
Figure 8C:
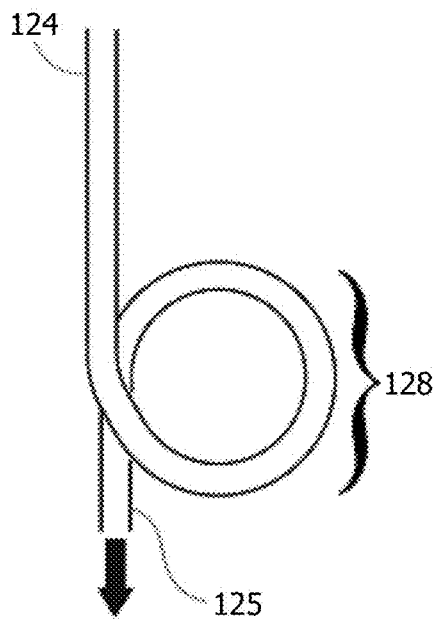
Figure 8D:
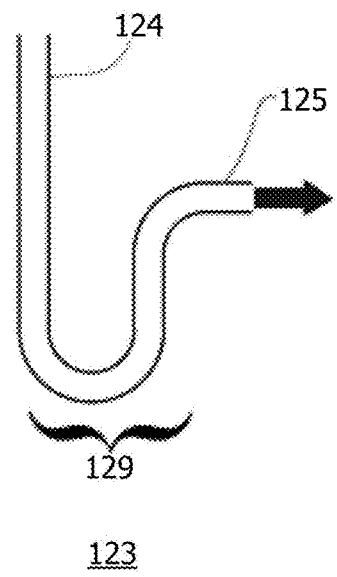

A similar result is shown in FIG. 7B, in which the target particles were bacterial spores (*Bacillus subtilis*) of a non-pathogenic cousin of the Anthrax pathogen. Again, 500 nanoliter droplets of an elution reagent were injected into a micro-U-tube collector channel containing spores captured from a gas stream. Each droplet was recovered and analyzed by culture. Spores per microdroplet are plotted cumulatively. Surprisingly, it can be seen that by the fourth droplet, substantially all of the viable spores were recovered, corresponding to a total eluate volume of 2 microliters and a cumulative elution efficiency of almost 70%. Estimates of total spores in the system are based on spore counts from filter membranes blocking the outlet stream 7.

Variants of centrifugal impactor particle trap geometry (120,121,122,123) are contemplated, as shown in FIGS. 8A-D. The exact shape is chosen for efficiency and convenience, and the internal bore may be variable in diameter. Each impactor is shown with a receiving arm 124 and an outlet arm 125. Shown in brackets (126,127,128 and 129) are the trap-like concavoconvexedly curved portions of the collector channel which form the centrifugal impactor surfaces. These bent tubular channels are generally configured with bending segments having more than 120 degrees of bending, optionally up to 360 degrees of bending.

Figure 9A:
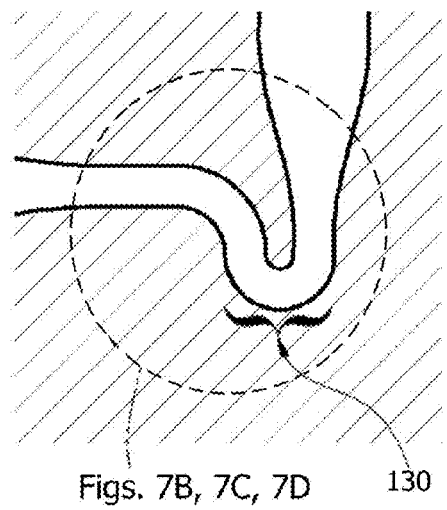
FIG. 9A shows by dashed line the particle trap having features referenced in FIGS. 9B-D.
Figure 9B:
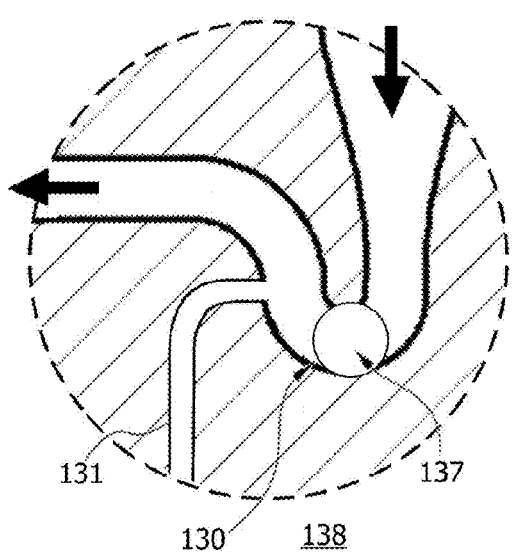
FIGS. 9B-D show embodiments of a centrifugal-impactor type particle trap configured with a microfluidic injector duct, injector/sampling duct, or tandem injector and sampling ducts with valving.
Figure 9C:
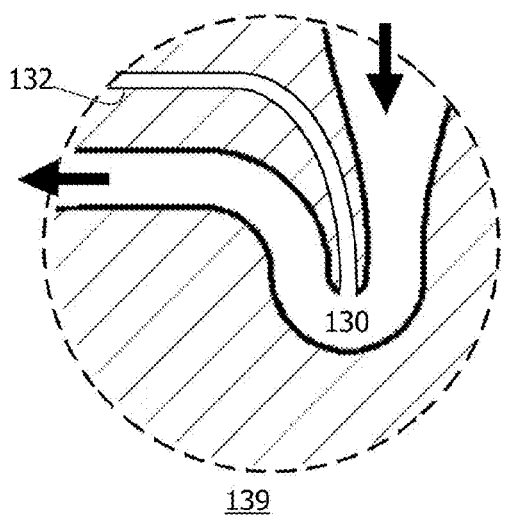
Figure 9D:
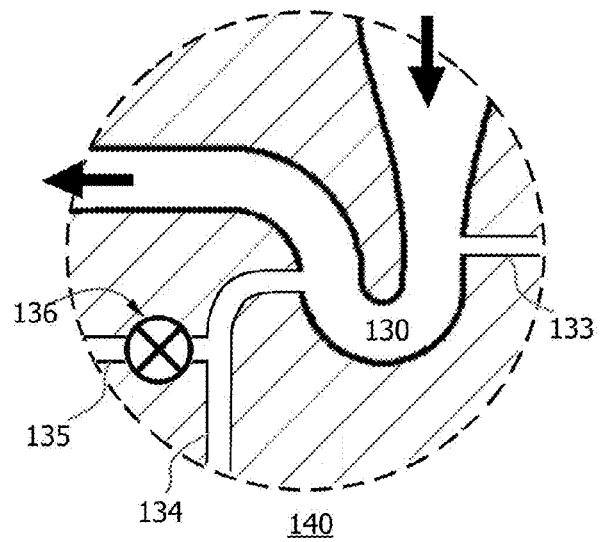

In FIG. 9A, modifications of a centrifugal "particle trap" are shown. The detail (dashed circle) highlights the centrifugal impactor surface or "trap" (130), which is formed of a concavoconvex bend in the collector channel, the concavoconvex bend of the channel having a windward wall and a leeward wall. As gas streamlines break away from the linear direction of flow and follow the leeward wall, particles with more momentum collide with the windward wall in the bend. Particles captured in the trap 130 are eluted for analysis by injecting a liquid reagent into the collector channel. As can be seen in FIGS. 9B-9D, where the detailed view area selected in FIG. 9A (dashed circle) is magnified in three embodiments of the invention (138,139,140) these embodiments also include at least one microfluidic duct (131,132,133,134,135) for injection or collection of a liquid reagent. The ducts are generally in fluidic connection with a pump functionality or member for pumping a sample or a reagent, and optionally in fluidic connection with a reservoir (not shown) for dispensing a reagent or receiving a sample. The duct can serve as a common duct for injection of one or more reagents, and the pumping means can be configured to provide reversible pumping so that the liquid sample can be withdrawn from the trap 130 after the captured aerosol material trapped therein is suspended or solubilized. Alternatively, as previously noted, a liquid reagent is used to resuspend or solubilize the aerosol, and if desired the sample is then analyzed in situ in the trap. In FIG. 9B, an embodiment 138 with optical or acoustic window 137 or light pipe is shown. The optical window or light pipe is used to examine the liquid contents of the eluted aerosol sample in place in the trap 130. Waveguides mounted centrally in a microfluidic channel in communication with the liquid sample may also be used for in situ analysis, as has been described in U.S. Pat. Nos. 6,082,185 and 6,136,611. In FIG. 9D, an embodiment 140 with three microfluidic ducts (133, 134,135) is shown. One duct serves as an injection duct, one as a sampling duct, and another for introducing at least one reagent. Alternatively, fluid or air can be introduced in two ducts, for example 133,134, so as to alternate the direction of motion of a microdroplet or droplets in the trap 130. By injecting trains of droplets separated by pulses of air from another duct, an interface between the droplets is created that facilitates mixing and plug flow. Branched duct 135 may also be used so that multiple fluids can be added stepwise, as in performing an assay, and the ducts can be valved 136 as desired.

In another aspect, a liquid dispensed by the microvolume pump means is itself the inertial impactor surface. In this configuration, a low melt glassy matrix is deposited on the surface of the inertial impactor. A glass soluble in a liquid is chosen for the matrix. Once aerosol particles are collected, the glass layer is dissolved in a liquid is then transferred to a microfluidic circuit for processing downstream in an analytical module, which may be integrated or separate from the collector body.

Figure 10A:
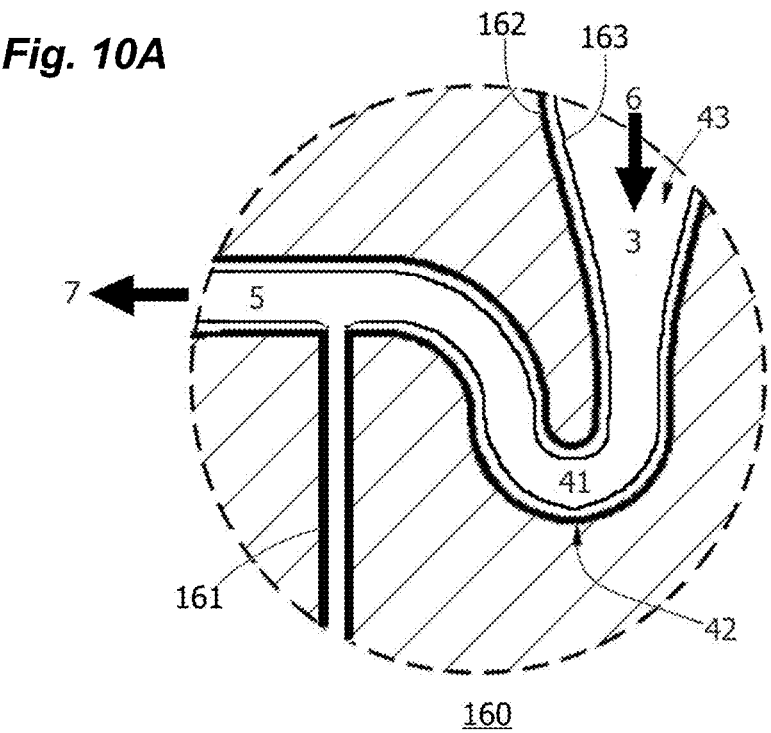
FIG. 10A shows a particle trap impactor configured with a injector/sampling duct and a sacrificial substrate overlayer lining the collector channel.
Figure 10B:
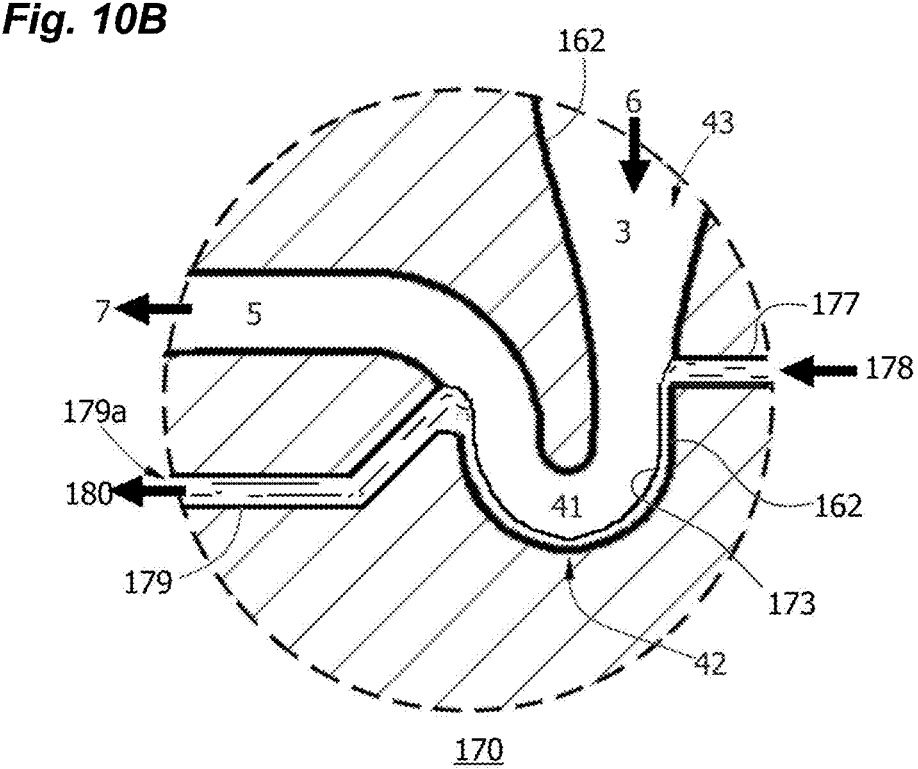
FIG. 10B shows a centrifugal-impactor particle trap configured with tandem injector and sampling ducts and having a regenerated sacrificial substrate overlayer lining the trap.

FIGS. 10A and 10B describe embodiments (160, 170) in which the impactor surface 16, of a centrifugal impactor 15, is coated with a glassy matrix material prior to collection. In FIG. 10A, the collector channel 43 has an inside undersurface 162 and the inside surface is coated with an overlayer 163, termed herein a "sacrificial substrate overlayer" because the layer is intended dissolve on exposure to an elution agent, thus aiding in the elution of aerosol material captured its surface. As before, a gas stream 6 with particle concentrate moves through the collector from receiving arm 3 to outlet arm 5 and is depleted 7 of aerosol particles in trap 15 according to the cut-off characteristics of the impactor. Elution fluid is injected through injection duct 161 and is directed onto the impactor surface 42 of the trap 41, where the sacrificial substrate overlayer 163 and any particulate material trapped on the overlayer is dissolved. The concentrated liquid sample or "eluate" thus prepared may be further reacted in situ and analyzed or may be conveyed to a sampling port for downstream or remote analysis.

In FIG. 10B, collector channel 43 has an inside undersurface 162 and within the trap 41 the inside surface 162 is coated with an overlayer 173, termed herein a "sacrificial substrate overlayer" because the layer is intended dissolve on exposure to an elution agent, thus aiding in the elution of aerosol material captured its surface. As before, a gas stream 6 moves through the collector from receiving arm 3 to outlet arm 5 and is depleted 7 of aerosol particles in trap 41 according to the cut-off characteristics of the impactor. In this illustration, the sacrificial substrate overlayer 173 is injected as a glassy melt 178 above the $T_m$ for the substrate through a reagent injection duct 177 and is directed onto the impactor surface 42 of the trap 41 where it may be allowed to harden and subsequently, after particle loading, be remelted for collection via sampling duct 179. The sacrificial overlayer 173 thus can serve as an elution reagent. Or a continuous flow process is envisaged in which the liquid reagent 178 is continuously injected into the trap at injection port 177 and continuously withdrawn as a particulate concentrate 180 at sampling port 179a. By controlling the rate of flow of the liquid reagent, the concentration of particulate in the sample can be raised or lowered. The liquid sample or "eluate" thus prepared may be further reacted in situ and analyzed or may be conveyed to a sampling port for downstream or remote analysis. Various combinations of the embodiments 160 and 170 are also envisaged.

Figure 11A:
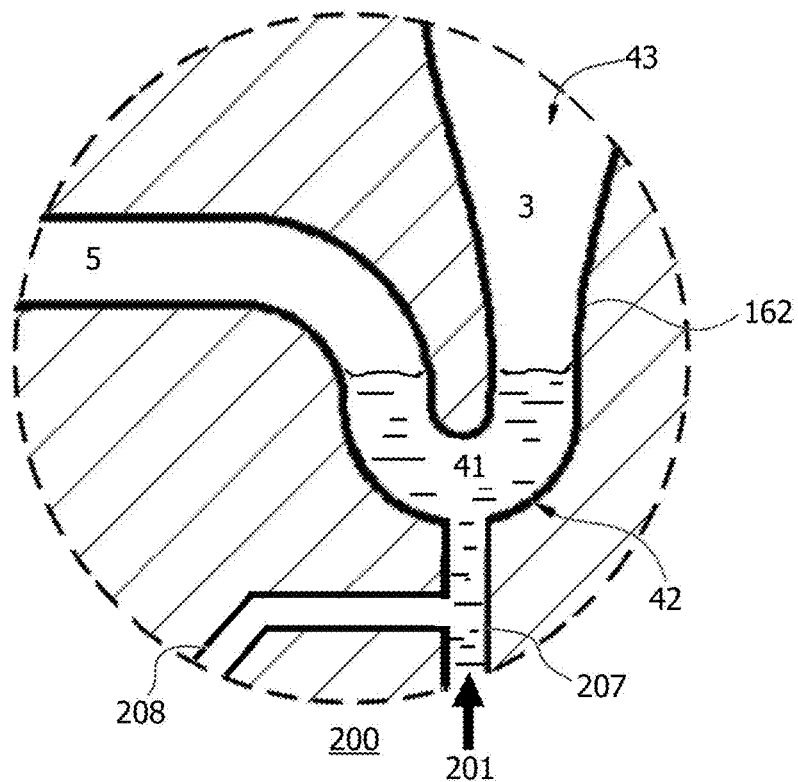
FIGS. 11A and 11B show a two-part diagram of a method for preparing a centrifugal-impactor particle trap with sacrificial substrate overlayer lining the trap.
Figure 11B:
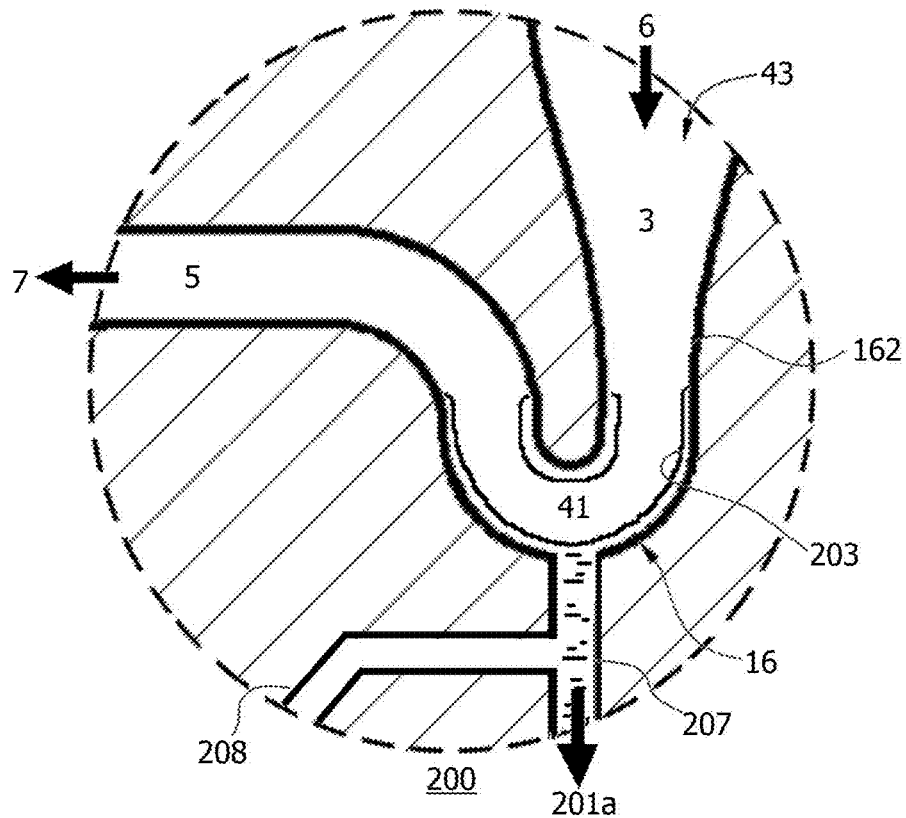

In FIGS. 11A and 11B, a process for regenerating a glassy sacrificial substrate overlayer is described. The glassy matrix 201 is an amorphous solid when solidified and a liquid when melted. Liquid glass is first injected via warmed injection duct 207 to fill the lower bending portion of the trap 41 (FIG. 11A). The lake of material then drained as shown in FIG. 11B, leaving a thin overlayer 203 lining the inside undersurface 162 of the collector channel 43.

As before, a particle concentrate in a gas stream 6 moves through the collector from receiving arm 3 to outlet arm 5 and is depleted 7 of aerosol particles in centrifugal impactor trap 41 according to the cut-off characteristics of the impactor. An elution fluid may then be injected via injection duct 208 and the sacrificial substrate overcoat 203 is dissolved or melted into the liquid sample, eluting with it essentially all of the captured aerosol material and airborne agents, if any.

Alternatively, glass layer 163,173,203 may be coated on a "primer" layer of a hydrophobic or fluorophilic substance such as a silane, parylene, or perfluorocarbon lining the collector channel so that upon dilution with an aqueous reagent, the eluate beads up as a microdroplet. In this case, binders are used that improve the adherence of the glass to the underlying primer.

In another aspect, the glass layer 163,173,203 contains dry reagents such as enzymes or chromogens for treating or analyzing the liquid sample when hydrated or dissolved. Some biological reagents such as enzymes are advantageously stabilized during storage by a glass matrix as described here.

Microelution with Soluble Glass Sacrificial Substrate Overlayer

Sacrificial glass substrate overlayers on the inside of the particle trap impactor surface or surfaces is advantageous for microelution of captured particles. Basic formulations for use as glass sacrificial overlayers are now discussed and are applicable to all classes of particle traps. The sacrificial substrate layer is preferably a glass, having a $T_g$ and a $T_m$ in the range of 0 to 200° C., more preferably melting at 10 to 20° C. above a setpoint. Glasses, including arabinose, erythritol, fructose, galactose, glucose, lactose, maltitol, maltose, maltotriose, mannitol, mannobiose, mannose, ribose, sorbitol, sucrose, trehalose, xylitol, xylose, dextran, or a mixture thereof, formed as an amorphous glass, are suitable. Other glasses may also be suitable and the above list is not intended to be limiting. For example, lactic acid and capric acid are candidate glasses when used with a suitable eluant. In some cases, eutectic mixtures are used to lower the melting temperature as desired. Optionally, mixtures formed of one or more of the above glass-formers and a plasticizer are prepared so as to adjust the melting temperature and the viscosity as desired. Plasticizers may include but are not limited to glycerol, dimethylsulfoxide, lower molecular weight poly-ethyleneglycol, ethylene glycol, propylene glycol, diethylene glycol dimethylether, triethylene glycol dimethyl ether, tetraethylene glycol dimethyl ether, N,N-dimethylacetamide, N,N-dimethylformamide, tetramethylurea, water, or a mixture thereof. Plasticizers also serve to prevent formation of any crystalline domains if necessary. Binders are used to strengthen the glass, which must resist the forces associated with the gas stream, and to aid in adhesion of the glass sacrificial layer (163,173, 203; see also FIGS. 16-18) to the collector body undersurface (162). Suitable binders include but are not limited to polyvinylpyrrolidinone, higher molecular weight poly-ethyleneglycol, a block copolymer of poly-propyleneglycol and poly-ethyleneglycol, polyacrylate, poly-methylmethacrylate, poly-(d,l-lactide-co-glycolide), triethylene glycol dimethyl ether, butyl diglyme, chitosan, a cellulose, methylcellulose, an alginate, an albumin, or a dextran. Less useful are relatively insoluble binders such as starch and gelatin. Thus the sacrificial substrate overlayer can consist of a glass or a glassy matrix comprising a mixture of a glass with a plasticizer or a binder, or a glass with a plasticizer and a binder. A suitable solvent is used to dissolve the sacrificial layer, thereby releasing any captured aerosol particles resident thereon. Heat may be used to facilitate melting of the glass.

Prior art teachings teach away from formulations of this nature. Various modifications of the inertial impactor surface, such as described in U.S. Pat. No. 4,452,068 and use of greases such as described by Marple in U.S. Pat. No. 4,321, 822, and in U.S. Pat. Nos. 4,764,186, 4,827,779 and 5,693, 895 have been proposed as means to reduce elastic collisions which result in retrainment of aerosol particles in the gas flow and losses from the impactor surface. U.S. Pat. No. 6,363,800 to Call forming a coating on the impactor surface with parylene (a hydrophobic polymer) or tetraglyme (a polyol) for enhancing capture of aerosols, but do not teach use of a substrate layer which is substantially eroded and dissolved in the elution fluid. Ta Won Han of Rutgers Univ has proposed using Lotusan®, a superhydrophobic paint (see U.S. Pat. No. 6,660,363), to improve aerosol elution efficiency from inertial impactors, but has not, to our knowledge, reported success with bacteria. Thus the prior art teaches hydrophobic or sticky surfaces, but does not teach erodible sacrificial surface layers to improve elution efficiency from inertial impactor surfaces. Also not disclosed are surfaces that are solubilized by melting or by a combination of melting and addition of a solubilizing reagent or diluent.

Figure 12:
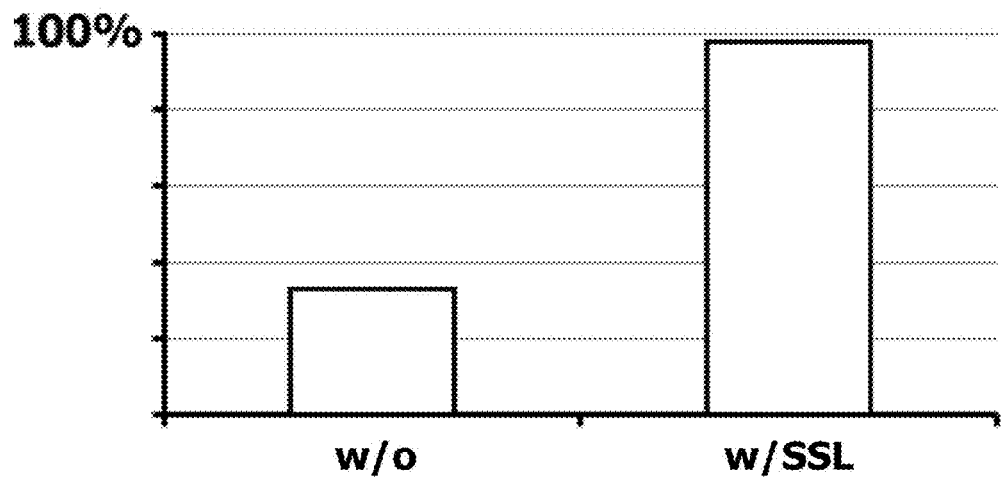
FIG. 12 illustrates improvement in bacterial elution efficiency for *E. coli* using a sacrificial substrate overlayer.

FIG. 12 shows how a sacrificial substrate overlayer improves elution efficiency of *Escherichia coli* B impacted on an inertial surface. Elution of *E. coli* is surprisingly successful using this approach in spite of the disruptive shearing impaction and its effect on gram negative bacteria. Elution efficiencies of *E. coli* from untreated impactor surfaces are in some instances less than 35% in aqueous solutions. Happily, upon use of a sacrificial substrate overlayer, we have discovered that elution efficiency increases to essentially 100% (column labeled "w/SSL" on plot), a surprising finding and a contribution that makes a distinct technological advance. For example, 80% trehalose with 10% glycerol and 10% polyvinylpyrrolidinone in aqueous ethanol may be applied as a thin layer within a trap in a plastic collector body. By application of this technique, elution in liquid sample microvolumes is achieved for a gram negative rod, but the technique is applicable to a variety of bioaerosols and particulate toxins, including spores and virus particles, and for example bioagents trapped in a mucous matrix, which are typically adherent to impactor surfaces and difficult to elute. Similar results are also obtained with bluff body impactors and electrostatic precipitators modified with a sacrificial substrate overlayer, as will be described below.

Bluff Body Inertial Impactors

Figure 13:
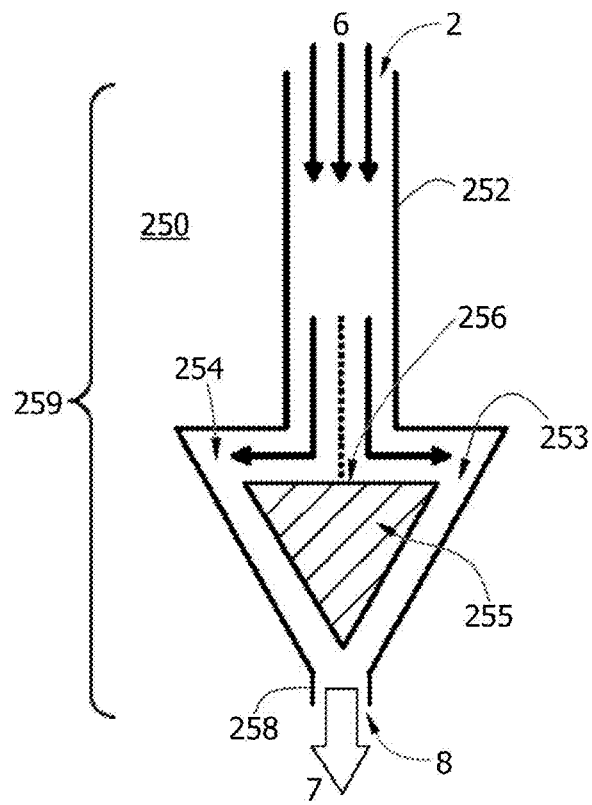
FIG. 13 is a schematic representation of a collector channel with bluff body impactor.

We now turn to bluff body impactors. The design of a collector module is not limited to the bending channel geometry of a centrifugal impactor. The collector module may employ a bluff body with a windward surface facing a gas stream in a collector channel such that the gas flow streamlines are deflected but particles impact on the surface of the bluff body. A schematic of a bluff body impactor 250 is shown in FIG. 13. This class of impactors includes cascade impactors and liquid impingers. Micro droplet elution as described below is readily adapted to various members of the class.

In FIG. 13 we see the gas stream 6 in a receiving arm 252 of a collector channel is divided and flowing in lateral channels to the left and right (253,254) of a central bluff body 255. The windward surface (in this case the uppermost surface) of the bluff body is the impactor surface 256. Aerosol particles (dashed line) are impacted by inertia on the impactor surface 256. A particle depleted exhaust 7 exits the bluff body impactor 250 at an outlet arm 258 of the collector.

The dimensions of the collector and bluff body impactor are characteristically microfluidic or near-microfluidic dimensions. The dimensions of the bluff body impactor surface, also sometimes termed a "micro fluidic particle trap", are such that at least one cross-sectional dimension of the collector microchannel and impactor surface is generally smaller than 1500 microns. The collection volume of elution reagent applied to the windward impactor surface is generally less than 10 microliters and preferably less than 1 microliter, and is sometimes only a few nanoliters to a few hundred nanoliters. Microfluidic pumps and valves as previously described for centrifugal impactors may be used to form bluff body impactors interfacing with microfluidic circuits.

The bluff body impactor can be assembled within a channel fabricated (etched, milled, or molded) on a surface and sealed by another mating surface, or fabricated as a monolithic solid using 3D photolithography.

Figure 14A:
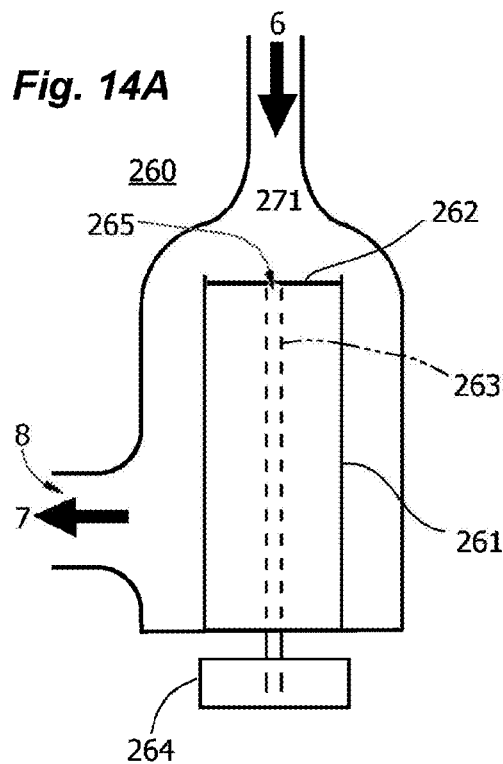
FIGS. 14A and 14B show collection and elution of aerosol particles from a bluff body-type particle trap.
Figure 14B:
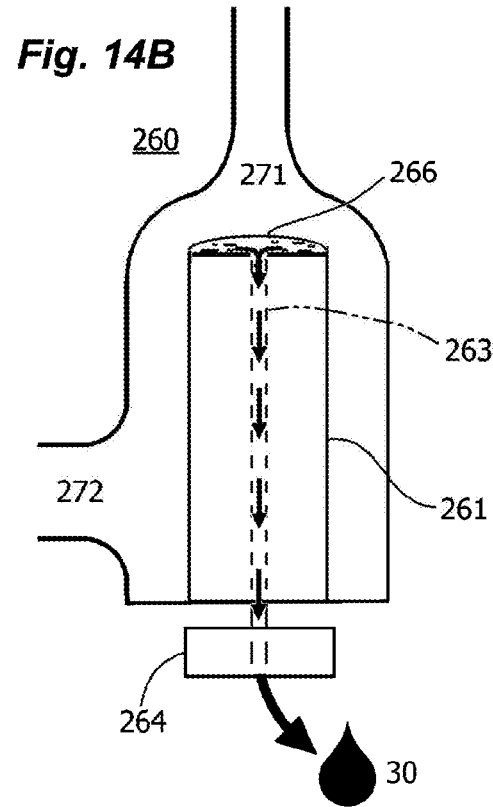

In another aspect of the invention, as shown in FIGS. 14A and 14B, a three-dimensional bluff body impactor 260 is shown. The central bluff body member 261 is a freestanding pillar or supporting column, the head of which is an inertial impactor surface 262. The column 261 is provided with an internal first microfluidic channel 263 in fluid communication with the impactor surface 262 via injection port 265 and with a pumping means 264 and fluid reservoir (not shown). A gas stream 6 entering the receiving arm 271 of the collector 260 is depleted of aerosol particles by impaction on bluff body impactor surface 262 and exits the collector at outlet arm 272 as a depleted gas stream 7. When a useful mass of aerosol particles are collected on the impactor surface 262, the first microfluidic channel is used to dispense a liquid reagent 266 onto the impactor surface. As shown in FIG. 14B, any eluted particulate material is then collected by withdrawing the fluid back through the first microfluidic duct 263. Liquid sample 30 is collected at a sampling port, although it should be understood that the invention is not limited to this option and that in situ analytical techniques are also contemplated. Aerosol particle suspensions or solutions obtained in this way can be highly concentrated in a very small volume of a liquid reagent.

Pump functionality 264 is for example a small syringe pump and is capable of switching direction of flow. A bidirectional pump means is useful both for wetting the impactor to elute captured aerosol particles and for withdrawing the liquid sample containing the aerosol particle suspension or solution for further analysis. Other pump utilities as described earlier may also be used.

Figure 15A:
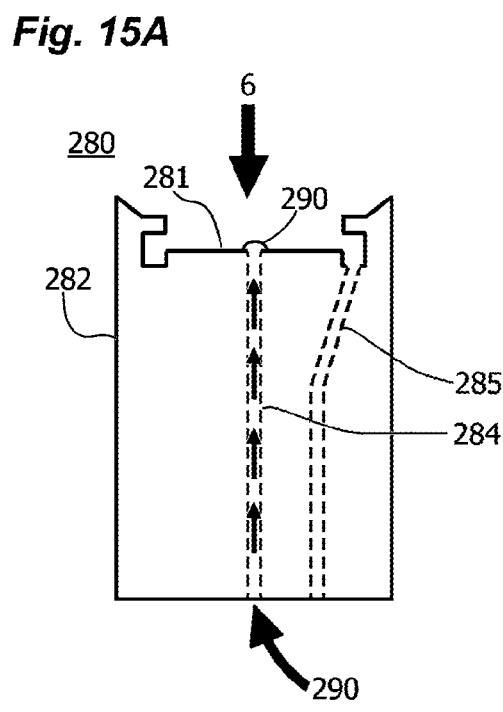
FIGS. 15A and 15B represent an alternative bluff body embodiment using tandem microfluidic ducts.
Figure 15B:
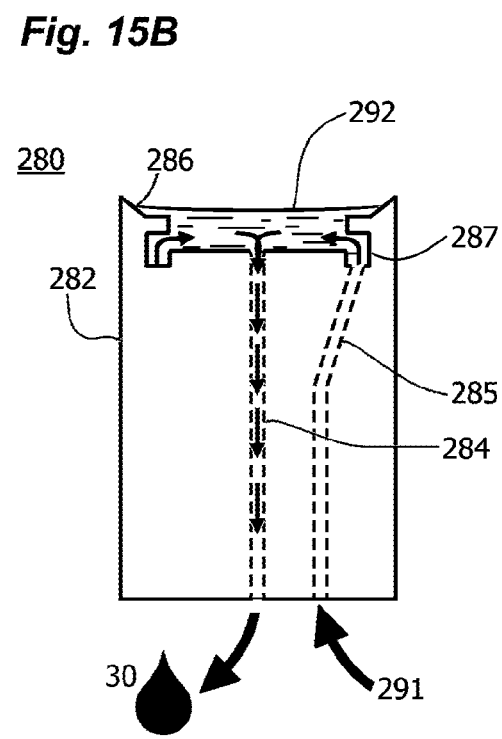

In FIGS. 15A and 15B, a related bluff body impactor 280 having two microfluidic channels in a cylindrical support pillar or column 282 is shown. As before, aerosol particles are captured by impaction from a gas stream 6; impacted aerosol particles collect on impactor surface 281, and elution fluid 290 is injected onto the impactor surface via injection duct 284. The liquid sample is pre-processed (FIG. 15B) by adding analytical pre-processing reagent 291 via microfluidic duct 285, the reaction mixture 292 filling moat 287 and held in place by dike 286. The liquid sample is optionally withdrawn through microfluidic sampling duct 284 if desired. In a related embodiment, the second channel 285 is used to periodically add a detection reagent 291 such as a chromogen, antibody, or a substrate of an enzyme which reacts with a particular species of aerosol particle if present on the impactor. Using this apparatus, an ELISA assay may be run in situ on entrapped particles, for example. Liquid samples 30 positive by ELISA are then drawn off for further analysis.

Figure 16A:
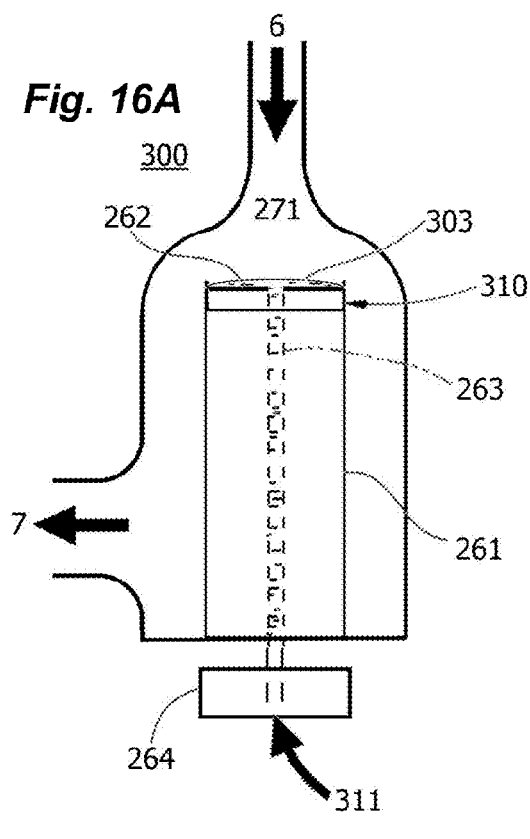
FIGS. 16A and 16B show collection and elution of aerosol particles from a bluff body-type particle trap, the bluff body having a sacrificial substrate overlayer.
Figure 16B:
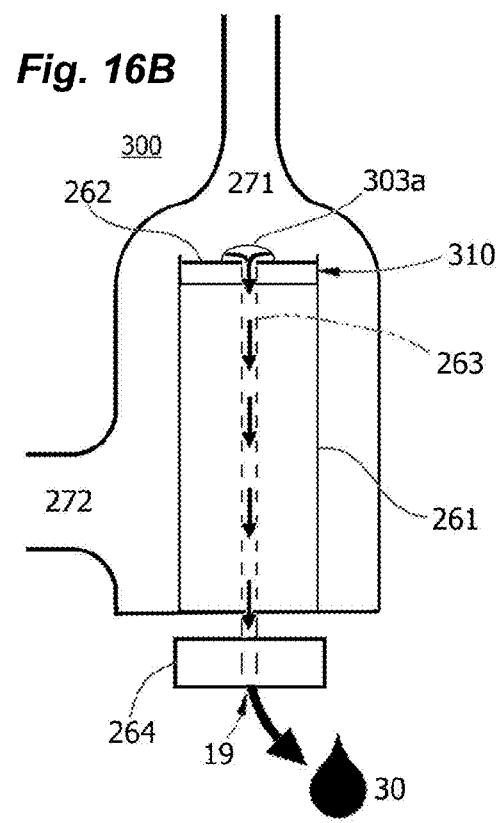

According to another aspect of the invention, as shown in FIGS. 16A and 16B, a three-dimensional bluff body impactor 300 is shown. The center bluff body 261 is a freestanding pillar or supporting column, the head of which 262 is coated with a sacrificial substrate overlayer 303 (the thickness is exaggerated for clarity), the surface of the glass layer 303 forming the inertial impactor surface. The bluff body impactor support column 261 is provided with an internal microfluidic channel 263 in fluid communication with the impactor surface 262 and with a pumping means 264 and fluid reservoir (not shown). A gas stream 6 entering the receiving arm 271 of the collector 300 is depleted of aerosol particles by impaction on bluff body impactor glass surface 303 and exits the collector at outlet arm 272 as a depleted gas stream 7. When a useful mass of aerosol particles are collected on the glass layer 303, resistive heating element 310 mounted in the head is used to melt the glass. Hot liquid reagent 311 is then pumped onto the impactor surface where it dissolves the glass layer 303. As shown in FIG. 16B, the melted glass 303a containing eluted aerosol particles is then withdrawn via microfluidic duct 263 and reversible pump 264, and is collected as liquid sample 30. The liquid sample can be conveyed to an external analytical station or can be analyzed in place.

In a variant of this embodiment, a glassy matrix layer on the impactor surface forms a sacrificial substrate overlayer 303 on the windward surface of the impactor 262, so that particles colliding with the impactor directly contact and adhere to the glass layer. The sacrificial substrate overlayer 303 is injected as a liquid melt onto the impactor surface through microfluidic duct 304 and hardened in place. A resistive heating element 310 is used to melt the glass, which has a low $T_m$. As shown in FIG. 16B, the liquid sample 30 (ie. the melted glass 303a) is then withdrawn from the impactor surface through microfluidic duct 263 for downstream analysis. Thus the glass is both impactor surface and elution reagent.

In another aspect, the glass 303 contains dry reagents such as enzymes or chromogens for treating or analyzing the liquid sample when hydrated or dissolved.

Figure 17:
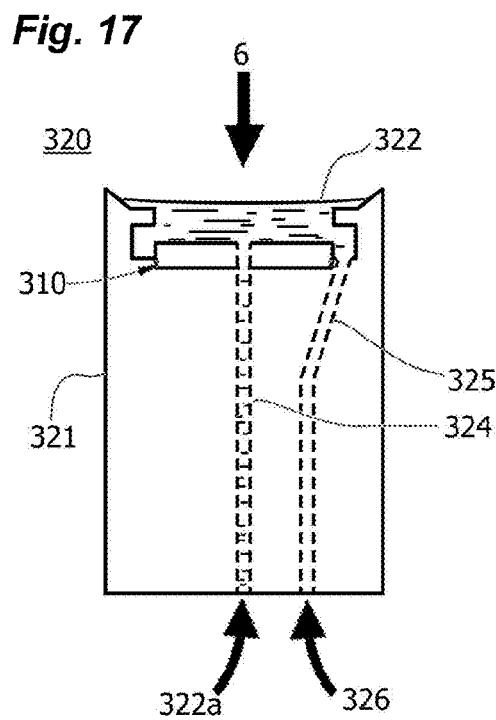
FIG. 17 shows a modified bluff body member with sacrificial substrate overlayer on the impactor surface and embedded heating element.

More complex variants are envisaged, as shown in FIG. 17. Impactor resistive heating element 310 may be combined with bluff body impactor support member 321. An impactor surface formed of a sacrificial glass layer 322 is cast in place by injection of the low melt glass as a liquid 322a through warmed micro fluidic duct 324 onto the windward surface of the impactor body 320 and allowed to harden in place. After collection of a suitable mass of aerosol particles from impinging gas stream 6, the solid glass 322 is melted by applying a current to resistive heating element 310 (circuit not shown) and is withdrawn through microfluidic duct 324. Liquid reagent 326 injected through a second microfluidic duct 325 is used to facilitate rinsing of the glass from the injector surface. A glass coated impactor surface of this sort can be regenerated for a subsequent cycle. Thus this embodiment 320 may be used in a regenerative cycle.

According to another embodiment of the invention, the glassy matrix 322 is held above its melting point during particle impaction, providing a viscous, sticky, but readily soluble material for capturing particles in an inertial impactor. The molten glassy matrix 322 is stable to a high velocity gas stream and resists evaporation, unlike aqueous reagents conventionally used in liquid impingers.

Figure 18:
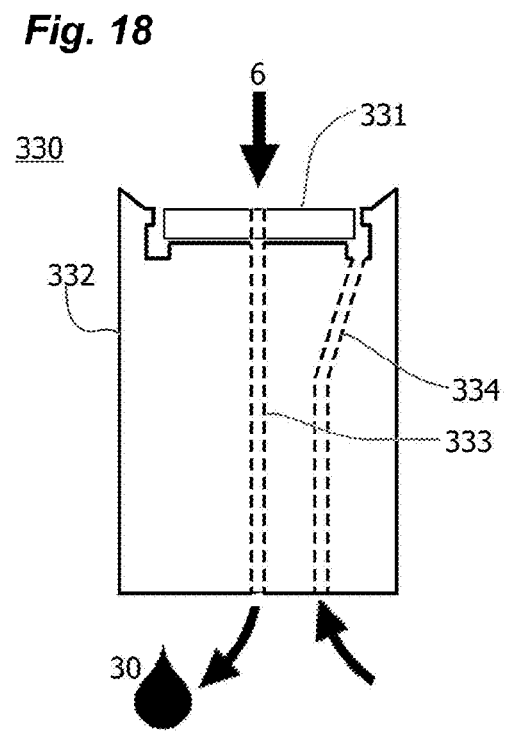
FIG. 18 shows a bluff body member with impactor surface modifications for processing and treating an aerosol sample.

As shown in FIG. 18, the impactor cap element 331 forming the impactor surface on top of bluff body pillar member 332 may a) contain a piezoelectric crystal for ultrasonic treatment of the collected sample; may b) contain microelectrodes for electrowetting and electropumping of microdroplets on the impactor surface; may c) contain MEMS components such as an inkjet printer head for injecting a liquid reagent; may d) contain a flat plate capacitor or an electrode, such as would be used in an electroprecipitator, for example. As before, any aerosol particles are first collected by inertial impaction from gas stream 6. Following collection, reagents may be injected via microfluidic ducts 333 and 334 and a liquid sample 30 eluted. Chemical, physical or biological treatments may be applied directly to the liquid sample. The liquid sample may be withdrawn from the impactor cap surface 331 if desired, or an analysis may performed on the surface in situ. Thus, bluff body impactor assembly 330 is an active component with capabilities for aerosol pre-processing, sample micro fluidics, and for instrumental in situ analysis in an integrated package.

Referring again to FIG. 18, in another embodiment, the cap element 331 of the pillar member 332 may be modified using microassembly or MEMS techniques. In one case, the cap surface is a specially fabricated electrode coated on its upper aspect with a silane layer and used to reversibly adhere a liquid droplet to the impactor by electrowetting. When voltage is removed, the liquid/surface interaction becomes hydrophobic and the contact angle becomes negative, facilitating withdrawal of the full microvolume. The microdroplet can be moved from side to side and across the surface of the silane layer using pairs of electrodes as described by Pamula in U.S. Pat. No. 6,911,132. As employed in the present invention, this technology is used to harvest aerosol particles from the surface of the impactor. Wiring and circuit elements are not shown, but are readily accommodated within a silicon chip supported on the pillar 332 with associated leads extending down the pillar to a power supply.

The invention should not be construed as limited only to the depicted configurations, and includes various combinations of the elements configured for particle elution in a microvolume from any centrifugal or bluff body impactor. Bluff body impactors as know in the art are not limited to pillar elements with top-mounted impactor plates, but may also be side mounted impactors adapted from those described in U.S. Pat. Nos. 4,321,822, 6,110,247, and others as would be known to those skilled in the art.

Electrostatic Precipitators

Electrostatic interactions are particularly effective in entraining sub-micron particles, which may be captured in a particle trap formed, for example, by mounting a pair of charged plates so that a gas stream flowing between the plates is exposed to an imposed electrostatic field, one plate having a positive charge and the other a negative charge. The plates are used to trap charged aerosol particles. Particles may be natively charged or may acquire induced charge by contact with a source of ions, such sources including but not limited to a "corona wire," a source of ionizing radiation, and a radio-frequency discharge. Ionization may be achieved, for example, by a plasma discharge from a corona array disposed in the path of the gas stream.

Figure 19:
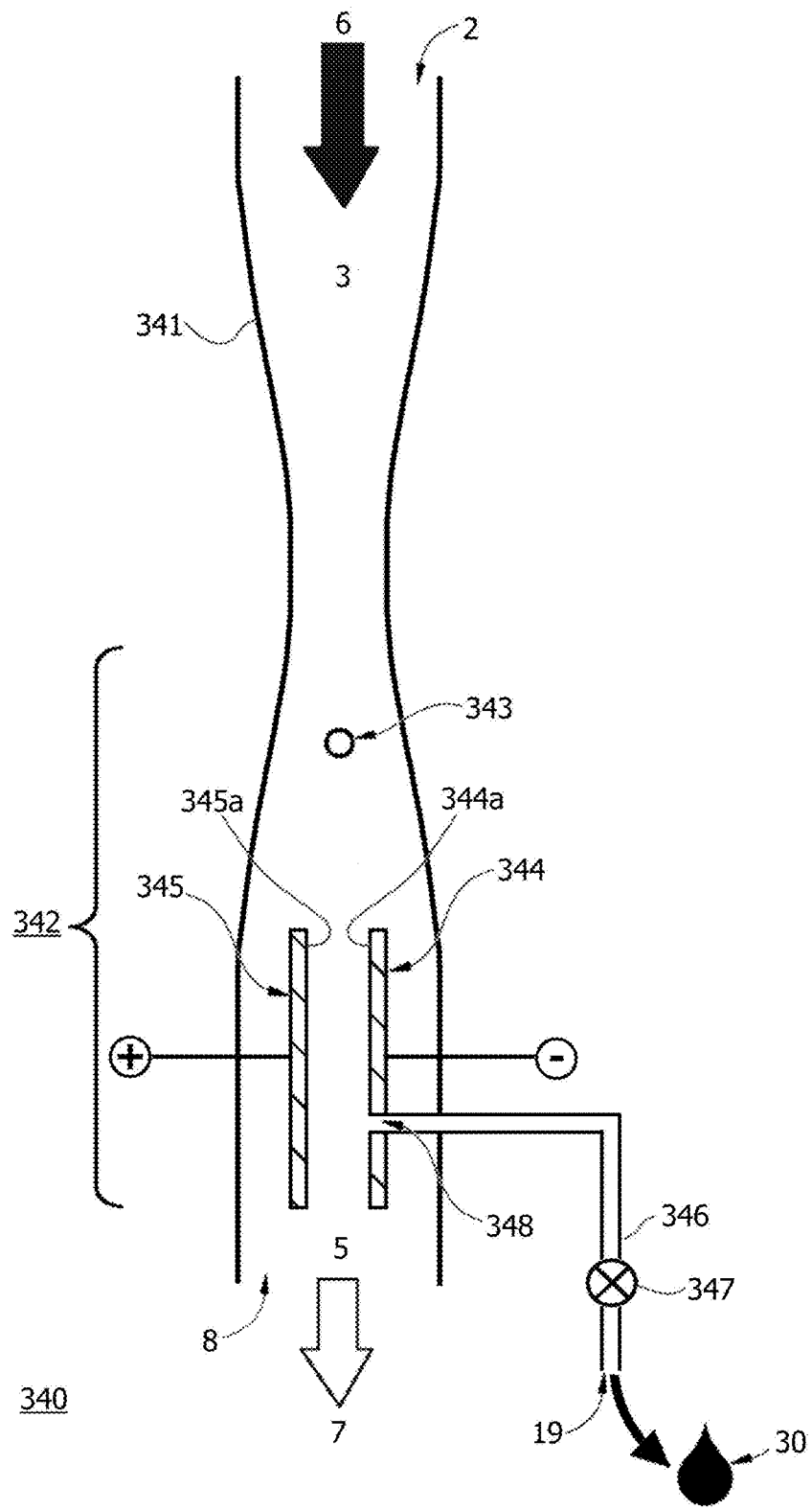
FIG. 19 is a schematic of a collector module with electrostatic particle trap.

A schematic of an electrostatic collector module 340 is shown in FIG. 19. Collector channel 341 is configured for receiving a gas stream 6 in receiving arm 3 via intake orifice 2. The gas stream and entrained particles are ionized by contact with corona wire 343. A pair of charged plates 344, 345 trap oppositely charged particles. Particle depleted gas stream 7 exits the collector module via outlet arm 3 and outlet orifice 8. Corona wire 343 and the inside surfaces 344a, 345a of the pair of charged separation plates make up electrostatic particle trap 342. Microfluidic injection duct 346 with injection port 348 and optional valve 347 is used to inject a microdroplet volume of an elution fluid and to withdraw a liquid sample 30 at sampling port 19.

The dimensions of the collector channel and electrostatic precipitator are characteristically microfluidic or near-micro fluidic dimensions. The dimensions of the electrostatic particle trap, are such that at least one cross-sectional dimension of the collector channel and impactor surface is generally smaller than 1500 microns. The collection volume of elution reagent applied to the plate surfaces is preferably less than 10 microliters and preferably less than 1 microliter, and is sometimes only a few nanoliters to a few hundred nanoliters. Microfluidic pumps and valves as previously described for centrifugal and bluff body impactors may be used to form electrostatic precipitator interfacing with microfluidic circuits.

Figure 20:
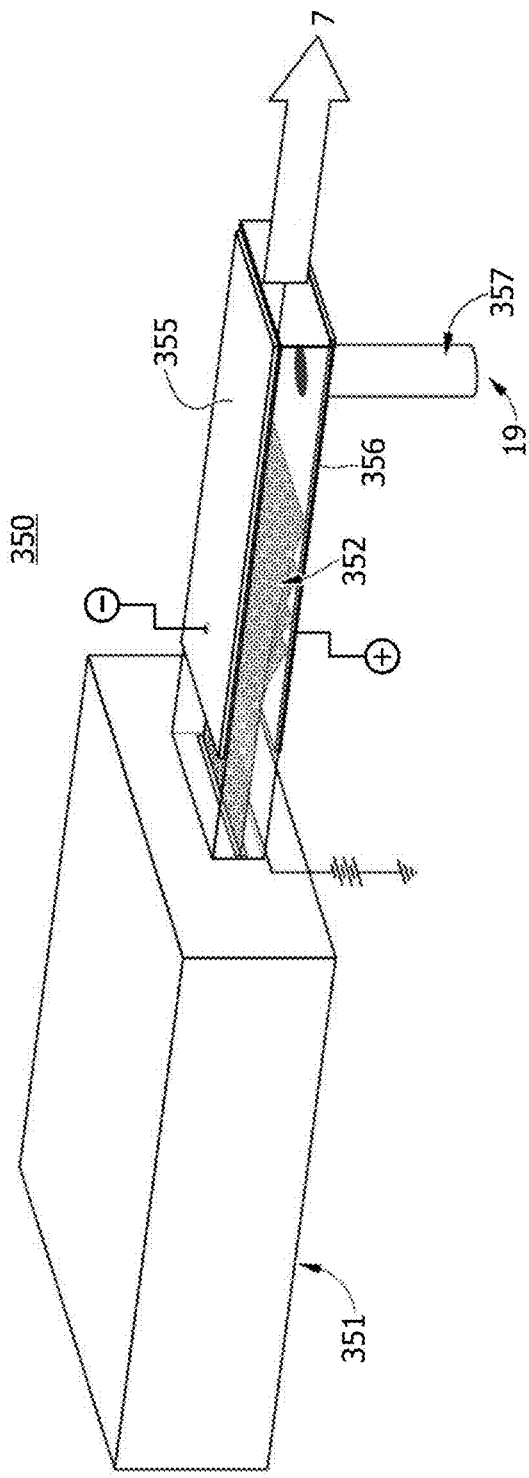
FIGS. 20A and 20B illustrate operation of an electrostatic particle trap.

FIGS. 20A and 20B depict a second electrostatic precipitator. A gas stream is received and ionized in front collector body member 351 and passed between charged plates 355 and 356. Charged particles 352 (dots) are captured electrostatically by oppositely charged plate 356, marked here as positively charged (+). Depleted gas stream 7 exits the module to the right. In FIG. 20B, a detail of the elution process is shown. Captured particles (dots) blanket the upper surface 358 of plate 356. A fluid volume 359 (shown with convex menisci) fills the space between plates 356 and 355. Microfluidic injection duct 357 is used to inject the fluid and to collect eluted particles in a liquid sample at a sampling port. A sacrificial glass overlayer may be used on the charge separation plates as a thin dielectric layer to improve elution efficiency as previously described for inertial impactors.

Integrated Devices

The technical advantage achieved by reducing a dimension of the collector channel and particle trap to microfluidic or near-microfluidic dimensions on the order of 1500 microns or less is that a very small volume of fluid reagent can be used to collect and process the aerosol particles, or constituents thereof, captured on the impactor surface—generally a discrete microvolume of 10,000 nanoliters or less, more preferably a microvolume of less than 1000 nanoliters—resulting in a very high concentration factor and improved analytical sensitivity. While it would initially appear that collector channels of this diminutive size would be undesirable because of limitations on the throughput flow rate that can be achieved at sub-sonic gas stream velocities, surprisingly, by coupling the impactors of the present invention with upstream aerosol concentrators or arrays such as those of co-assigned US Pat. Appl. Doc. No. 2008/0022853, overall processing throughputs of 10, 20 or even 25000 L/min are readily achieved at sub-sonic gas jet velocities in the coupled concentrator/collector apparatus because only the particle-enriched minor flow from the aerodynamic concentrator is routed through the collector. This combination happily was found to quickly reduce the aerosol mass found in a cubic meter of air or more to a nanoliter volume of liquid sample 30 in less than a minute. The collectors of the present invention thus serve as aerosol-to-liquid conversion modules with microfluidic or near-micro fluidic dimensions.

By resuspended captured particles in nanoliter-sized droplets, potentially up to a $3 \times 10^9$-fold concentration factor over particle density in the ambient air sample may be achieved. Actual results to date in prototypes have achieved a $5 \times 10^6$-fold concentration of microbial cells trapped on the particle trap impactor surfaces of the present invention and eluted in a liquid droplet volume of 500 nanoliters.

To achieve this synergy, the collectors of the present invention may be used in combination with aerosol concentrators such as a virtual impactor, aerodynamic lens (ADL), skimmer, venturi, nozzle, or other type of concentrator. Typically, ADLs are used in combination with skimmers and the collector would be sealedly fitted to the minor flow outlet of the skimmer. For a description of the art, the reader is referred to co-pending US Pat. Appl. Doc. Nos. 2008/0022853, U.S. patent application Ser. No. 12/125,458, and to the works of Marple and others (cf. Chen, B T and H C Yeh (1985) A Novel Virtual Impactor: Calibration and Use, J Aerosol Sci 16: 343-354; in Novick V S and J L Alvarez (1987) Design of a multi-stage virtual impactor, Aerosol Sci Tech 6:63-70; in Loo B W and C P Cork (1988) Development of high efficiency virtual impactors, Aeros Sci Techn 9:167-176; in Marple V A et al (1980) Virtual Impactors: a theoretical study, Environ Sci Tech 14:976; and in Goo, J (2002) Numerical simulation of aerosol concentration at atmospheric pressure by a cascade of aerodynamic slit lenses, J Aerosol Sci 33:1493-1507) and to a representative selection of virtual impactor designs found in U.S. Pat. Nos. 3,901,798, 4,301,002, 4,670,135, 4,767,524, 5,425,802, 5,533,406, 5,788,741, 6,062,392, 6,386,015, and 6,402,817.

Figure 21:
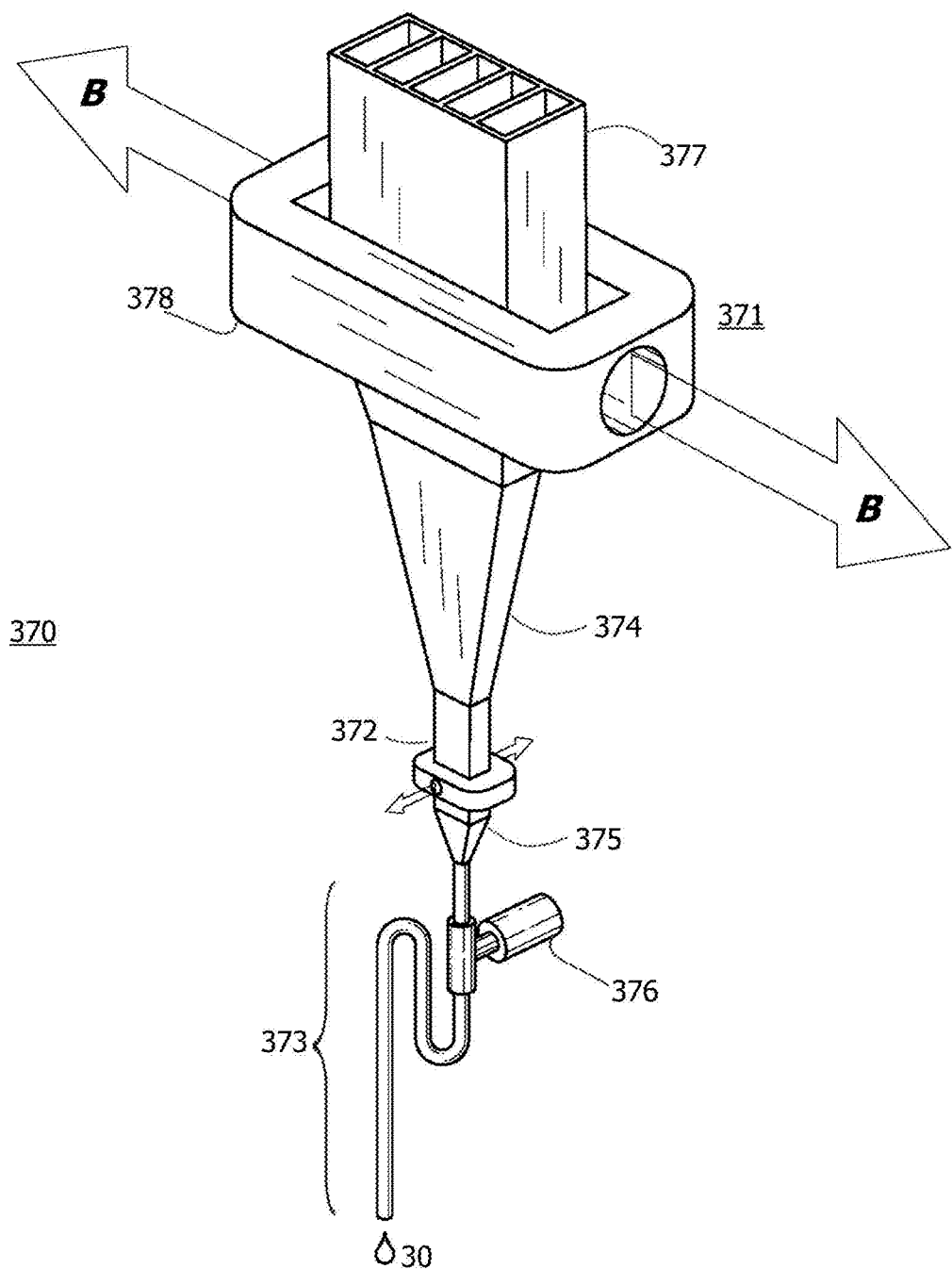
FIG. 21 is a schematic view of an integrated aerodynamic lens (ADL) with skimmer and centrifugal impactor. The ADL is a multistage aerosol concentrator.

As shown in FIG. 21, an aerosol concentrator module 371 in combination with an aerosol collector module 373 of the present invention is depicted. Combination 370 of a two-stage ADL array, with first skimmer, first stage adaptor 374, second ADL and skimmer 372, second stage adaptor 375, and centrifugal aerosol collector 373 is illustrated. Also shown is a pump functionality or member (376) with tee for injecting a liquid reagent and for eluting particles deposited in the particle trap 373, here shown as a bent capillary tube which forms the collector body. Liquid sample 30 is collected at the base of the apparatus. Two-stage ADL aerosol concentrator modules having a flow split of 2500:1 (bulk flow divided by minor flow) or more are compatible with the inventive collector modules.

While outside the scope of this discussion, the upper 5×ADL array (377) in FIG. 21 is used in combination with the first stage skimmer with exhaust manifold 378 to separate a particle-enriched core flow (also termed the 'minor flow') from a bulk flow (marked "B") that is depleted in particles. The particle-concentrated gas stream is then conveyed to the collector 373 through first stage adaptor 374, and optionally as shown here, passed through a second stage ADL/skimmer 372, resulting in a second bulk flow split and further concentration of the particle content of the gas stream, which is routed into the collector via adaptor 375.

The purpose of this combination 370 is to provide a virtual impactor/inertial impactor combination which is capable of a) sampling ambient aerosols at high sampling flow rates and concentrating those aerosols as a concentrated particle beam; b) impacting the particles from the particle beam in a collector and capturing them; and c) solubilizing or suspending the particle deposit in a microdroplet volume for analysis. The upstream concentrator module delivers a concentrated aerosol stream ("minor flow") that is injected into the collector channel. In this way, total system throughput can be increased to 20, 30 or even 25000 L/min while retaining the ability to sample impacted aerosol material in microdroplet volumes. This is a distinct technological advantage, increasing detector sensitivity and assay speed. Happily, this combination 370 was found to quickly reduce the aerosol mass found in a cubic meters of air or more to a few nanoliters of liquid sample 30 in less than a minute.

As shown, the collected particles can be eluted from the capillary wall with a very small droplet or a series of droplets of elution fluid, even nanoliter-sized droplets, enabling large concentration factors and affording significant technical and cost advantages relative to current devices. In the case of biological particles, analysis of the collected particles may be performed using a variety of detection methods such as immunological or nucleic acid assays or culturing. The ability of this device to collect large numbers of particles in a short time and deliver them into small fluid volumes offers the possibility to significantly enhance the speed and sensitivity of existing detection and identification methods.

Thus in one aspect the invention is a combination of an ADL and skimmer module (or other air-to-air concentrator) and an "aerosol collector module", for example as exemplified by collector with microelution features 10a, 10b, 40, 50, 250, 260, 280, 300, 320, 330, 340, 370, 450a, 450b, 450c and the variant collector devices and apparatus described herein. Collector modules comprise a receiving arm 3, 102, 124, 252, 271 for receiving a gas stream 6, an outlet arm 5, 125, 258, 272 for discharging a particle depleted exhaust 7, and a particle trap 4, 41, 51, 101, 126, 127, 128, 129, 130, 250, 256, 262, 281, 303, 322, 331, 342, 350, 358 with microfluidic injection/sampling duct 11, 26, 28, 44, 54, 64, 131, 132, 133, 134, 135, 161, 177, 179, 207, 208, 263, 284, 285, 324, 325, 333, 334, 346, 357, 444a, 444b, 444c for injecting a reagent and eluting a liquid sample 30 in a microdroplet volume. These "collector modules", as termed herein, are optionally combined in a single integrated body or assembled on an apparatus scaffold so that disposable elements can be speedily replaced.

In addition to the collector module, a complete aerosol sampling apparatus may include an upstream aerosol concentrator module, plumbing and flow control components, and remotely mounted microfluidic components for eluting the particles from the collector. The detection and analysis of the eluted sample may be performed downstream of the collector body by a number of methods which require delivery of aerosol or its chemical constituents in liquid suspension e.g.: surface plasmon resonance, high performance liquid chromatography/mass spectrometry (HPLC/MS), ICP/MS (Perkin-Elmer), MALDI/MS, FABS, GC/MS, PCR, ELISA, etc, or may be performed in situ in the collector body, for example via an optical window through the particle trap or a waveguide mounted in a microfluidic sampling duct.

The collector module can be a disposable component of the system, whereas the pumps, flow meters, flow controllers, other hardware for in-situ sample analysis will be multi-use components. However, if the detection technique requires the use of small channel cavities formed in expensive materials (e.g. etched channels in quartz) such a collection device can be reusable. Regenerated impactor surfaces 203,322 are envisaged.

Figure 22:
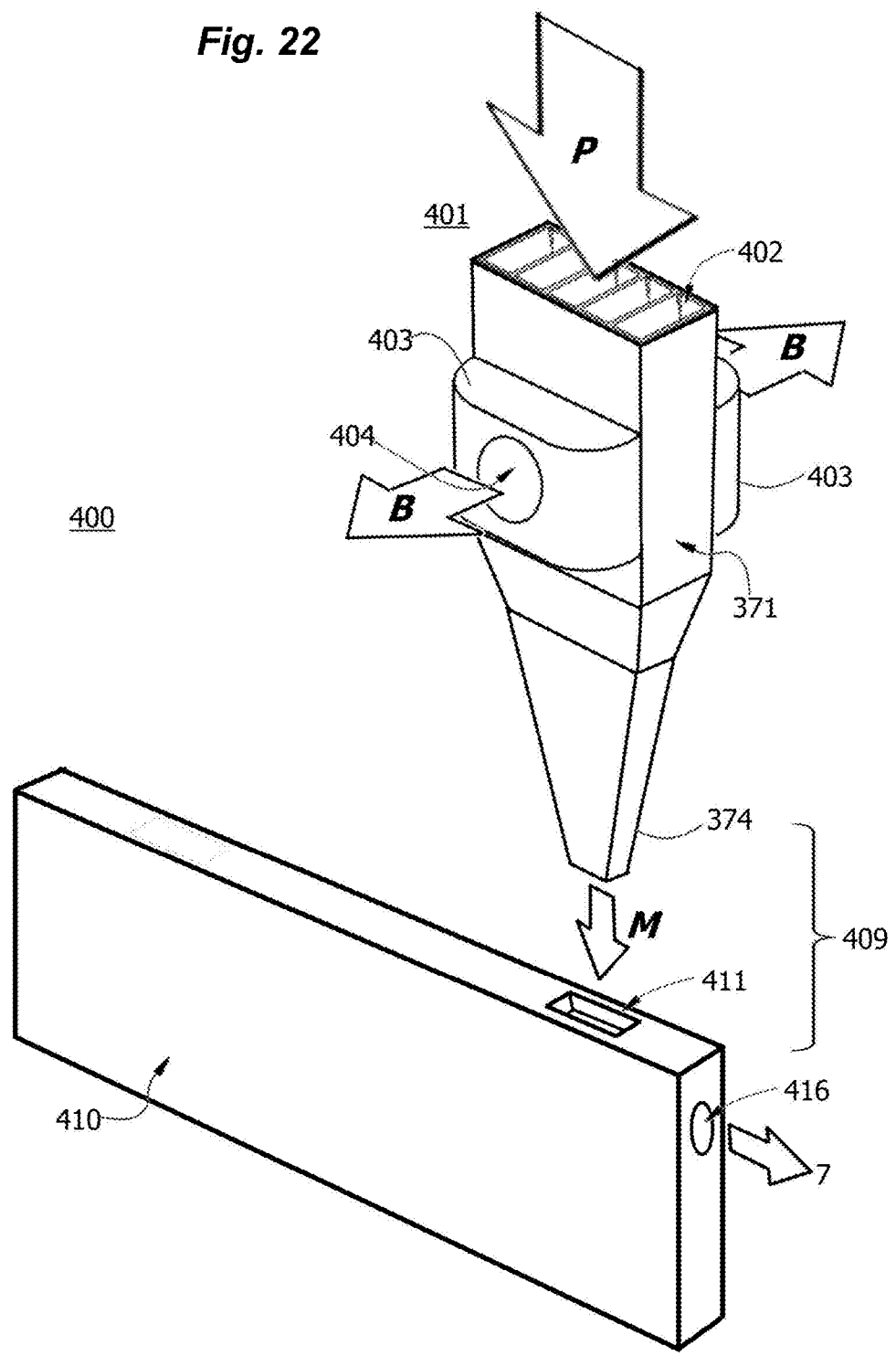
FIG. 22 depicts schematically an apparatus with integrated microfluidic particle trap and nucleic acid amplification and detection cartridge interfaced with a single stage ADL with skimmer and adaptor.

FIG. 22 is an illustration of a combination 400 of a single-stage aerosol concentrator aerosol and a collector module integrated inside a microfluidic card 410, the microfluidic card having partially integrated on-board detection and identification capability. An aerosol-laden gas stream (P) enters an aerosol concentrator module 401 at inlet 402. A bulk flow (B) is separated from a minor flow (M) in an aerodynamic lens array 371. The bulk flow is diverted to waste through manifolds 403 and outlet port 404. The particle-enriched minor flow from the ADL array enters a funnel-like adaptor 374, the adaptor having means for sealedly joining 409 the adaptor to microfluidic cartridge 410. Receptacle 411 is part of the joining means 409 and serves to convey the minor flow (M) from the aerosol concentrator module 401 to the collector, which is integrated in microfluidic cartridge 410. The collector is a centrifugal impactor, bluff body impactor, or electrostatic precipitator integrated inside the microfluidic cartridge 410 and is not shown here, but representative collectors in various embodiments are shown in FIGS. 1, 2, 3, 4, 5B, 5C, 8, 9, 10, 11, 13, 14, 15, 16, 17, 18, 19, 20, 21, 22 and 23. Inside the microfluidic cartridge 410, particles are captured in a particle trap as previously described. A vacuum is used to pull the minor flow through the collector. Depleted particle exhaust 7 exits the cartridge at outlet port 416. This concentrator/collector/detector combination 400 illustrates a modular aerosol concentrator with fluidic connection to an integrated microcollector and microfluidic analysis cartridge.

Turning now to FIG. 23, a schematic is presented showing how modular elements of a concentration-collection-analysis apparatus may be interfaced as a fully functional aerosol concentrator/liquid sample collector/and analytical apparatus 490a. Modules 440a, 450a, and 460a are fluidly connected and are configured to function as an aerosol-to-liquid converter. Module 440a, an aerosol concentrator module, is capable of processing 20, 30, 1000 or more liters per minute of a gas at intake 441 and diverting a major fraction of that gas, depleted of particles, to bulk flow exhaust 442. The "particle-enriched gas stream" 6 is then routed into module 450*a*, an aerosol collector module with particle trap and micro-elution capability via microfluidic duct 444*a* which is adapted for interfacing with analysis module 460*a*. Particle trap components (not shown) of module 450 include inertial impactors and electrostatic precipitators. While not limiting, microfluidic duct 444*a* is part of a fluid handling system for eluting particles collected in the particle trap and conveying solubilized or suspended liquid sample 30 for downstream analysis in module 460*a*, a "liquid sample analysis module". Liquid sample analysis module 460*a* is an integrated microfluidic analytical workstation for performing one or several analytical subroutines, such as liquid chromatography, lateral flow chromatography, ELISA, nucleic acid amplification and detection, PCR, fluorescence spectroscopy, and other means for detecting as are desired.

Integration in construction may be advantageously accomplished by joining modules 440*a* and 450*a* in an integrated solid body 470*a* consisting of an aerosol concentrator and an aerosol collector. Integration of modules 450*a* and 460*a* into a single solid body 480*a* may also be advantageous if desired. All three modules, 440*a*, 450*a* and 460*a* may also be joined in a single integrated device 490*a*. Conversely, it may be advantageous to supply each of the three modules separately, so that, for example, the aerosol collector module 450*a* and the liquid sample analysis module 460*a* are disposable.

According to another embodiment of the invention, the aerosol concentrator module 440*a* and liquid sample module 460*a* are framed in an apparatus with supporting pumps, fans, vacuum pumps, waste sinks, reagent reservoirs, electrical supplies, temperature controls, spectrophotometers, analytical instrumentation, and so forth, and the aerosol collector module 450*a* is a disposable part that is fluidly plugged in for each analytical run.

According to another embodiment of the invention, the aerosol collector module 450*a* is fluidly plugged into an apparatus containing the aerosol concentrator module 440*a* for an analytical run, and following the run, the aerosol collector module 440*a*, which is for this embodiment a small block of plastic with embedded collector channel and particle trap, is then removed and forwarded to a separate workstation for sample preparation and analysis.

Figure 24:
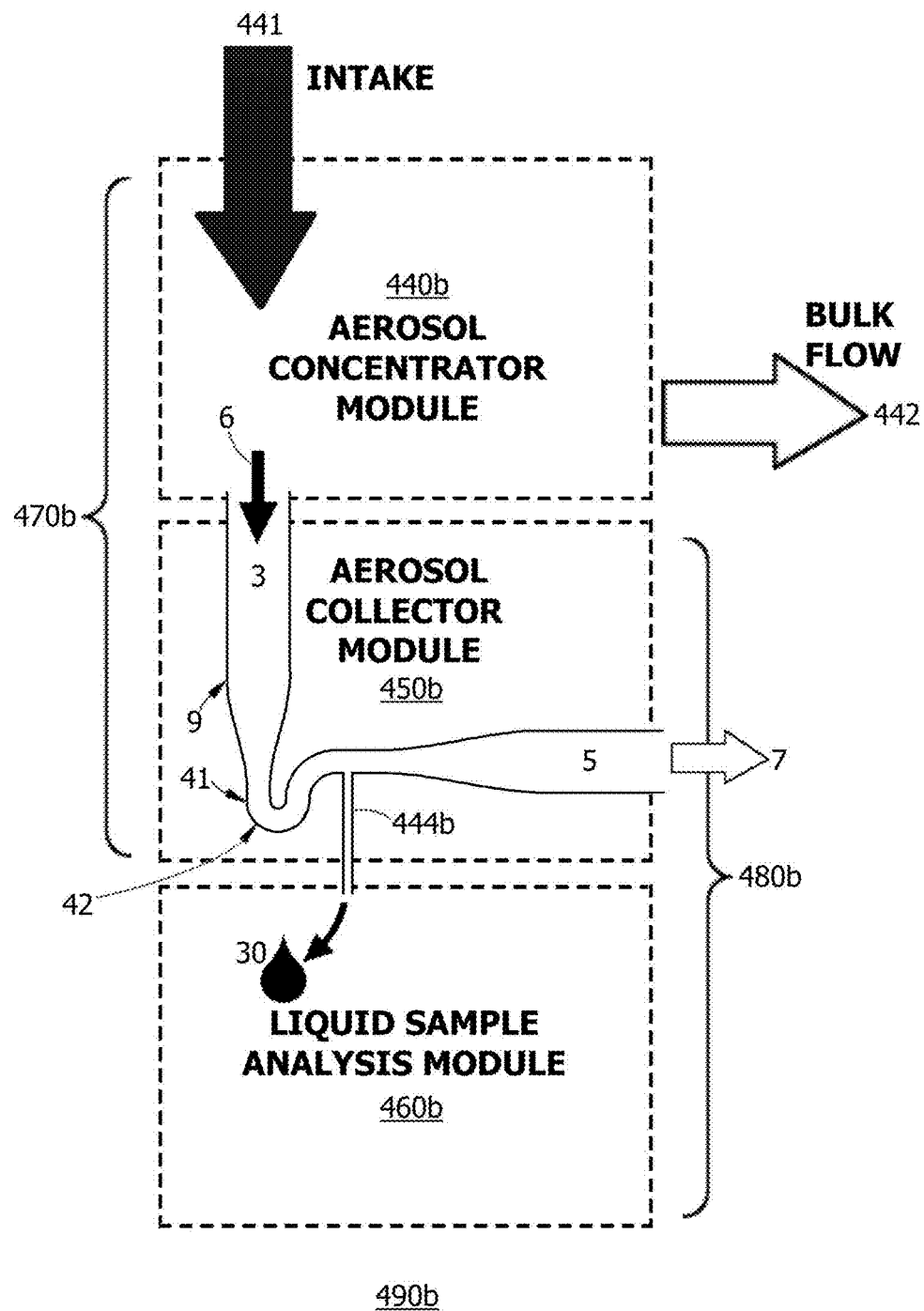
FIG. 24 shows how modular construction with a collector body of the invention can be used to build an aerosol analytic apparatus integrating a centrifugal particle trap.

In FIG. 24 a modular aerosol-to-liquid converter 490*b* with centrifugal impactor 41 is shown. Modules 440*b*, 450*b*, and 460*b* are fluidly connected and are configured to function as an aerosol-to-liquid converter. Module 440*b*, an aerosol concentrator module, is capable of processing 20, 30, 1000 or more liters per minute of a gas at intake 441 and diverting a major fraction of that gas, depleted of particles, to bulk flow exhaust 442. The particle-enriched gas stream 6 is then routed into module 450*b*, an aerosol collector module with collector channel 9, receiving arm 3, centrifugal impactor 41, impactor surface 42, outlet arm 5, and micro-elution capability via a microfluidic duct 444*b* which is adapted for delivering liquid sample 30 to liquid sample analysis module 460*b*. Liquid sample analysis module 460*b* is configured with means for detecting as desired.

Integration in construction may be advantageously accomplished by joining modules 440*b* and 450*b* in an integrated solid body 470*b* consisting of an aerosol concentrator and an aerosol collector. Integration of modules 450*b* and 460*b* into a single solid body 480*b* may also be advantageous if desired. All three modules, 440*b*, 450*b* and 460*b* may also be joined in a single integrated device 490*b*. Conversely, it may be advantageous to supply each of the three modules separately, so that, for example, the aerosol collector module 450*b* and the liquid sample analysis module 460*b* are disposable.

According to another embodiment of the invention, aerosol collector module 440*b* is a small block of plastic with embedded collector channel and particle trap, which is removed so that the liquid sample 30 may be forwarded to a separate workstation for sample preparation and analysis.

Figure 25:
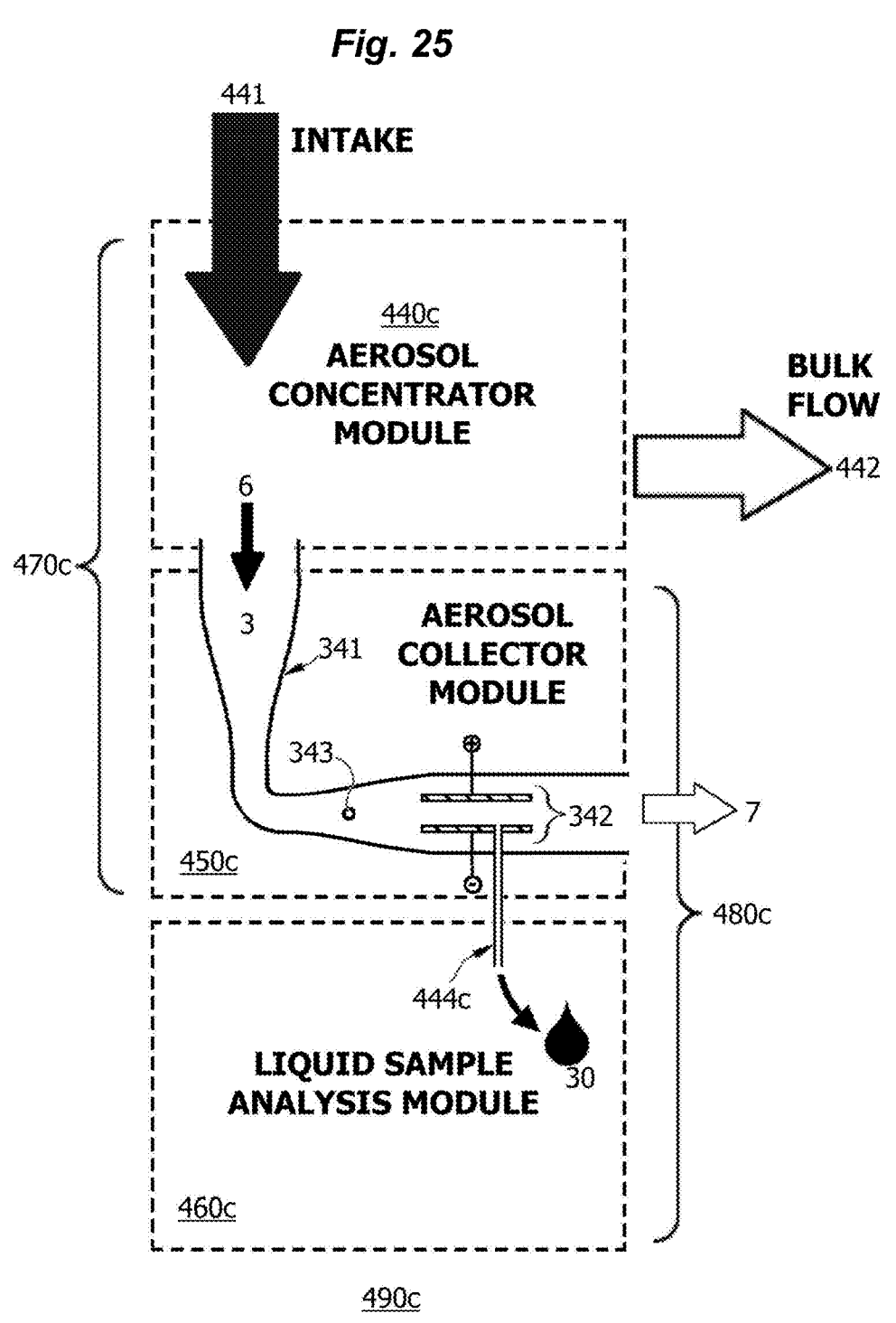

In FIG. 25 a modular aerosol-to-liquid converter 490*c* is shown. Modules 440*c*, 450*c*, and 460*c* are fluidly connected and are configured to function as an aerosol-to-liquid converter. Module 440*c*, an aerosol concentrator module, is capable of processing 20, 30, 1000 or more liters per minute of a gas at intake 441 and diverting a major fraction of that gas, depleted of particles, to bulk flow exhaust 442. The particle-enriched gas stream 6 is then routed into module 450*c*, an aerosol collector module with collector channel 341, receiving arm 3, corona wire 343, electrostatic particle collector 342, and micro-elution capability via a microfluidic duct 444*c*, which is adapted for delivering liquid sample 30 to liquid sample analysis module 460*c*. Liquid sample analysis module 460*c* is configured with means for detecting as desired.

Integration in construction may be advantageously accomplished by joining modules 440*c* and 450*c* in an integrated solid body 470*c* consisting of an aerosol concentrator and an aerosol collector. Integration of modules 450*c* and 460*c* into a single solid body 480*c* may also be advantageous if desired. All three modules, 440*c*, 450*c* and 460*c* may also be joined in a single integrated device 490*c*. Conversely, it may be advantageous to supply each of the three modules separately, so that, for example, the aerosol collector module 450*c* and the liquid sample analysis module 460*c* are disposable.

According to another embodiment of the invention, the aerosol concentrator module 440*c* and liquid sample module 460*c* are framed in an apparatus with supporting pumps, fans, vacuum pumps, waste sinks, reagent reservoirs, electrical supplies, temperature controls, spectrophotometers, analytical instrumentation, and so forth, and the aerosol collector module 450*c* is a disposable part that is inserted so as to be fluidly and electrically connected for each analytical run.

Figure 26:
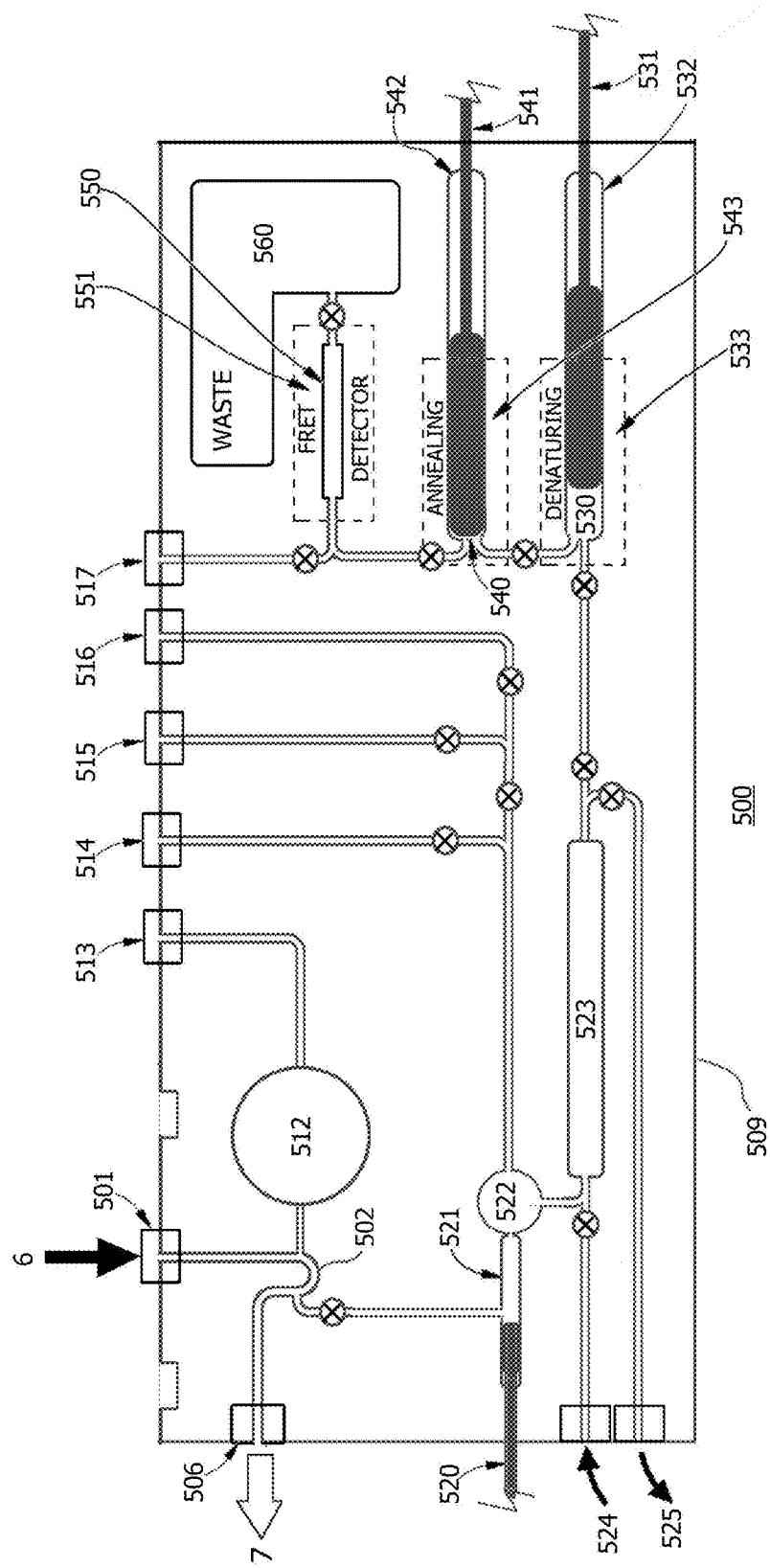
FIG. 26 is an example of a microfluidic card with integrated particle trap and microfluidic circuitry for amplifying and detecting a nucleic acid.

Analysis by PCR is an embodiment of a means for detecting an aerosol particle or aerosol constituent comprising a nucleic acid. In FIG. 26, the workings of an illustrative microfluidic cartridge 500 with integrated particle trap for analyzing a liquid sample by molecular biological techniques are shown in more detail. Gas stream 6 enters the cartridge through receptacle 501 and any aerosol particles and nucleic acid constituents are trapped in a particle trap 502 (although the workings of a centrifugal impactor are shown, the principle of operation is not limited to centrifugal impactors) before the depleted gas stream 7 is drawn to waste by a downstream vacuum source coupled to the cartridge at outlet 506. The analytical process is performed within the plastic body 509 of microfluidic cartridge 500.

When the vacuum is shut off, inkjet printer head 512 injects elution fluid 513 from an off-card reservoir into particle trap 502, eluting the aerosol sample material. Plunger 520, a micro-syringe pump 521, draws the liquid eluate from the impactor trap and reversing the plunger stroke forces the liquid sample into an in-line chamber 522 which is fitted externally with an ultrasonic PZT transducer (not shown) and a diaphragm made of polyethylene terephthalate, or some suitable material. The action of the ultrasonic transducer is brief, but results in disruption of cellular structures and spores in the sample, releasing nucleic acids. A lysis solution 514 is added to augment the disruptive force of the ultrasound in chamber 522. The material is then transferred to a solid state extraction chamber 523 which functions as an affinity column for nucleic acid, as first described by Boom (U.S. Pat. No. 5,234,809). Following rinse with ethanol 515 to remove cellular lipids, sugars and other detritus, and a brief exposure to air 524 to vent the ethanol to an external trap 525, a low-ionic strength PCR buffer 516 is used to elute nucleic acids adsorbed to the solid state extractant in column 523. By opening valves and actuating plunger 531 of micro-syringe pump 532, the eluted nucleic acids are moved into a denaturation chamber 530 and heated to a denaturation temperature by first heating element 533. While not shown, an intermediate temperature could be used in combination with reverse transcriptase so that ssRNA could also be analyzed by this method. The denaturation chamber 530 (or microfluidic channels joining the chamber) contains dried reagents, including a heat-stable polymerase, primers and essential cofactors and NTP nucleotides required for PCR. The denatured material is then moved to the annealing chamber 540 by action of a second plunger 541 and syringe pump 542. Temperature in the annealing chamber is controlled by a second heating element 543. In the annealing chamber, primers hybridize and chain elongation continues until the products are returned to the denaturation chamber 530 by reciprocal action of the plungers. This heating, annealing and elongation cycle is repeated multiple times. An entire PCR reaction may be performed with a few microliters total volume in a micro fluidic device on a sample of aerosol particles eluted from an impactor integrated in a microfluidic card 500. Upon completion of a required number of PCR amplification cycles, 15 to 50 cycles perhaps, the products are transferred to a FRET detector chamber 550 with variable heating element 551 and dried fluorescent molecular probes and observed using an external light source and detector (not shown) for a characteristic fluorescence melt signature of the sought-after target as a function of temperature in the FRET chamber. Upon completion of the assay, the material is contacted with a waste chamber 560 containing a disinfectant, and the entire microfluidic cartridge body 509 may be uncoupled from the reagent lines and any upstream aerosol concentrator and discarded.

In an alternate embodiment, a skimmer is also integrated into the disposable plastic body 509 of the microfluidic cartridge 500.

According to another aspect of the invention, therefore, we conceive integrated systems for analyzing an ambient air sample for an aerosol particle. The integrated systems are illustrated conceptually in the embodiments of FIGS. 21 through 25. Collector modules include centrifugal impactors, bluff body impactors, and electrostatic precipitators.

In one aspect, the present invention is practiced by integrating an aerosol collector module as defined herein into a body of a microfluidic cartridge with microfluidic sub-circuitry designed to enable nucleic acid amplification and detection. Aerosol particles collected on an impactor surface are conveyed in a liquid sample into a microfluidic circuit for analysis. Disclosed are illustrative details of microfluidic circuitry for integrated nucleic acid analysis, such as by PCR.

Teachings which may be relied upon for construction of a PCR sub-circuit of the device of FIG. 26 include, for example, Nakano H et al. 1994. High speed polymerase chain reaction in constant flow. Biosci Biotechnol Biochem 58:349-52; Wilding, P et al. 1994. PCR in a silicon microstructure. Clin Chem 40(9):1815-18; Woolley A T et al. 1996. Functional integration of PCR amplification and capillary electrophoresis in a microfabricated DNA analysis device. Anal Chem 68:4081-86; Burke D T et al. 1997. Microfabrication technologies for integrated nucleic acid analysis. Genome Res 7:189-197; Kopp et al. 1998. Chemical amplification: continuous-flow PCR on a chip. Science 280:1046-48; Burns, M A. 1998. An Integrated Nanoliter DNA Analysis Device. Science 282:484-87; Belgrader P et al. 1999. PCR Detection of bacteria in seven minutes. Science 284:449-50; Lagally E T et al. 2001. Fully integrated PCR-capillary electrophoresis microsystem for DNA analysis. Lab Chip 1:102-07; Tudos A J et al. 2001. Trends in miniaturized total analysis systems for point-of-care testing in clinical chemistry. Lab Chip 1:83-95; Belgrader P et al. 2002. A battery-powered notebook thermocycler for rapid multiplex real-time PCR analysis. Anal Chem 73:286-89; Hupert L M et al. 2003. Polymer-Based Microfluidic Devices for Biomedical Applications. In, (H Becker and P Woias, eds) Microfluidics, BioMEMS, and Medical Microsystems, Proc SPIE Vol 4982:52-64; Chartier I et al. 2003. Fabrication of an hybrid plastic-silicon microfluidic device for high-throughput genotyping. In, (H Becker and P Woias, eds) Microfluidics, BioMEMS, and Medical Microsystems, Proc SPIE Vol 4982:208-219; Anderson R C et al. 2000. A miniature integrated device for automated multistep genetic assays. Nucl Acids Res 28(12):[e60,i-vi]; Yang, J et al. 2002. High sensitivity PCR assay in plastic micro reactors. Lab Chip 2:179-87; Giordano B C et al. 2001. Polymerase chain reaction in polymeric microchips: DNA amplification in less than 240 sec. Anal Biochem 291:124-132; Khandurina J et al. 2000. Integrated system for rapid PCR-based DNA analysis in microfluidic devices. Anal Chem 72:2995-3000; Chiou, J et al. 2001. A Closed-Cycle Capillary Polymerase Chain Reaction Machine. Anal Chem 73:2018-21; Yuen, P K et al. 2001. Microchip module for blood sample preparation and nucleic acid amplification reactions. Genome Res 11:405-412; Zhou X, et al. 2004. Determination of SARS-coronavirus by a microfluidic chip system. Electrophoresis. 25(17):3032-9; Liu Y et al. 2002. DNA amplification and hybridization assays in integrated plastic monolithic devices. Anal Chem 74(13):3063-70; Zou, Q et al. 2002. Micro-assembled multi-chamber thermal cycler for low-cost reaction chip thermal multiplexing. Sensors Actuators A 102: 224-121; Zhang C et al. 2006. PCR Microfluidic devices for DNA amplification. Biotech Adv 24:243-84, and Zhang, C and Xing D. 2007. Miniaturized PCR chips for nucleic acid amplification and analysis: latest advances and future trends. Nucl Acids Res 35(13):4223-37. Other amplification protocols include LAMP (loop-mediated isothermal amplification of DNA) reverse transcription polymerase chain reaction (RT-PCR), ligase chain reaction ("LCR"), transcription-based amplification systems (TAS), including nucleic acid sequence based amplification (NASBA), "Rolling Circle", "RACE" and "one-sided PCR". These various non-PCR and variant amplification protocols have various advantages in diagnostic assays, but PCR remains the workhorse in the molecular biology laboratory and in clinical diagnostics. Embodiments disclosed here for microfluidic PCR should be considered representative and exemplary, but not limiting, of a general class of microfluidic sub-circuits capable of executing one or various amplification and detection protocols.

FIG. 27 shows representative data from a PCR assay performed with an apparatus of FIG. 26 as modified for RT-PCR and outfitted with an upstream aerosol concentrator module (440a,440b,440c). Such a device as modified and outfitted is representative of a fully integrated apparatus for aerosol sampling and analysis (400,490a,490b,490c). As can be seen, real-time PCR is sensitive to the "copy number" of nucleic acids in the captured bioaerosol, thus for every copy of a nucleic acid sequence trapped in an inertial impactor and amplified, there is a proportionate improvement in time to detectable signal; $10000/m^3$ copies gives a detectable signal by RT-PCR several cycles sooner than 1000 copies/m$^3$. Analyses of this time are possible only if the large aerosol volume can be reduced to a small liquid sample. By use of an air-to-liquid converter combinations (470a,470b,470c) as described here, the bioaerosol content of one cubic meter or one hundred cubic meters of air for example can be analyzed as a microdroplet sample of a few microliters or less.

Figure 28A:
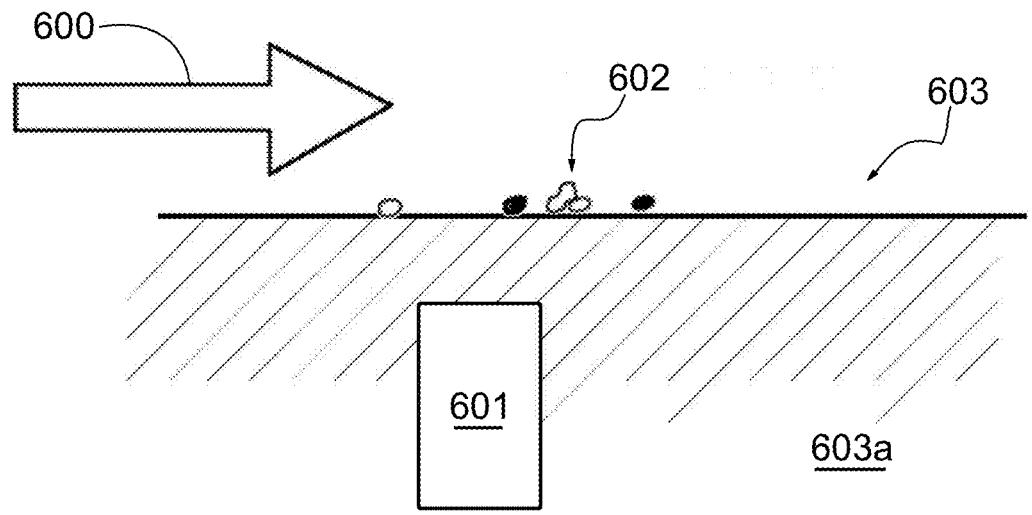
FIGS. 28A and 28B depict use of a contacting electro-acoustic transducer in combination with a stream of a flowing gas to clean an air:solid surface, dislodging particles resident thereon.
Figure 28B:
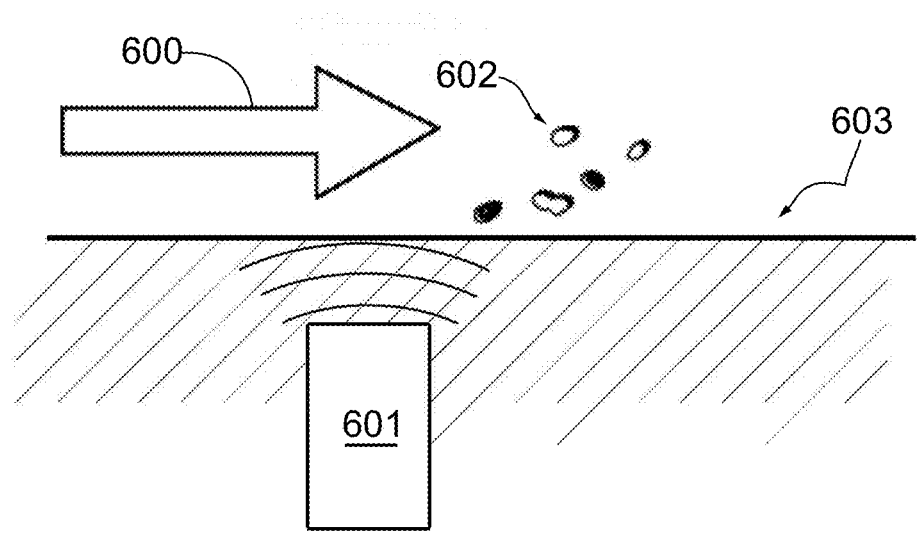

Referring now to the figures, FIGS. 28A and 28B depict use of a contacting electro-acoustic transducer 601 in combination with a flowing gas stream 600 to clean particles 602 from an air:solid surface 603 in a device with body 603a, the acoustic energy dislodging resident particles resident into the gas stream. As shown in FIG. 28A, particles which are resident on a surface that is subjected to a flowing gas stream alone are not dislodged because of boundary layer conditions, but upon application of acoustic energy (FIG. 28B), the particles are readily entrained in the flowing gas, thereby cleaning the surface. In this case, the contacting transducer is contacting the device body 603a or is embedded in the device body and is a piezoelectric or magnetostrictive transducer. The air:solid surface is generally a wall or an impactor disposed in an internal channel in the body. A couplant may be used to increase efficiency of propagation of sound across the solid:solid interface between the transducer and the solid body of the device if needed.

Figure 29A:
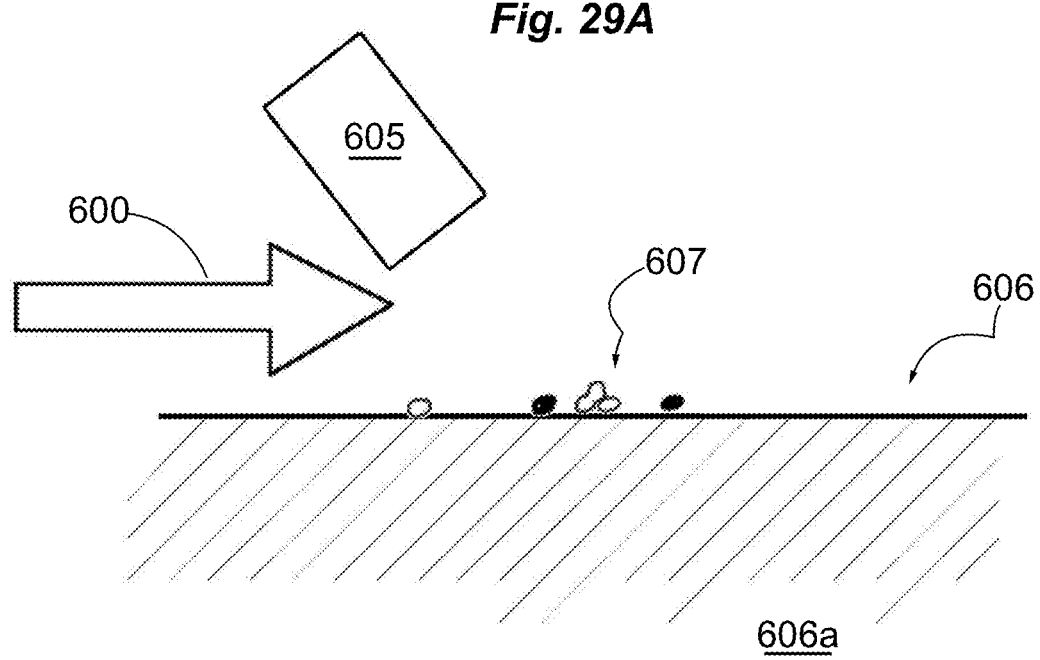
FIGS. 29A and 29B depict use of a non-contacting "air-coupled" electro-acoustic transducer in combination with a stream of a flowing gas to clean an air:solid surface, dislodging particles resident thereon.
Figure 29B:
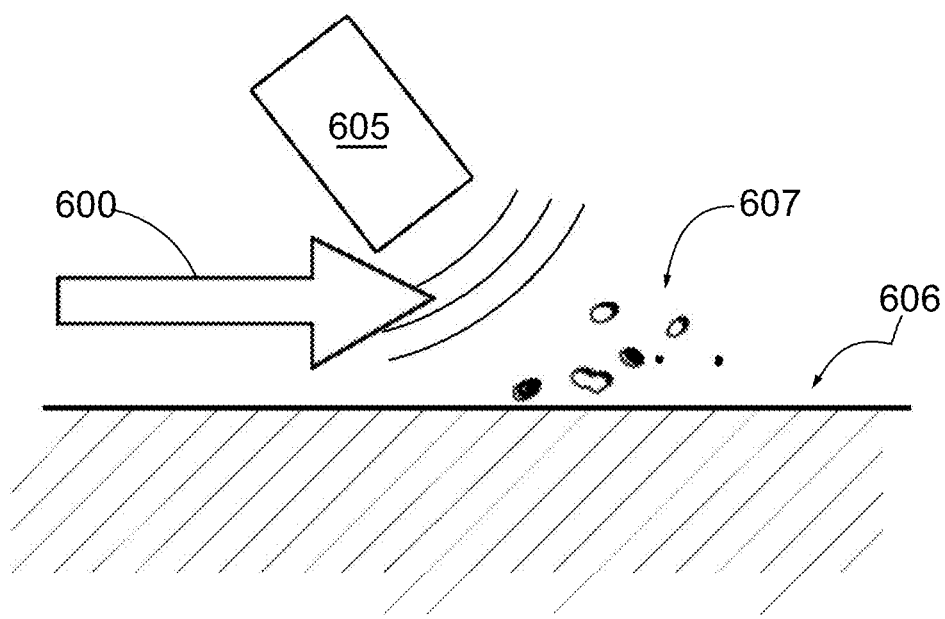

FIGS. 29A and 29B depict use of a non-contacting electro-acoustic transducer 605 in combination with a stream of a flowing gas 600 to clean an air:solid surface 606 in a device with body 606a, dislodging particles 607 resident or accreted thereon. Also known as an "air-coupled" transducer, acoustic energy may be transmitted from the transducer 605 through a gas medium with efficiency sufficient to excite an air:solid interface at a distance. Efficiency of coupling can be increased by collimating or focusing the acoustic beam and by operating the transducer in a resonant mode. As shown in FIG. 29A, particles resident on surface 606 are subjected to a flowing gas stream, but because of unstirred boundary layer conditions, remain in place. However, upon application of gas-coupled acoustic energy, the re-aerosolized particles are readily entrained in the flowing gas, cleaning the surface (FIG. 29B).

Figure 30A:
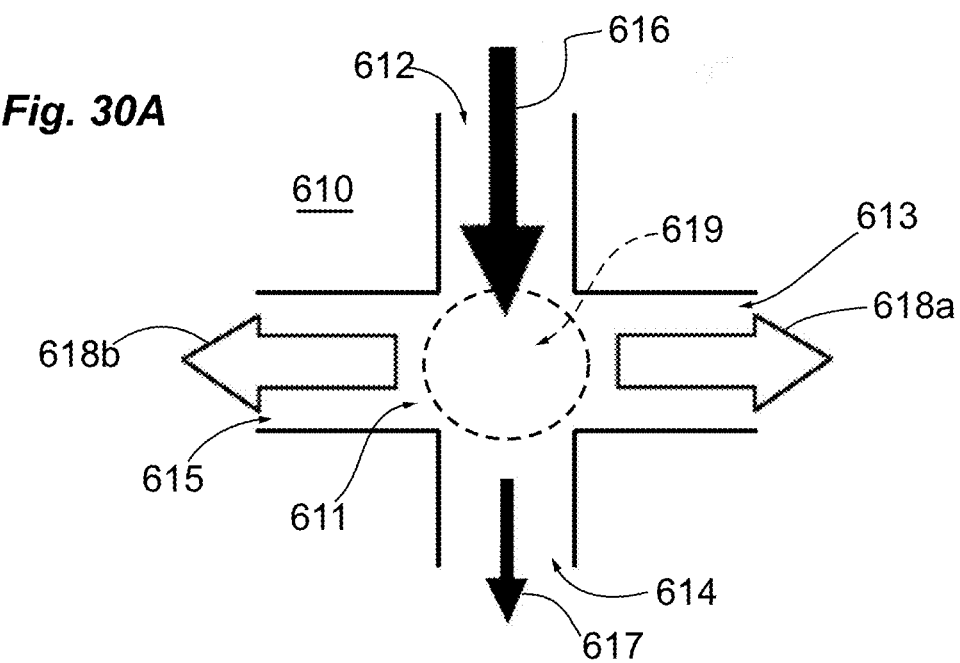
FIGS. 30A and 30B depict schematically a skimmer junction with open vestibule or window aligned transversely through the skimmer, perpendicular to the exposed face of the intersecting channels, and provision for directing dry or wet acoustic energy onto particle accretion surfaces along the skimmer junction. The same view is rendered with perspective in FIG. 30B.
Figure 30B:
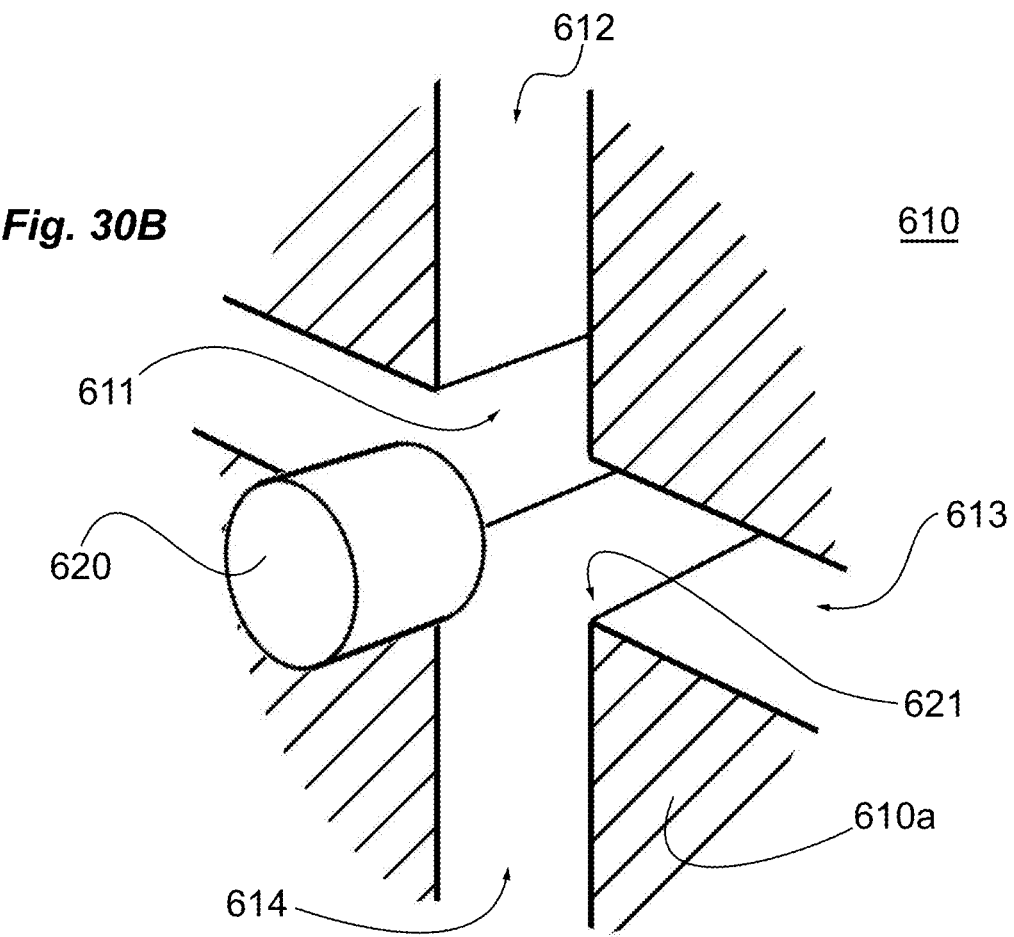

Aerosol sampling from gas streams typically involves particle concentrators such as that shown schematically in FIGS. 30A and 30B. The illustration depicts a skimmer assembly 610. An intersection 611 of four channels is shown. Listing the arms clockwise from topwise are an intake channel 612, a right chimney arm 613, a collector channel ("conduit" or "duct") 614, and a left chimney arm 615. This configuration is termed a "skimmer" because it is configured to separate a gas stream 616 into a minor flow 617, which is particle enriched, from a major flow (618a,618b), which is particle depleted. The major flow exits via the chimney arms; the minor flow via the collector channel at the bottom.

Also shown is an open vestibule 619 (dashed circle) perpendicular to the intersection of the channels. Skimmers 610 may be constructed with an extended "slit" geometry to increase volume throughput, and the vestibule runs the length of the skimmer. This is seen in three dimensions in FIG. 30B, where a transducer 620 is shown aimed into the skimmer assembly on the long axis of junction 611 illustrated as extending into the paper from front face 610a. The inside lower "lips" 621 of the collector channel form a virtual impactor aperture or "mouth", and particle deposition around this mouth has been shown to be problematic during extended use. The lips 621 of the virtual impactor are a particle accretion surface. Particles adherent on the walls of the intake channel, collector channel, or around the virtual impactor lips can build up, leading to fouling and deteriorating performance. Application of acoustic energy, using either directly coupled or air-coupled transducers, has been found here to eliminate this buildup. Liquid in the internal passages of the skimmer junction may be used to acoustically couple the source of insonation to the surfaces to be insonated. While a slit-type skimmer geometry is shown, cleaning of skimmers having an annular, axisymmetrical geometry is also realized using electro-acoustic transducers operatively coupled to the nose of the skimmer.

Figure 31A:
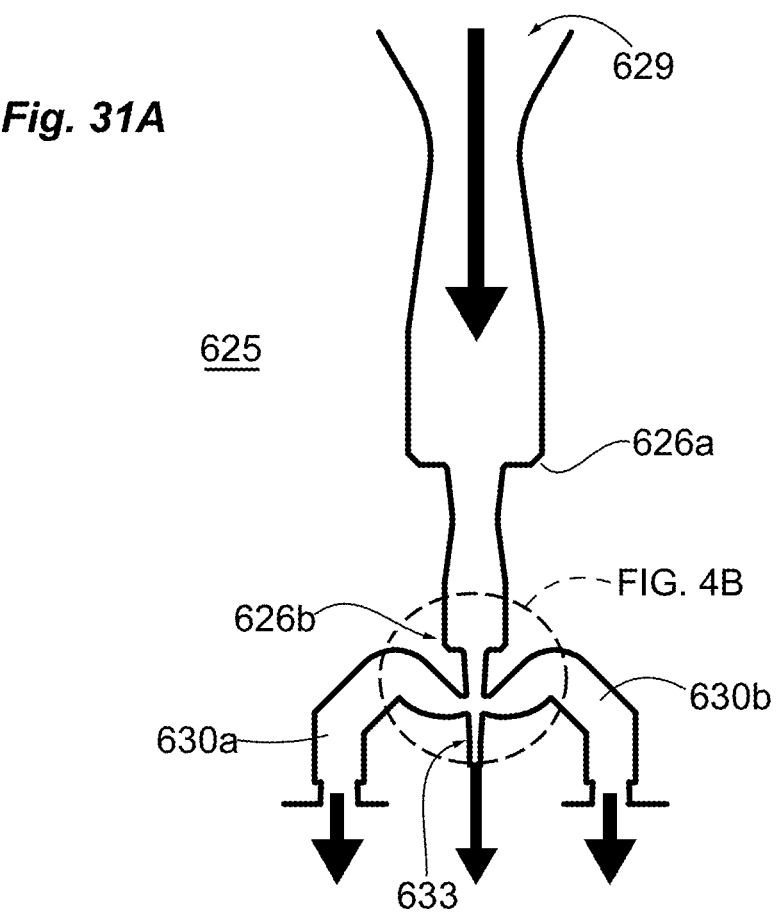
FIGS. 31A and 31B show a cross-section through a skimmer with upstream aerodynamic lense and depicts locations of openings where transducers may be aimed for dry or wet cleaning cycles.
Figure 31B:
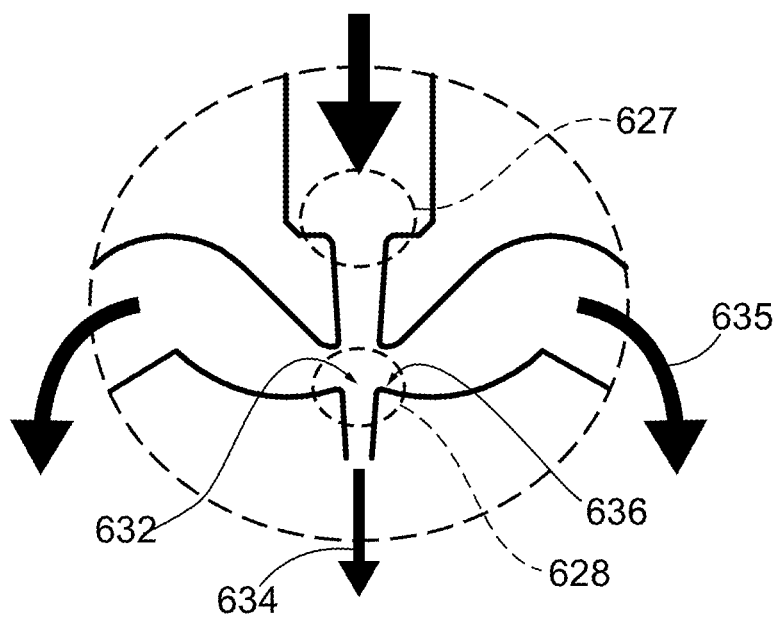

FIGS. 31A and 31B show a cross-section through a skimmer 625 with upstream aerodynamic lenses (626a,626b) and again depicts locations of target windows (627,628) where transducer energy may be aimed. FIG. 31A illustrates the basic geometry in cross-section. A particle-laden gas stream enters at the top through inlet 629. Chimney arms (630a, 630b) on the right and left bound the central virtual impactor aperture 632 which forms the mouth of the collector channel 633. The circle indicates the area of the detailed view of FIG. 31B.

In FIG. 31B, flow 634 (dark arrow) at the bottom indicates the direction of the minor flow, which is particle-rich. Arrows 635 represent major flow, which is particle-depleted. Particles that are lost to the walls of the device from the particle rich flow on the long axis of the device may be resuspended and recovered in the minor flow by application of acoustic energy through one or both of the windows shown (dashed circles 627, 628). The stepped ledges forming the aerodynamic lenses (626a,626b) and the lips 636 of the virtual impactor mouth are particle accretion surfaces. Acoustically-powered devices for cleaning skimmers with this profile are realized for both slit- and annular geometries.

Figure 32:
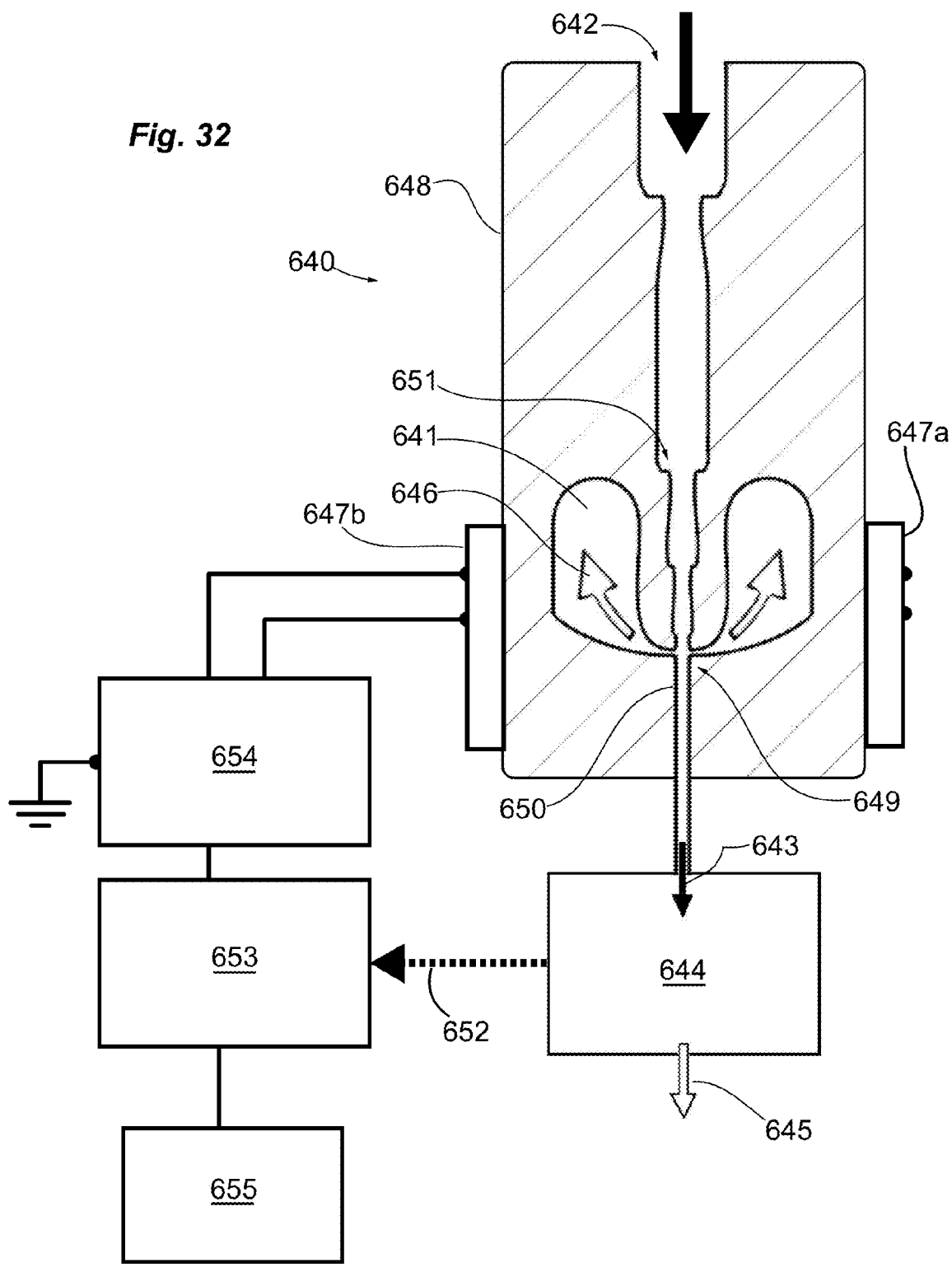
FIG. 32 shows a cross-section through a skimmer with upstream aerodynamic lenses and schematically depicts a piezoelectric, magnetostrictive, or electrostatic transducer element contactingly coupled to the lateral faces of the skimmer body.

FIG. 32 shows a cross-section through a particle concentration device and skimmer 640 having chimneys 641 folded back against the inlet channel 642. The direction of inlet flow of the gas feedstream is downward through the skimmer; a minor flow 643 exits at the bottom of the device and can be routed to a sampler, analytical device, or particle trap 644 before exiting at 645 to suction exhaust. Bulk flow 646 of the particle-depleted gas (the major flow) is directed back and up inside the two chimneys, which extend out of the plane of the image, and are fluidly connected to a suction pressure source.

As shown, piezoelectric transducer elements (647a,647b) are attached in pairs to the sides of the device body 648. Acoustic energy is advantageously conducted through the solid body. Optionally a couplant may be used to improve transmission efficiency. Aqueous liquids are one such couplant. Acoustic energy is propagated through the solid body and excites the internal surfaces of the skimmer, dislodging any buildup of particles around the virtual impactor aperture mouth 649 of the collector channel 650 and on the baffle surfaces 651 of any upstream aerodynamic lens elements before performance-altering fouling can occur. The dislodged particles are resuspended in the gas stream so as to be cleaned from the skimmer and associated surfaces. Particle deposits that have resulted in decrement in performance are cleaned away in this manner.

By fabricating the solid body with volumes of higher density material and lower density material, acoustic energy can be directed along waveguides formed of higher density material. Acoustic excitation may be conveyed to selected surfaces of the apparatus using acoustic waveguides of the type described in US Pat Doc No 2008/0237366 to Ehlert, for example.

A feedback control loop 652 is shown, demonstrating the integration of the electro-acoustic transducers into operation of an aerosol concentration and collection system, using a sensor signal for measuring performance of a particle handling apparatus to control activation and to modulate the acoustic energy emitted by the transducers. As particles accumulate around the skimmer or in the particle trap 644, the sensor detects the particle deposits directly or indirectly by measuring gas velocity, backpressure, reflectance, opacity, or other indica of particle deposition in the trap, which is a particle accretion surface, and emits a signal to a processor 653 and associated control circuitry which controls the transducer driving circuit 654, shown here schematically. A power supply 655 is also shown. In this way, the sensor signal results in application of acoustic energy to the concentrator module body (or to the particle trap body) which breaks up accreted particle deposits and resuspends them in the gas stream, cleaning the inside surfaces and restoring performance. The signal-actuator-sensor circle thus functions as closed feedback loop to enhance and prolong particle monitoring, concentration or collection function without the need for service or disassembly. Signal transmitted to the control circuit is processed to modulate transducer actuation, which in turn regulates the degree of particle accretion inside the particle trap. Similarly, as alternative or complementary illustration, a pressure sensor mounted in the intake channel can be monitored and used to control transducer actuation and modulation of acoustic energy applied to a skimmer body, thereby again forming a feedback loop.

In addition to sensors for detecting an increase in backpressure or flow velocity associated with accretion of particle deposits, direct examination of the inside surfaces of a particle trap may include monitoring based on spectrophotometry, fluorometry, conductivity, resistivity, electroimpedance spectroscopy (more generally, spectrometric and electrometric analysis means), and the like, without limitation thereto. It is sufficient to determine that the particle trap 644 has accumulated a volume of foreign matter in sufficient quantity or of a suspicious nature such that further analysis is merited.

Programmable, low energy, transducer LC driving circuits 654 with sensor feedback circuitry and power supply may be constructed as known in the art. These functions can be achieved with electronic circuitry, such as with microprocessors with volatile and read-only memory, and A/D and D/A converters. The electro-acoustic transducer may be a piezoelectric, magnetostrictive, or capacitive electrostatic transducer, or a hybrid thereof. Transducers are for example Steiner & Martins Inc SMUTK2500RS112 (2.5 MHz, 26 VDC, 800 mA), Nanhai Techsin Electronic Co DK-24 (40 KHz, 24 VAC, 950 mA), or custom piezoelectric transducers and driving circuits available from Microflow Engineering of Sweden which run on AA batteries and are the size of a postage stamp. Battery operated circuits using piezoelectric driver circuits at 3600 Hz with peak currents of 20 mA at 36 mV are described in "Piezoelectric Transducer Driver Circuit with Adjustable Output Level" by Gary Pace (Motorola Inc Technical Developments, Vol 17 Dec. 1992). Ultrasonic driving circuits are described for example in U.S. Pat. Nos. 4,113,809, 4,632,311, 4,641,053, 4,689,515, 5,803,362, 6,361,024, RE39671, and US Pat. Appl. Doc. Nos. 2007/0235555 and 2009/0095821. Such driving circuits may include frequency control, resonance tuning, impedance sensing, soft start, and solid state features. The electro-acoustic transducer and associated circuitry produces acoustic waves to dislodge particle deposits from internal surfaces.

Figure 33:
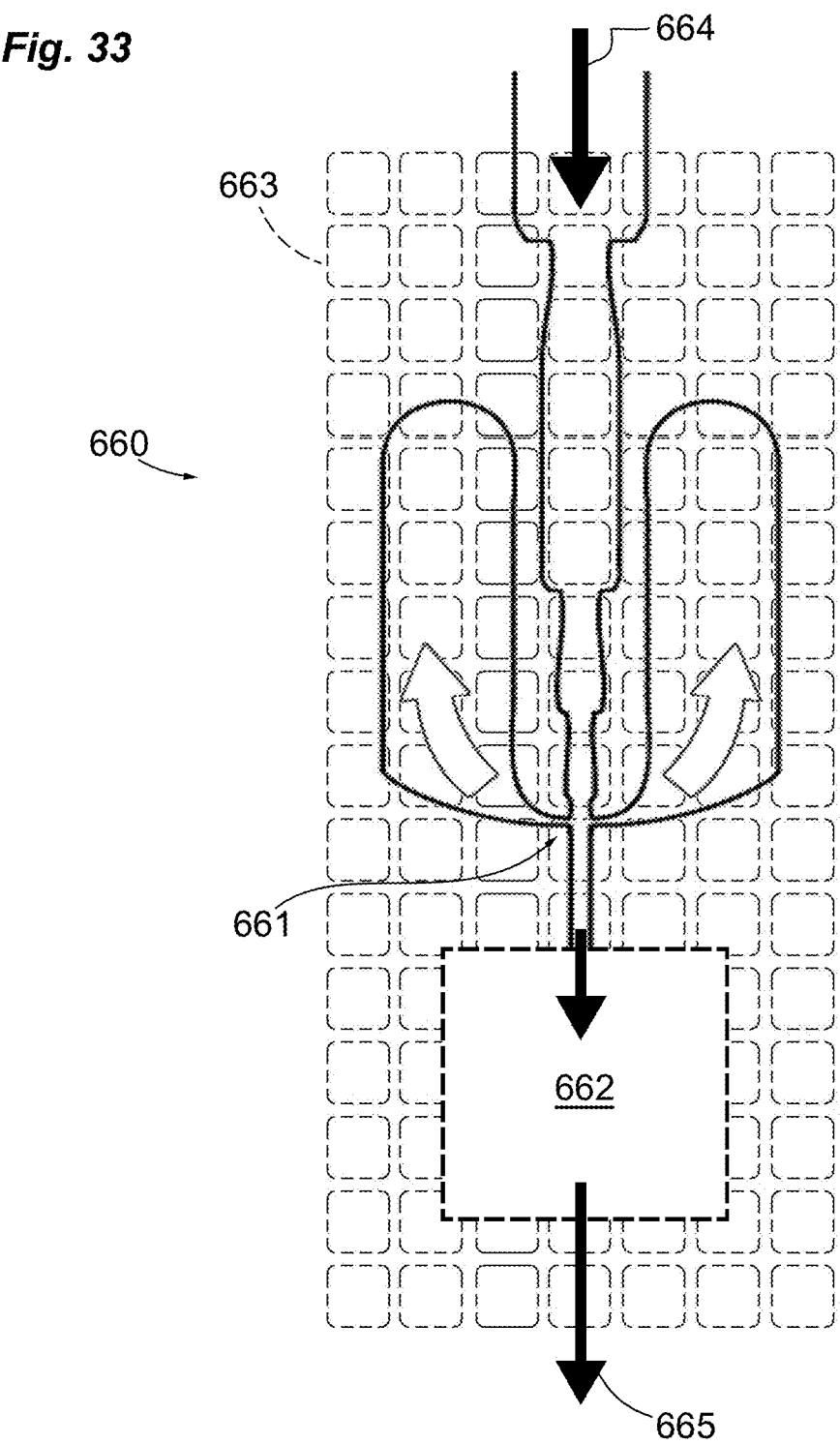
FIG. 33 shows a cross-section through a skimmer with upstream aerodynamic lenses and depicts an interface with an array (dashed lines) of piezoelectric, magnetostrictive, or electrostatic transducer elements.

FIG. 33 shows a cross-section through a skimmer device 660. Again shown are upstream aerodynamic lenses disposed in an intake channel, a skimmer junction 661 recognized by a "tee" junction of four channels, and a downstream particle trap 662. Also shown is an interface 663 containing a rectilinear array of piezoelectric, magnetostrictive, or electrostatic transducer elements (dashed lines). The array of transducers is viewed as acoustically coupling with the body of the skimmer device. Acoustic energy is delivered simultaneously to all particle accumulations surfaces of the aerodynamic lenses, skimmer and particle trap through a couplant medium or solid body, or may be selectively actuated or modulated for particular target areas. Particles that have accumulated on the internal surfaces of the device are readily dislodged and entrained in the flowing gas stream 664 by the application of acoustic energy using the array and are trapped in the particle trap 662 or discharged to waste at 665. While not shown to scale, a variety of array configurations are effective. Multiple parallel particle concentrators and/or collectors in a single body may be treated in this way.

Blockage or partial occlusion of internal surfaces may occur almost any point in aerosol monitoring, concentration, or collection equipment, but is more likely to occur around the mouth of the skimmer 661 and in the particle trap 662. The electro-acoustic transducers or array are configured so that these surfaces are effectively excited by the acoustic energy. Application of acoustic energy can be intermittent or triggered by a signal from a sensor positioned to monitor performance of the equipment.

Particle trap 662 is used for capturing particles on a solid surface, such as by inertial impaction or electrostatic attraction, and is optionally configured with in situ detection capability. The particle trap may also be acoustically cleaned as required, either on a regular schedule, for example as part of a dry cleaning regime, or in response to a signal from a sensor that monitors particle accumulation in the particle trap or indirectly monitors gas flow resistance through the particle trap.

Figure 34:
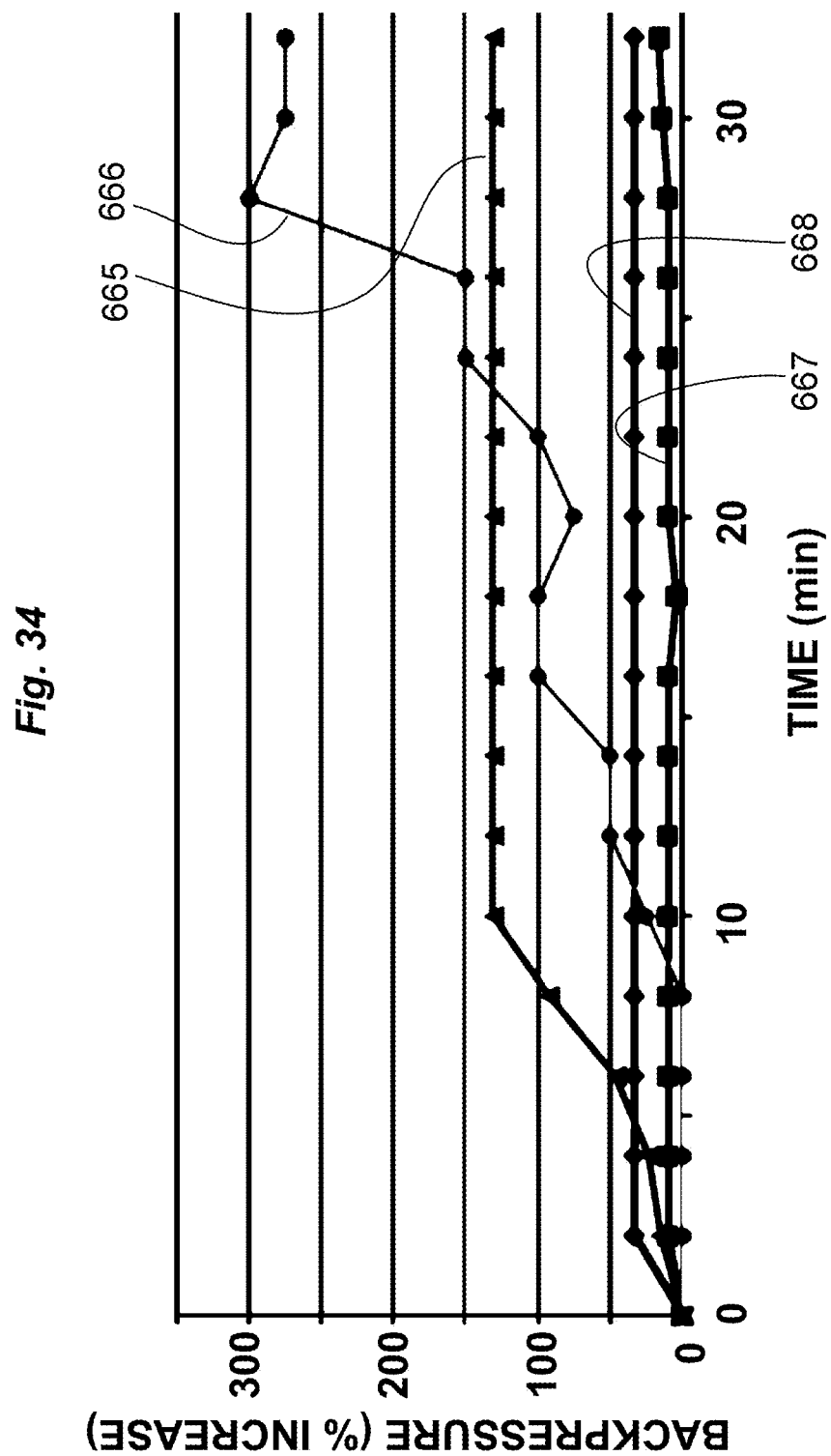
FIG. 34 is a plot monitoring backpressure in an aerosol concentrator with and without periodic application of ultrasonic acoustic energy to the concentrator body.

FIG. 34 is an experimental plot monitoring backpressure in an aerosol concentrator with and without periodic application of ultrasound to the concentrator body. Particle dust in a gas stream was generated using a dry nebulizer and passed through the concentrator. As evidenced by the increase in backpressure in the chimneys and particle trap (665, 666 respectively), particle fouling results in progressive deterioration of performance and buildup of solid deposits in the equipment (see FIG. 42A). FIG. 34 is described experimentally in more detail in Example 3. With periodic cleaning of the chimney passages around the skimmer and particle trap, the problem is alleviated. Backpressure in the chimneys 667 and in the particle trap 668 does not increase over extended operation.

Figure 35A:
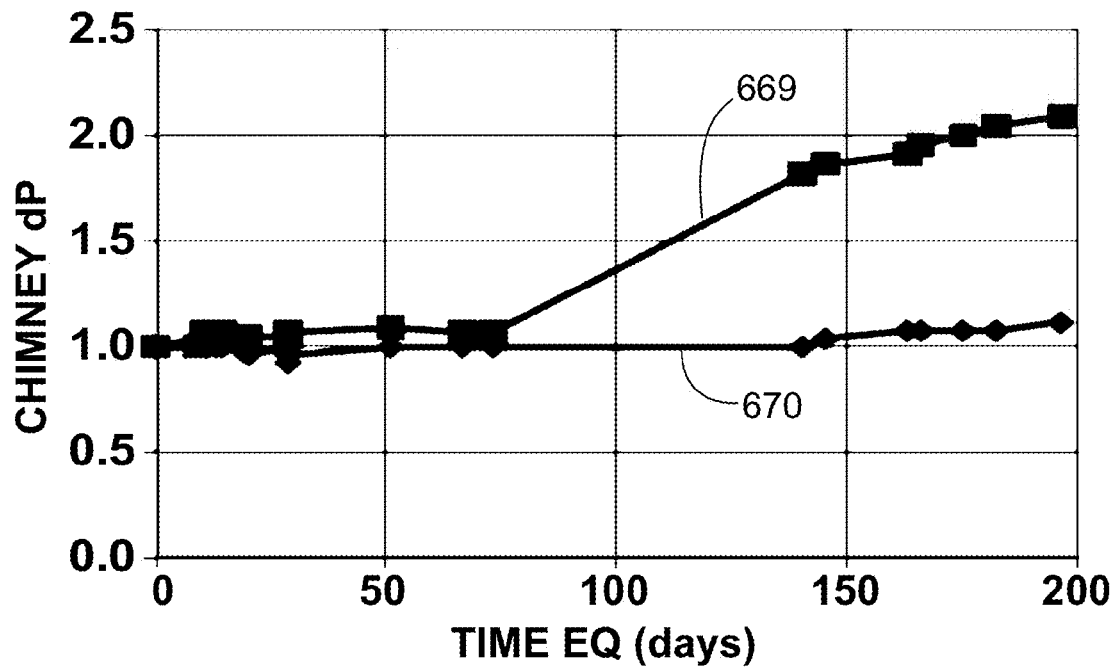
FIGS. 35A and 35B depict chimney pressure drop and collector pressure drop respectively, comparing performance parameters of a skimmer and a particle trap assembly under particle loading with and without pulsed application of ultrasonic acoustic energy.
Figure 35B:
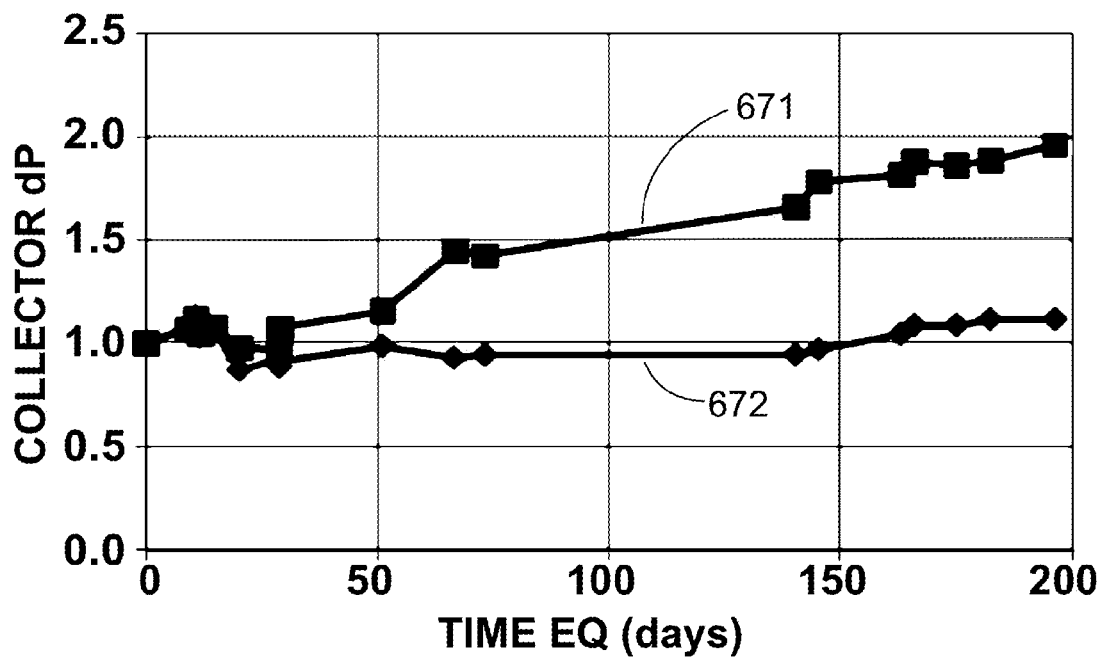

FIGS. 35A and 35B are plots calculating the effect of cleaning during operation and monitoring over a timecourse of two hundred days. The extrapolation is done by overloading the equipment experimentally and then projecting the effect of a more typical loading rate as described in more detail in Example 4. For the virtual impactor, upper curve 669 is absent sonic cleaning, the lower curve 670 with sonic cleaning. For the particle trap, upper curve 671 is absent acoustic cleaning, lower curve 672 with acoustic cleaning A significant gain in equipment life is achieved by use of intermittent acoustic cleaning, extending to weeks and months.

FIG. 36 is a schematic of a collector module 675 having a particle trap 676 for collecting particles from a gas stream, shown here as a minor flow 677 entering through an intake orifice 678 and having a waste gas stream 679 exiting at an outlet. Particles accumulate in the trap and may be periodically removed using acoustic cleaning powered by electro-acoustic transducer 647. The particle trap of the figure may be used in conjunction with a sensor to detect particle accumulation in the trap or proximate to the trap on inside surfaces and regulate insonation parameters via feedback loop 652. Also shown schematically is a programmable, low energy, transducer LC driving circuit 654 with control circuitry 653 and power supply 655 as described previously.

Figure 37:
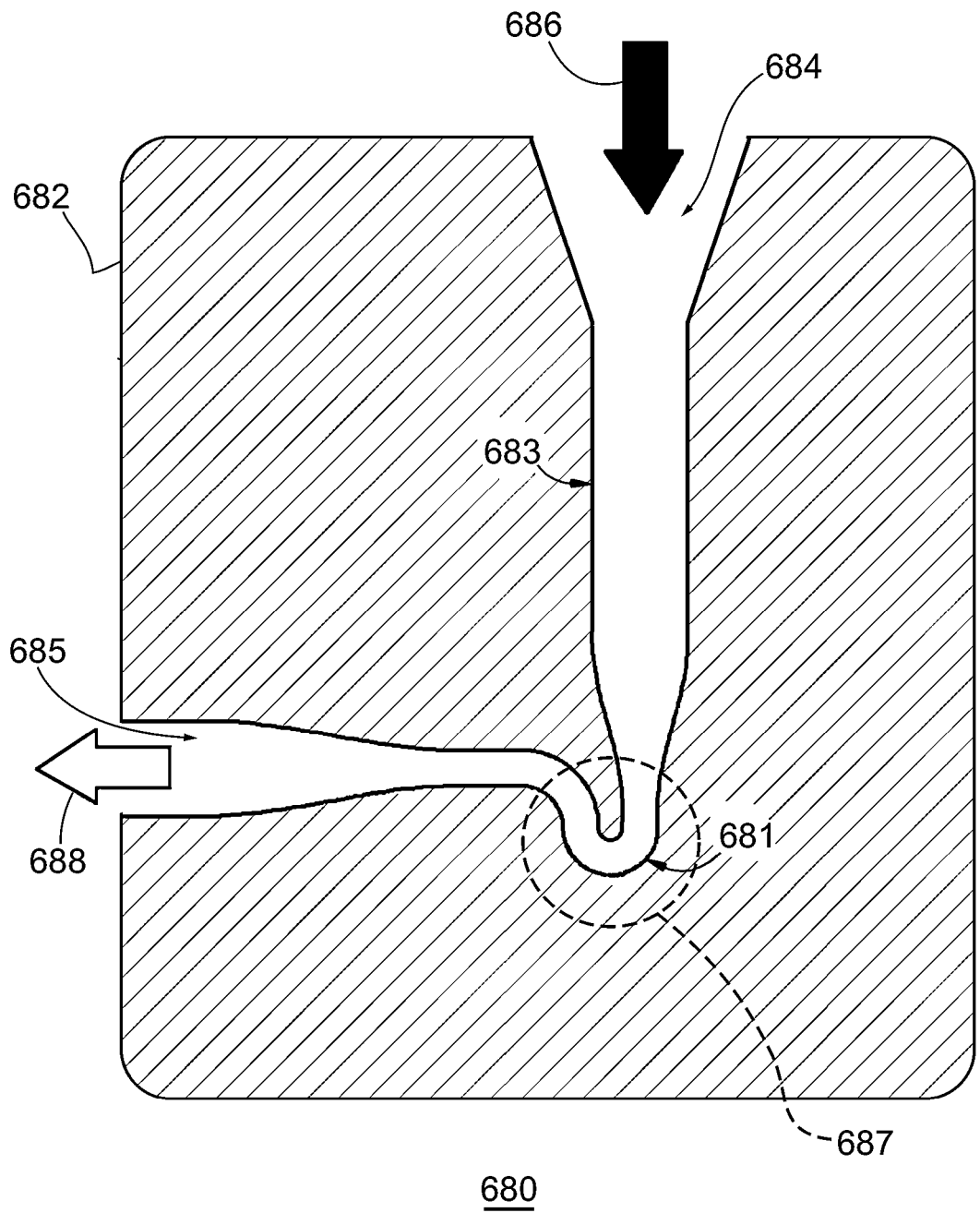
FIG. 37 illustrates a centrifugal impactor ("U-shaped" curved section) with provision for attachment of an acoustic cleaning element (dashed line).

FIG. 37 is a schematic of another embodiment of a collector apparatus 680, where the particle trap 681 is a "centrifugal inertial impactor" and is cleaned when desired by application of acoustic energy from a transducer (dashed circle) coupled to a lateral face of the collector module body. The collector body 682 contains or encloses a collector channel 683 with intake orifice 684 and an outlet arm 685. A gas stream 686 (generally a minor flow) flows through the collector channel in response, for example, to a suction pressure applied to the outlet arm. Disposed in the collector channel is an inertial impactor, formed here by a concavoconvex curvature or bend of the collector channel walls.

As shown here, the electro-acoustic transducer with footprint 687 is coupled to a face of the impactor body and acoustic energy propagates through the solid. Any of a variety of electro-acoustic transducers may be used, including ultrasonic and sonic frequencies.

Optionally, miniature transducers may be embedded in the solid body during fabrication. A driver circuit board is also provided, accompanying the collector module body and including a heatsink for drawing heat away from the power transistor and PZT crystal, for example.

In operation, a gas stream 686 enriched in entrained aerosol particles enters the collector channel 684 at the top of the collector body 682. Aerosol particles not deflected with the gas streamlines in the bending portion of the channel are captured by inelastic impaction on the inertial impactor surface in the particle trap 681. Particles having an inertia greater than a critical limit (the cut size of the impactor) cannot round the bend and are captured by impaction. The aerosol-depleted gas stream 688 exits the collector body at the outlet arm. Under influence of acoustic energy applied with a transducer (dashed circle, 687) contacting the body of the device or applied through an acoustic window in the body, particles in the trap are re-aerosolized in the gas stream to effect acoustic cleaning of the trap as needed.

Figure 38:
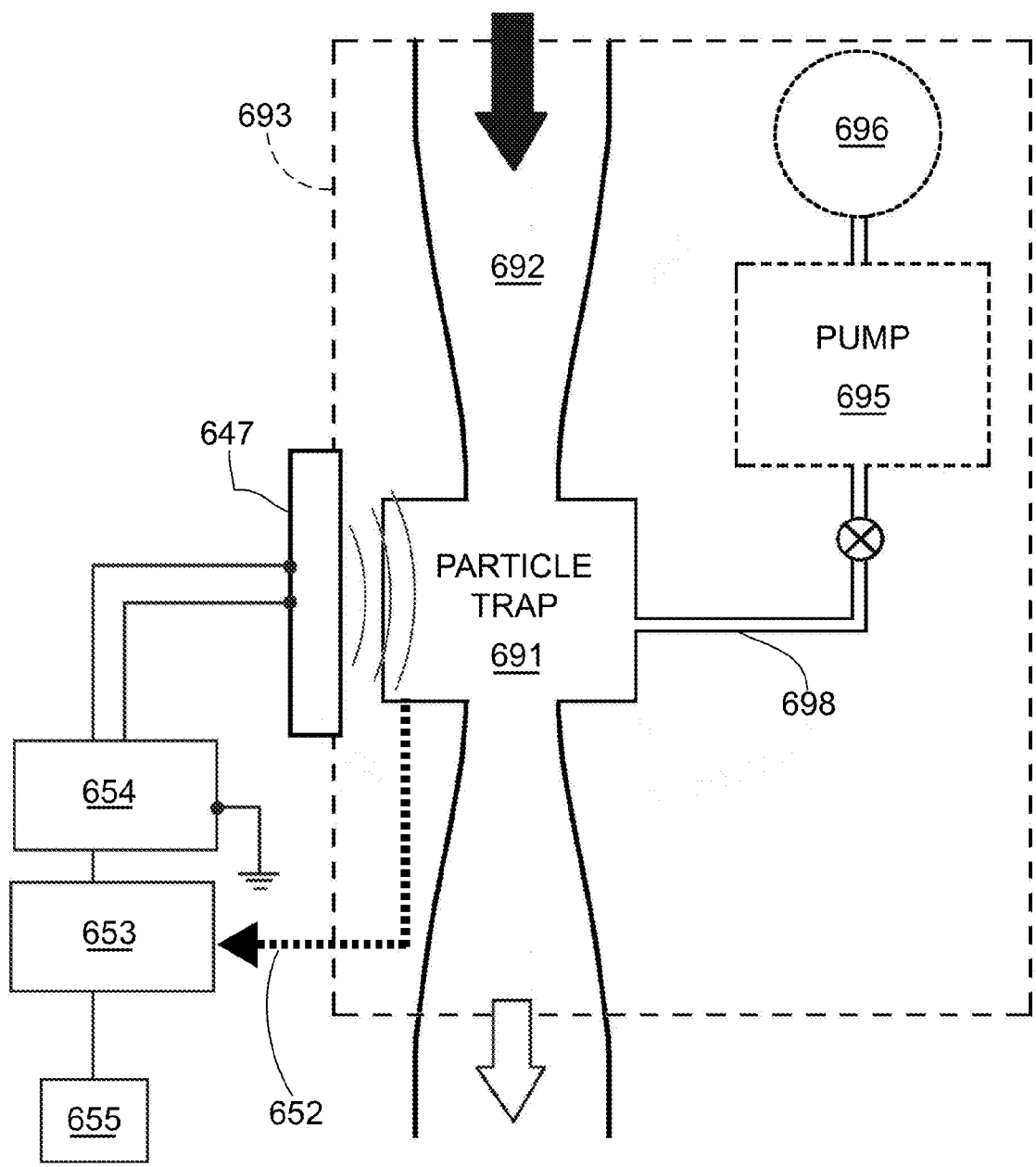
FIG. 38 depicts a contacting electro-acoustic transducer in combination with a liquid hydraulic system to inject a fluid and sonically clean particles from a particle trap.

FIG. 38 is a generic schematic of a collector module 690 with integral wet acoustic cleaning apparatus. Shown in block form are the functional components of a first embodiment of a particle handling apparatus configured for wet acoustic cleaning. A particle trap 691 (or aerosol concentrator) is disposed in a collector channel 692 in a solid body 693, often of metal or plastic. The collector channel, represented here figuratively, consists of a receiving arm with an intake orifice and an outlet arm with outlet orifice. A gas stream containing one or more particles (here a minor flow from a concentrative device) enters the collector channel through the intake orifice and transits the particle handling device. The particle trap may be an inertial impactor, such as a centrifugal inertial impactor, a bluff body impactor, or a filter member, for example. Also included (but not shown), may be an upstream aerosol concentrator such as an aerodynamic lens or skimmer for example. The gas stream, depleted of particles by passage through the particle trap, exits the collector channel at the base of the module through an outlet. Aerosol particles accumulate by fouling on internal surfaces of the apparatus.

When wet cleaning is needed, gas flow is interrupted. The cleaning apparatus of the module comprises a first pump functionality 695 with associated fluid reservoir 696 and an electro-acoustic transducer 647. The components of the apparatus shown by dashed outlines may be mounted within the module 690 or may be mounted externally with fluidic connections. A control circuit 654 (generally under microprocessor control, with non-volatile memory for storing instructions, RAM memory for storing data, and A/D or D/A converters for processing data and instructions) is used to coordinate actions of the various subsystems. Fluid from the fluid reservoir is injected via an injection duct 698, optionally valved, into an internal cavity of the particle trap. The liquid volume contacts the inside surfaces where particle deposits are resident so that when the electro-acoustic transducer 647 is turned on, the wetted surfaces are insonated. The volume of liquid is selected to ensure adequate cleaning. The liquid reservoir may include a level sensor and a mechanism for supplying liquid from an external source.

The liquid sample contains any loosened aerosol particles or constituents. Or the liquid may simply be propelled out through the outlet orifice by a blast of air when the gas stream flow is resumed. Alternatively, the pump functionality may be bidirectional and self-priming, thereby eliminating the need for two pumps. A single, bidirectional pump functionality may be used to both inject a liquid reagent and withdraw the liquid from the particle trap.

Liquid reagents include wash and elution reagents. These reagents are generally aqueous, but may include solvents or co-solvents such as dimethylsulfoxide, N,N-dimethyl-formamide, N-methyl-pyrrolidinone, 2-pyrrolidone, acetone, diethylene glycol monoethyl ether, acetonitrile, acetone, methylethylketone, methyl tert-butyl ether (MBTE), tetrahydrofuran, methanol, propylene carbonate, ethyl acetate, chloroform, butyrolactone, and so forth. Also useful are solvent mixtures and gradients thereof, as have been described by DL Williams and others. The co-solvent is generally miscible with water but if not may be formulated as an emulsion or microemulsion or used without water. Surfactants and wetting agents as are generally known in the art are also suitable for formulation in a liquid wash or resuspension reagent. Such surfactants may include Tween 20, Brij-72, Triton X100, Pluronic F68 (BASF, Florham Pk, N.J.), n-acyl-glutamate (Amisoft®, Ajinomoto, JP), Envirogem® 360 (Air Products, Allentown Pa.), Eccoterge® AEP-20 (Eastern Color, Providence R.I.), sodium lauryl sulfate, and so forth. A more comprehensive list of surfactants, co-surfactants and wetting agents may be found in McCutcheon's Emulsifiers and Detergents (2008 Edition). Also useful for releasing biological samples are salts and buffers. Analytical pre-processing reagents include for example chaotropic salts or urea, such as described by Boom (U.S. Pat. No. 5,234,809), or alkaline SDS lysis solution containing 200 mM NaOH and 1% SDS, as are known to aid in the lysis of bacterial cells, and also enzymes such as lysozyme, chitinase or mucopolysaccharidases. These reagents serve to release any bioaerosol material. General cleaning agents include oxidizers such as bleach, alkaline bleach and hydrogen peroxide. Wash reagents may also contain or generate microbubbles to assist in cleaning using where cavitational excitation of the microbubbles is induced by application of ultrasound.

Figure 39:
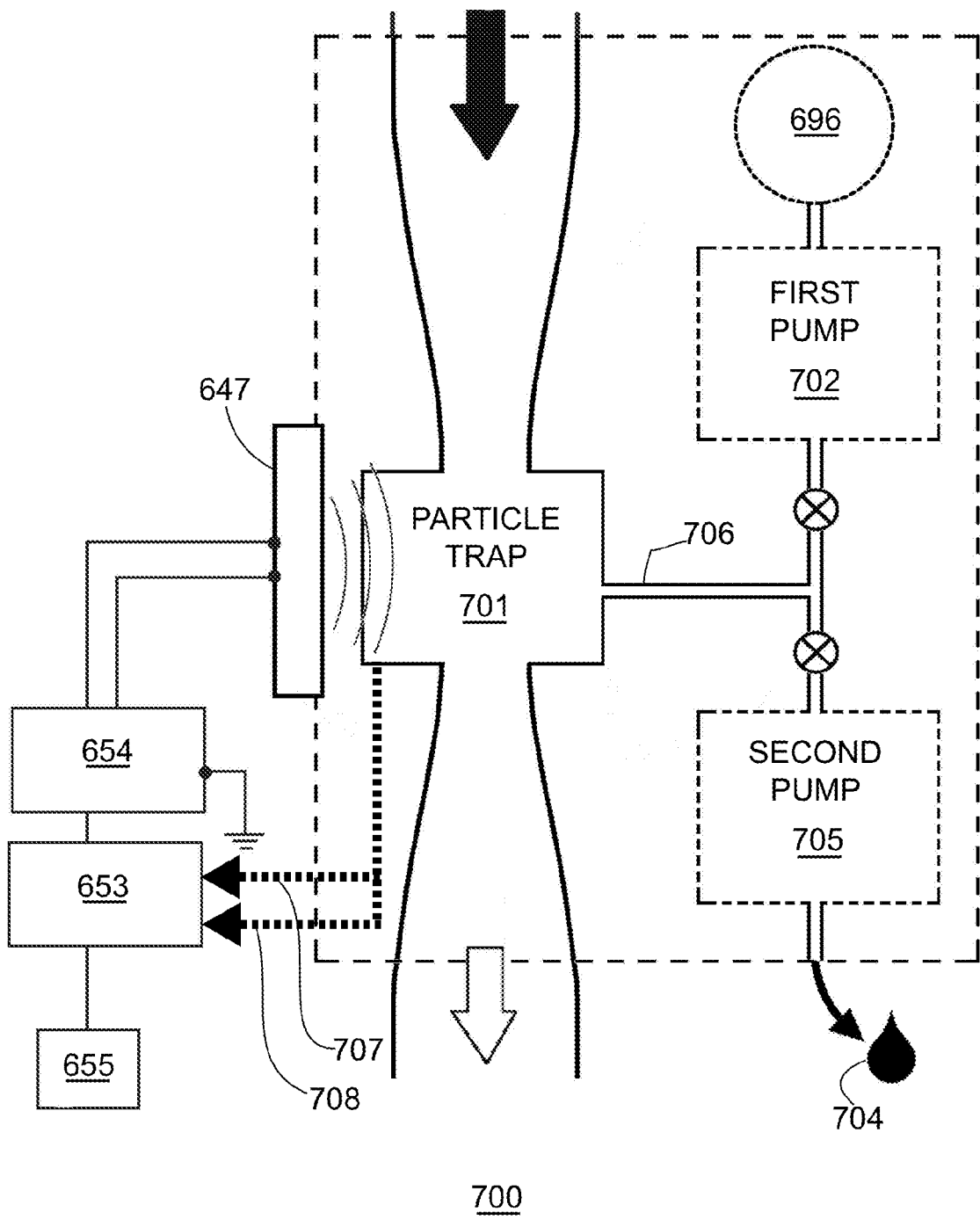
FIG. 39 depicts a contacting electro-acoustic transducer in combination with a hydraulic sampling system for liquid injection and sample recovery to acoustically clean particles from particle trap and to obtain liquid samples for analysis.
Figure 40:
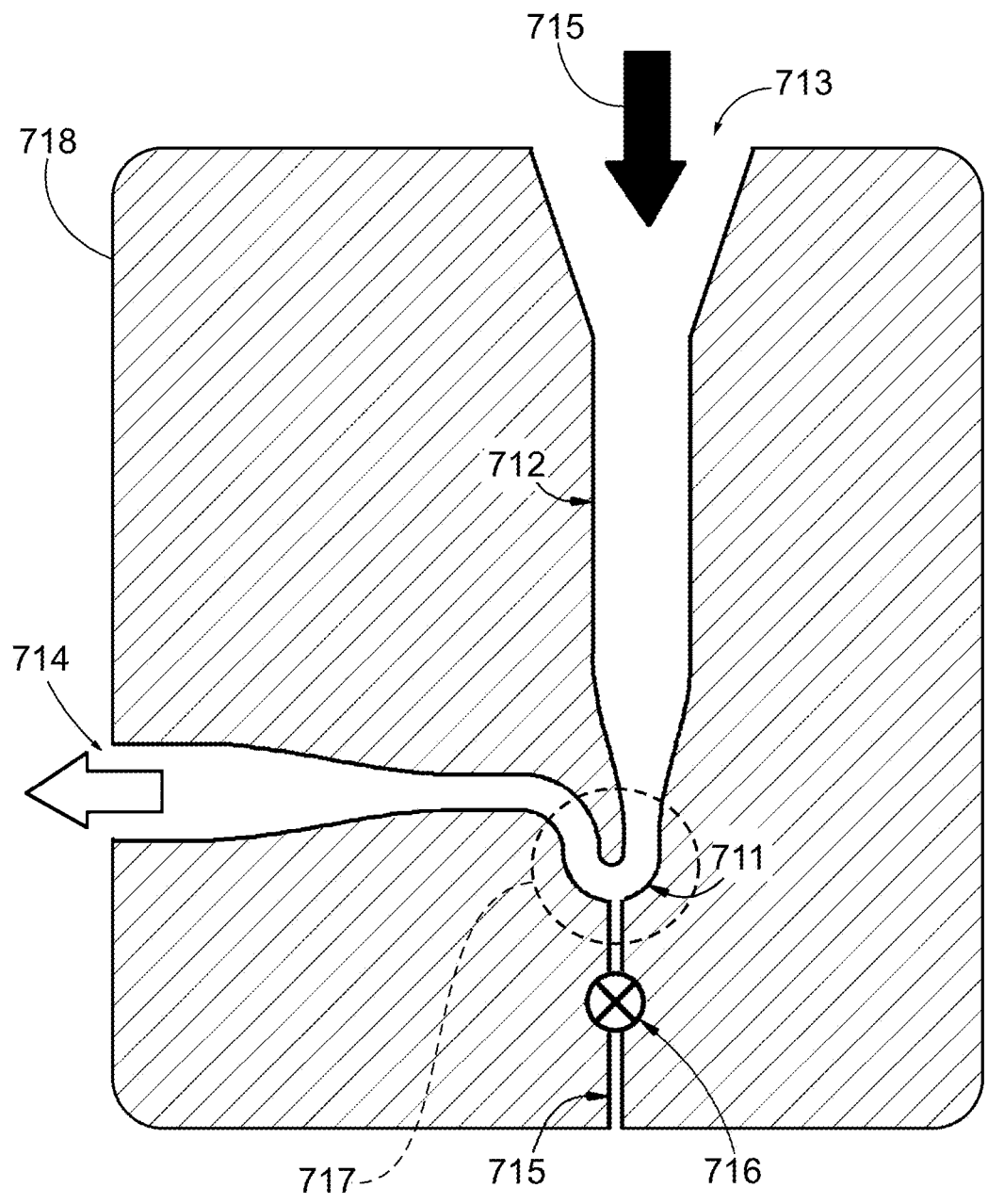
FIG. 40 depicts a combination of an electro-acoustic transducer with a simplified liquid injection system for wet acoustic cleaning of a particle trap.
Figure 41A:
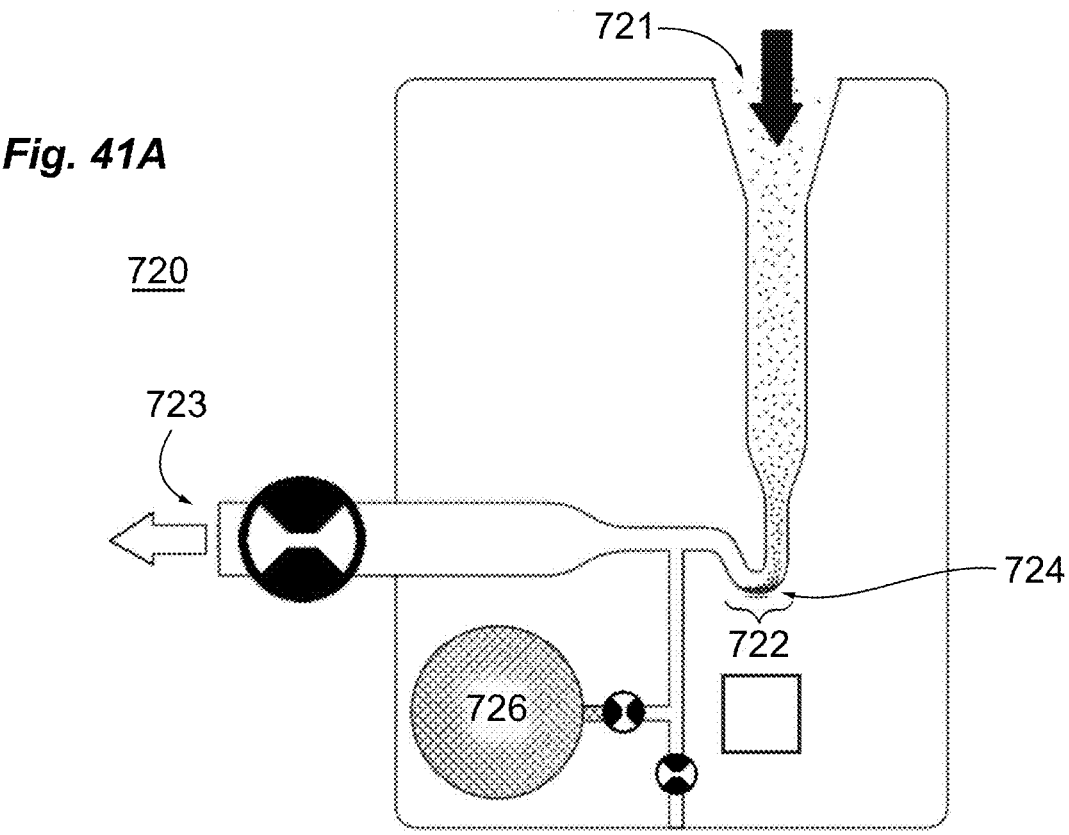
FIGS. 41A through 41D depict schematically a cyclical method for cleaning a particle trap and obtaining a sample of the particle concentrate.
Figure 41B:
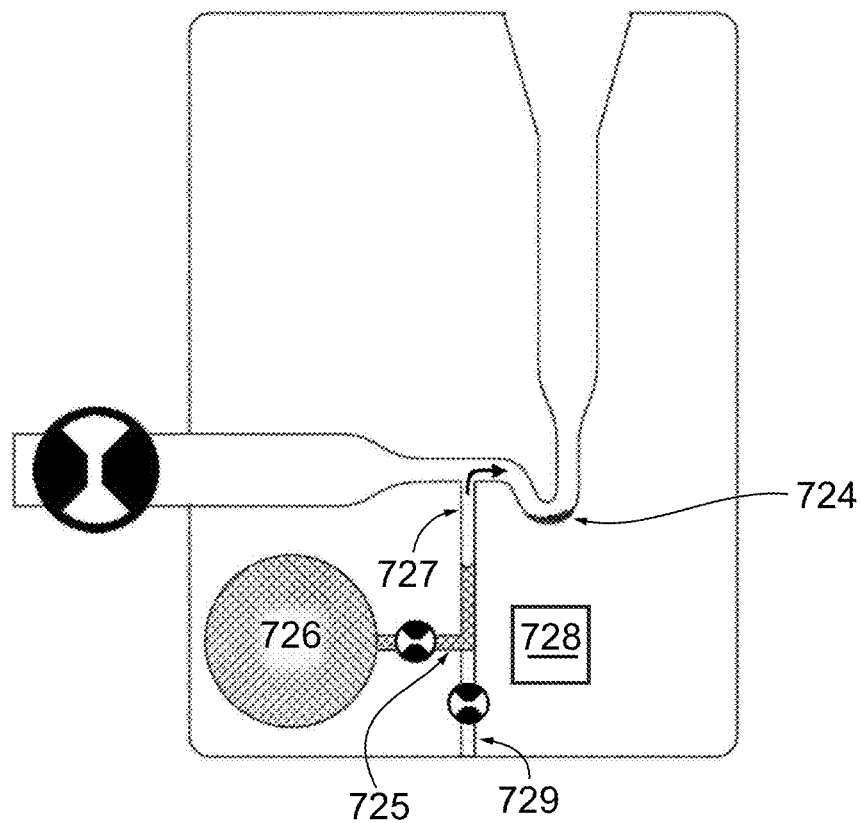
Figure 41C:
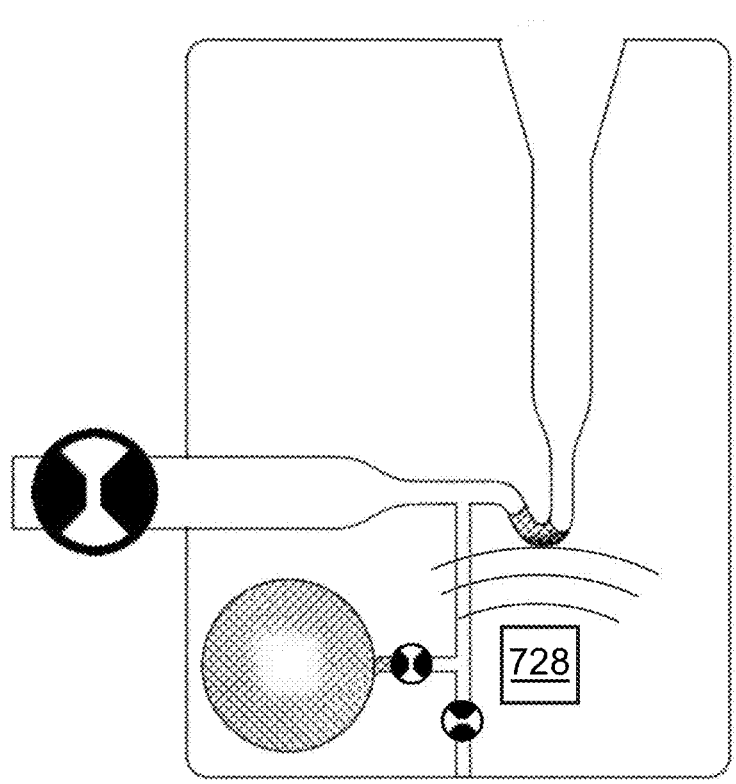
Figure 41D:
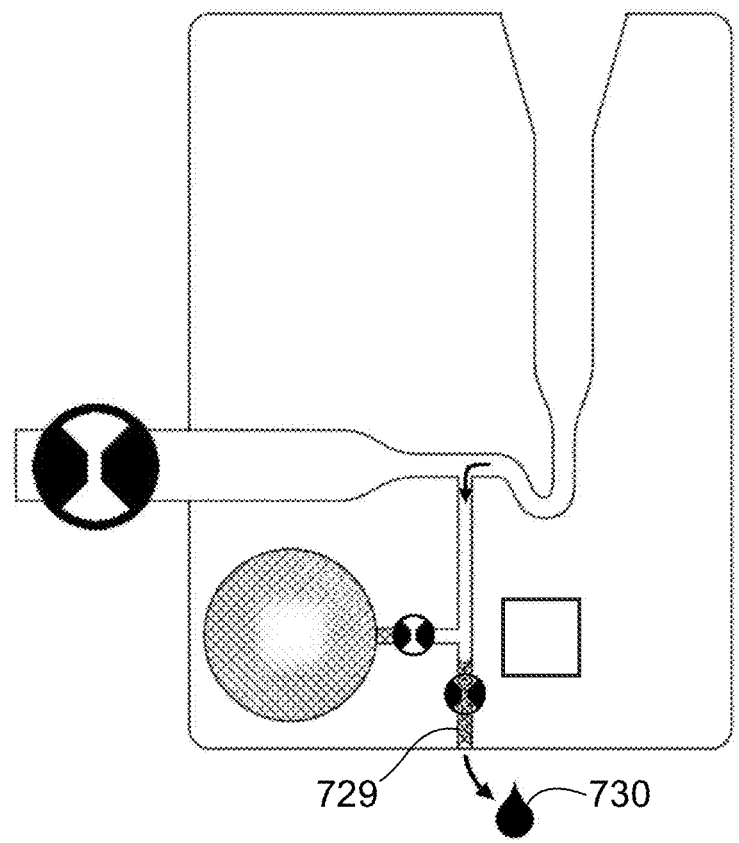

As shown in FIG. 39, a wet cleaning apparatus may also function as a wet sampling apparatus 700. After interrupting the stream of gas flow through a particle trap 701, and then by injecting a volume of liquid into inner works of the trap using a first pump 702, for example, and by applying acoustic energy using an ultrasonic transducer 647, for example, a concentrated particle suspension is obtained. Particles are solubilized in the liquid volume by insonation. The liquid sample 704 of the particle concentrate may then be withdrawn from the trap using a second pump functionality 705. Samples obtained in this way can be analyzed in situ or conveyed to a downstream analytical workstation for further study, or transported to a remote location for analysis or archiving. These pumps and ducting are an example of a hydraulic sampling subsystem.

Suspending the material in a liquid wash solution serves the dual purposes of facilitating the cleaning of the trap and, happily, forming a liquid:particle concentrate 704 that is more readily sampled or conveyed downstream for analysis or archiving. The apparatus thus serves as an air-to-liquid particle concentrator configured for sampling accumulated particle mass in small volumes of liquid.

Optionally, a single pump could perform both liquid injection and withdrawal functions if it is self-priming and capable of impelling bidirectional flow. Or the two systems may be entirely isolated, so that separate microchannels are used for injecting the wash liquid and for collecting a liquid sample. As shown here, a shared injection channel 706 is used for obtaining the liquid sample. The shared channel is valvedly branched to effect this dual function. Various combinations are readily apparent to one skilled in the art.

Activation of a wet sampling cycle can be directed by a signal from a sensor which monitors the gas flow characteristics of the collector, or by direct assay of solid particle deposit residues in the particle trap, as by spectrophotometric analysis, fluorometric analysis, or radiometry. Multiple signals may be processed (707,708). Multiple transducers may also be used, as indicated in FIGS. 31B and 33, for example. Following successful sample acquisition, the particle trap is then thoroughly cleaned and returned to service.

FIG. 39 also illustrates a method for cleaning a particle accretion surface in an internal channel of an aerosol collection apparatus 700, which comprises a) in dry cleaning mode, at regular intervals insonating said particle accretion surface without liquid injection while flowing a gas stream through said internal channel and continuously over said particle accretion surface; b) in wet cleaning mode, in response to a change in a first signal 707, insonating said particle accretion surface after stopping said gas flow and injecting a liquid; and c) in wet sampling mode, in response to a second signal 708, insonating said particle accretion surface after stopping said gas flow and injecting a liquid thereon, then withdrawing a liquid sample 704 of said insonated liquid volume. The first and second signals may be monitored, and steps b and c (above) repeated in response to changes in the first or second signals. The method may also include a step for ultrasonically interrogating the flowing gas stream to sense a change in a flow rate, a flow velocity, or a backpressure, and outputting a sonometric signal indicative of any change, so that insonation of the particle accretion surface is controlled according to feedback from the ultrasonic transducer (such as time of flight measurement used to measure flow velocity). Other signals may also be used (such as backpressure as shown in FIG. 34) to monitor fouling on particle accretion surfaces of aerosol monitoring, concentration, and collection equipment.

FIG. 40 is a schematic of another embodiment of a collector apparatus 710 useful in the method of the invention, where the particle trap 711 is a "centrifugal inertial impactor" (with characteristic inertial bend or loop forming the "trap"). The trap may be an elongate slit or may be tubular or round in cross-section. These particle traps are difficult to clean because the critical dimension of the inside channel is necessarily narrow to maintain velocity of the gas stream in the bending section. When dry acoustic cleaning is not successful, use of wet acoustic cleaning may be needed. While this requires that the gas flow be interrupted or diverted, an advantage of an "auxiliary" liquid cleaning system is that concentrated liquid samples of the accumulated particles can be collected for downstream analysis. Dry cleaning mode can be used to remove particulate deposits that are not of interest; wet cleaning mode may be used to collect particulate deposits wanted for further analysis.

The collector body contains or encloses a collector channel 712 having an intake end 713 and an outlet end 714. A particle-enriched gas stream 715 flows through the collector channel in response, for example, to a suction pressure applied to the outlet arm 714. Disposed in the collector channel is a centrifugal inertial impactor 711 with a particle accretion surface (formed here by a concavoconvex "trap-like" curvature of the collector channel walls).

As shown, an injection duct 715 joins the collector channel at a "tee" in the particle trap. It may be preferable to locate the tee downstream from or upstream of the impactor surface. However, the tee is generally proximate to the inertial impactor surface. The impactor surface is a particle accretion surface. To simplify valving, the injection duct shown here is a common duct used for both injection and removal of the liquid from the trap. The valve 716 is opened during injection and cleaning (or sampling) and is otherwise closed. A volume of fluid may be injected into the particle trap through the injection duct and withdrawn after insonation.

An electro-acoustic transducer (717, dashed circle) contacted with the body 718 is used to apply acoustic energy to the wetted trap. A variety of electro-acoustic transducer configurations are effective. If desired, a liquid sample with particle concentrate can then be withdrawn from the trap through the sample port 715. Otherwise the wash liquid is exhausted to waste or can be ejected by restoring gas flow through the outlet. When wash liquid will be discarded, larger volumes may be used, such as a volume sufficient to fill the internal volume of a particle concentrator and particle trap. Insonation is generally directed at particle accretion surfaces but may be directed more diffusely by the acoustic coupling action of the liquid.

A particle trap with acoustically-assisted liquid sampling is realized in the embodiment illustrated schematically in FIG. 41. Using serial volumes of liquid, cleaning can also be performed with this apparatus. In operation, a gas stream with entrained aerosol particles enters the intake orifice 721 of the collector channel or duct at the top of the collector body in response to a downstream vacuum applied at the outlet orifice (FIG. 41A). Aerosol particles not deflected with the gas streamlines in the bending portion of the trap 722 are captured by inertial impaction on the particle accretion surface. The aerosol-depleted gas stream exits the collector body through the outlet arm 723 and captured particles 724 accumulate in the trap. As shown in FIG. 41B, the gas stream is turned off following capture by closing a valve at the outlet orifice. A liquid volume 725 is then injected through a tee into the trap from a fluid reservoir 726 in communication with the trap via an injection duct 727. In FIG. 41C, the liquid is contacted with the captured particles and subjected to acoustic energy delivered via a transducer 728 operatively coupled to the collector body. Impacted particles are dislodged from the particle accretion surfaces of the trap and suspended in the liquid. The liquid is then removed via a sampling arm 729 of the injection duct and conveyed downstream as a concentrated liquid sample 730 of the captured particles or discarded as waste, leaving the particle trap clean and ready for another cycle (FIG. 41D).

The resultant liquid sample, containing the concentrated solution or suspension of the aerosol particles, is conveyed to an external fluidic circuit or other analytical means via a sample port. Alternatively, the highly concentrated sample liquid can instead advantageously be analyzed in situ in the particle trap with a suitable analytical apparatus, such as spectrometric or electrometric analysis via an optical window in the collector body prior to downstream analysis or archiving of the sample.

The liquid sample and particle concentrate may be analyzed for a physical, chemical or biological property. A variety of analytical means are known in the art, and include without limitation methods of:
1. inducing fluorescence of specific constituents of the liquid sample and detecting emitted fluorescent emissions;
2. measuring optical absorption of the liquid sample at one or more wavelengths;
3. measuring light scattered from the liquid sample in various directions, as by laser scattering;
4. subjecting the liquid sample to at least one spectroscopic measurement technique such as Raman spectroscopy (RS), laser induced breakdown spectroscopy (LIBS), spark-induced breakdown spectroscopy (SIBS), or mass spectroscopy;
5. subjecting the liquid sample to nucleic acid amplification and real-time PCR;
6. subjecting the liquid sample to an immunological assay; or
7. measuring radiation emitted from the liquid sample.

The analysis or analyses is for the purpose of detecting and/or identifying those constituents of interest. In a first instance, using optical means, analysis may be performed by measuring light transmittance, light reflectance, fluorescence, or luminescence of the liquid.

In another instance, using electrical means, the conductance, impedance, or capacitance may be monitored. Affinity impedance spectroscopy may also be applied. In yet other instances, analysis may be performed by detecting an alpha-particle emission, beta-particle emission, or gamma emission, or by detecting a molecular species or fragment thereof in the liquid by an affinity binding technique, an enzymatic reaction, or by electrospray mass spectroscopy, and so forth, without limitation thereto.

Such analytical methods may benefit with improved sensitivity and limits of detection by concentration of the particle sample in a small volume of liquid, where a particle population is first stripped acoustically from the particle trap and concentrated in a liquid sample.

In one embodiment, the electro-acoustic transducer is operatively coupled to the particle trap by the solid body and the electro-acoustic transducer is a piezoelectric, magnetostrictive, or electrostatic transducer. In another embodiment, the electro-acoustic transducer is operatively coupled to the surface through an acoustic window overlying the surface and the electro-acoustic transducer is a gas-coupled electrostatic air-coupled transducer or capacitive electro-acoustic transducer. In some embodiments, acoustic energy is applied continuously; in others acoustic energy is applied as a pulse or train of pulses having a fractional duty cycle; and in others ultrasound is applied only in response to a signal indicating fouling or blockage.

Figure 42A:
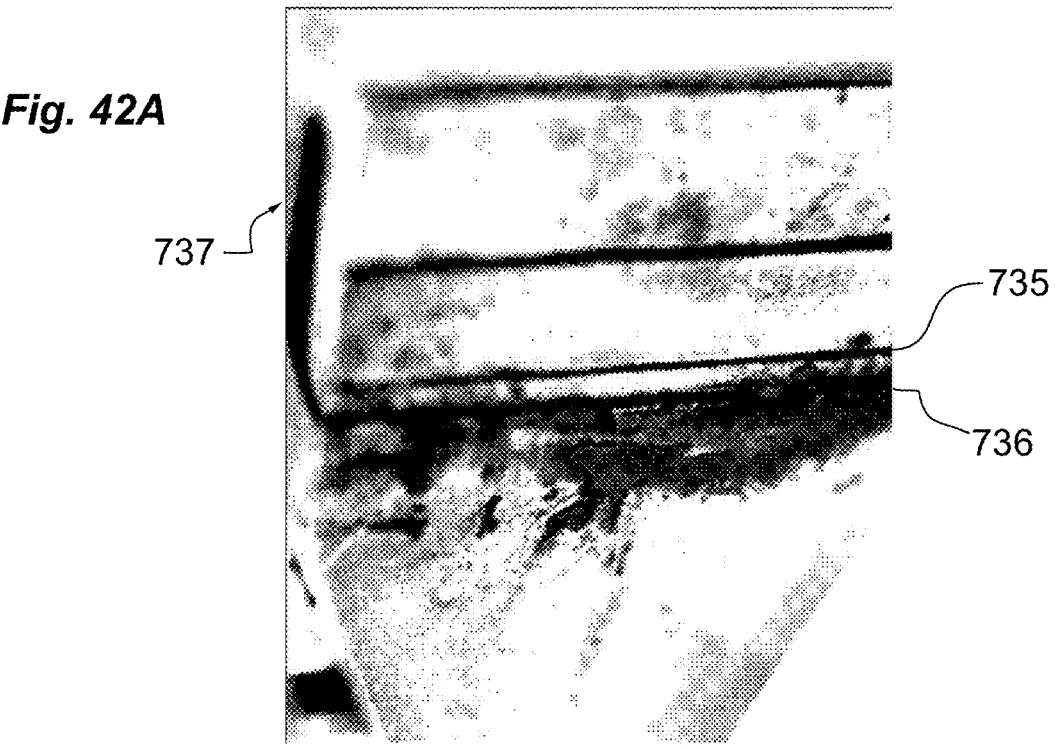
FIGS. 42A and 42B depict first a skimmer mouth that has been fouled by progressive accretion of particle deposits over time and next a corresponding skimmer mouth treated preventatively with periodic application of pulsed ultrasound.
Figure 42B:

FIG. 42A is a representation of a particle concentrator opened for inspection so that the channels of the skimmer are exposed. In this view of the skimmer, the horizontal slit 735 and collector channel 736 that are heavily laden with particles is the entrance to a lateral chimney 737 (analogous to that depicted in FIG. 32), and one half face of the structure is shown. Large numbers of particles (black deposits) have accumulated in the collector channel around the virtual impactor mouth of the skimmer 735, dramatically increasing resistance to flow through the aperture to the chimney and on the collector channel walls. FIG. 42B shows the effect of periodic dry acoustic cleaning for prophylaxis under equivalent operating conditions. Limited particle residuals (ASHRAE dust) are noted on skimmer slit 735 or collector channel face 736 and operational performance is nominal.

Accordingly, the invention is a method for dry cleaning particle deposits from an internal surface of an aerosol monitoring, concentration, or collection apparatus or for preventing accumulation of particle deposits, which comprises steps for:

a) applying acoustic energy to the surface, wherein the acoustic energy is applied from an electro-acoustic transducer operatively coupled thereto;
b) acoustically mobilizing any particle deposits from the surface; and
c) removing the particle deposits in a flowing gas stream.

Steps a)-c) may be repeated if desired to satisfactorily clean the particle accretion surface. In a preferred method, the cleaning cycle is performed "on the fly", where gas flow and operation are not interrupted and the method is applied as needed to prevent of particle buildup, either on a regular schedule or when conditions indicate it is needed.

For cleaning, the surface to be treated may be an internal surface of a particle trap or any internal surface of a gas-to-gas particle concentrator subject to fouling or blockage. With respect to the operation and cleaning of aerosol concentrators, in a preferred method, the invention further includes a step for sensing a flow rate, a flow velocity, or a backpressure with a sensor and outputting a digital or analog signal from the sensor that is used to initiate a cleaning cycle if the signal is consistent with an undesirable level of accumulation of particles or deviates from an acceptable value or range.

The sensor may be an electro-acoustic transducer, where the transducer sonically interrogates the flowing gas stream to sense a flow rate, a flow velocity, or a backpressure, and generates a signal. Other sensors are also useful. Flow velocity for example may be detected by Doppler shift methods. Backpressure may be monitored using suitable pressure sensors, for example air-coupled electro-acoustic transducers where energy output is highly sensitive to gas density, or piezoelectric, microcantilever or diaphragm-type pressure sensors. Alternatively, optical or electrical characterization of the condition of the internal surfaces is used to determine a need for cleaning. Optical sensors include laser scattering detectors, spectrophotometers, and fluorometers. Electrical sensors include circuits for measuring capacitance, resistance or conductance of the inside surface associated with fouling. Sensors may be used in combination to detect an operating condition of the aerosol monitoring, concentration, or collection apparatus and a composition of the accreted particle deposit, if desired.

Dry acoustic treatment may be used to prevent or relieve particle buildup without interruption of gas flow; liquid acoustic cleaning treatment is used to clean more resistant deposits or to sample the accumulated particles in a concentrated liquid sample for further analysis.

Wet cleaning may be applied independently. In another embodiment, the invention is a method for wet cleaning particle deposits from an internal surface of an apparatus using a liquid cycle, which comprises steps for:

a) fluidly contacting a particle accretion surface with a liquid with gas flow stopped;
b) applying acoustic energy to the surface, wherein the acoustic energy is applied from an electro-acoustic transducer operatively coupled thereto;
c) acoustically mobilizing any particle deposits on the surface in the liquid; and
d) removing the liquid and ultrasonically mobilized particle deposits from the particle accretion surface, and then restarting gas flow.

Optionally, the method may include a step for sensing a performance parameter of the aerosol monitoring, concentration, or collection apparatus and triggering the cleaning cycle when said operational parameter deviates from an acceptable value or range.

Advantageously, cleaning can be combined with sampling particle residues by liquid injection with wet acoustic treatment. By injecting a discrete volume of a wash liquid into a particle trap and treating the particle trap with ultrasound, a concentrated suspension or solution of particles or particle constituents is obtained.

EXAMPLES

Example 1

Dry Acoustic Cleaning of an Aerosol Concentrator

An aerosol concentrator with ADL and skimmer of the type shown in co-assigned U.S. Pat. No. 7,875,095 was set up with flowing air and instrumented to monitor backpressure. ASHRAE dust was then introduced into the feed and backpressure was monitored. After a suitable interval, backpressure in the major and minor flow channels had substantially increased. The skimmer assembly was then subjected to acoustic energy using a piezoelectric horn contacted to the body of the skimmer. Backpressure immediately returned to pre-fouling levels. As shown in the table below, backpressure in the major flow channels was seen to rise from 5.5 to 12 inches $H_2O$ with increased narrowing due to accumulation of ASHRAE dust in the channels. Upon application of ultrasound to the body of the assembly, backpressure immediately returned to baseline. Similarly, in the minor flow channel, backpressure rose from 0.3 to 1.8 inches $H_2O$, but returned to 0.3 inches $H_2O$ upon application of ultrasound to the device. Inspection showed that the internal workings of the concentrator were essentially free of particle deposits following this treatment.

| State | Backpressure, Major Flow Channels (inches $H_2O$) | Backpressure, Minor Flow Channel (inches $H_2O$) |
|---|---|---|
| Initial | 5.5 | 0.3 |
| Fouled | 12 | 1.8 |
| Cleaned | 5.5 | 0.3 |

Example 2

Prophylaxis

In a second example, prophylactic treatment was demonstrated. Using the setup of Example 1, ASHRAE dust was again introduced into an aerosol concentrator. A flow split of 40:1 was used; with 10 Lpm flow rate in the chimneys and 0.25 Lpm in the collector channel. Rather than permit fouling to occur, ultrasound (33 KHz, 50 W) was applied for 1 second at 2 minute intervals. Backpressure was again monitored.

After 30 minutes, no increase in backpressure was noted in any of the channels of the device. Contrastingly, backpressure had noticeably increased under control conditions without ultrasonic prophylaxis of fouling. Visual inspection confirmed that particle deposits were prevented by periodic ultrasonic treatments.

| Experimental | Backpressure, Major Flow Channels (inches $H_2O$) | Backpressure, Minor Flow Channel (inches $H_2O$) |
|---|---|---|
| Intermittent US Treatment over 30 min | 3 | 0 |
| Negative Control | 3 | 0.3 |

The reduced duty cycle (1 sec ON at 2 min intervals) reduced energy consumed in the ultrasonic treatment to less than a Watt. Low power consumption is desirable for portable applications, for example, such as where power is battery supplied or supplied by a solar cell.

Rechargeable AA-sized batteries based on lithium ion chemistry are of use. These batteries are rated at 3.6 volts and are incompatible with most AA-based devices. AA lithium batteries have a relatively low internal resistance that effectively provides very high current if shorted. RCR-V3 batteries having a nominal voltage of 3.7 V are capable of performing 3.6 Watt-hours of work (computed as 1200 mAh*3V). AA batteries yielding 2.4 Watt-hours are also suitable. For more extended application at higher loads, combinations of 12 VDC batteries may be configured in a portable battery case and will operate pulsed electro-acoustic transducers for days or even months without recharging or replacement.

Example 3

Timecourse for Fouling Under Heavy Loading

Using the setup described in the examples above, the data of FIG. 34 was obtained by monitoring backpressure over a thirty minute interval. Backpressure is reported as percent over baseline. Backpressure in the chimney of the untreated channel continued after ten minutes but increases are not shown because the pressure gauge had reached its maximum reading.

Example 4

Longterm Equipment Operation

A surprising and unexpected finding from extrapolations of these results (FIG. 35) is that, by the inventive application of ultrasound at periodic intervals, an aerosol concentrator of this construction can be operated for months without maintenance. Periodic pulses of ultrasound applied to the concentrator body were shown not to interfere with particle collection and analysis.

Example 5

Wet Acoustic Cleaning

Wet ultrasound was used for cleaning the complex geometry of a tubular inertial particle trap having small internal volume structures using acoustic energy. A small (1/16") stainless steel tube centrifugal aerosol collector (as described in U.S. Prov. Pat. Appl. No. 61/026,376 and US Pat. Appl. Doc. No. 2010/0186524, which are coassigned) was placed in a chamber filled with aerosolized fluorescent polystyrene spheres. Aerosol-laden air was aspirated through the collector under conditions selected to impact particles in the particle trap.

Following particle loading, the particle trap was then injected with a volume of liquid (in this case water). Due to the small internal volume of the collector, a discrete volume of only 50 ul liquid volume was needed. A piezoelectric electro-acoustic transducer was then pressed again the metal tube and operated for 5 seconds. A second treatment was then performed. The sample liquid was removed from the collector and analyzed by measuring fluorescence emission from the sample. The experiment showed that 90% of the particles were removed in the first treatment and 10% in the second treatment.

Incorporation by Reference

All of the US patents, US patent applications, US patent application publications, foreign patents, foreign patent applications and non-patent publications referred to in this specification and/or listed in any Information Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the specifics of the disclosure.

While the invention has been described with preferred embodiments and illustrations, it is to be understood that variations and modifications may be resorted to as will be apparent to those skilled in the art. Such variations and modifications are to be considered within the purview and the scope of the claims appended hereto.

We claim:

1. An apparatus for collecting aerosol particles from a gas stream, said apparatus comprising a) a collector channel comprising an intake, an outlet, and a centrifugal particle trap fluidly connected between said intake and said outlet, wherein said centrifugal particle trap is a curved segment of said collector channel, said curved segment curving in the range of 120 to 360 degrees of arc and having a characteristic dimension defined as a minimum dimension of height or internal diameter in the range of 100 to 1500 micrometers, a maximal bending radius of in the range of between 0.5 to 3.0 times the characteristic dimension, and a trap volume defined by a concavedly curved wall of said channel on a first side of said volume, a convexedly curved wall of said channel on an opposite side of said volume, and lateral side walls, such that the height and width of said curved segment is essentially constant therethrough;

b) a means for starting and stopping the flow of the gas stream through said particle trap;

c) a means for injecting a first liquid into said particle trap; wherein said apparatus is configured to have:

i) a first operating state defined by starting said gas stream flowing into said intake and out said outlet, said gas stream flowing at a subsonic velocity and having streamlines, wherein said streamlines bend in said curved segment so that particles cross the streamlines according to their inertia and come to rest on an impactor surface of said concavedly curved wall, thereby exhausting said gas stream from said outlet as a particle-depleted exhaust and trapping impacted particles in said particle trap as a trapped particle sample; and, ii) a second operating state defined by stopping said gas stream and injecting said first liquid as a discrete liquid volume into said particle trap, wherein said discrete liquid volume is constrained by said walls and contactingly microelutes the trapped particle sample from said impactor surface as a liquid particle concentrate.

2. The apparatus of claim 1, wherein said ranges are defined to configure said streamlines so as to capture more than 50% of the sub-micron particles having an aerodynamic diameter greater than 0.7 microns in said gas stream, wherein said gas stream is flowing at 0.05 to 10 L/min.

3. The apparatus of claim 1, comprising a particle trap having a critical dimension in the range of 200 to 750 micrometers, wherein said streamlines are configured to capture more than 50% of the sub-micron particles having an aerodynamic diameter greater than 0.7 microns in said gas stream, wherein said gas stream is flowing at 0.5 to 1 L/min.

4. The apparatus of claim 1, wherein said discrete liquid volume is configured for forming a fluid plug when injected into said particle trap, said fluid plug having dimensions for occluding said collector channel.

5. The apparatus of claim 1, wherein said gas stream is a minor flow received from an aerosol concentrator fluidly connected to said intake.

6. The apparatus of claim 4, wherein said discrete liquid volume for forming said liquid particle concentrate is less than 10 microliters.

7. The apparatus of claim 4, wherein said discrete liquid volume for forming said liquid particle concentrate is less than 1 microliter.

8. The apparatus of claim 1, wherein said particle trap comprises an acoustic window and an optical window, and wherein said acoustic window is configured to enable insonation of said liquid particle concentrate and said optical window is configured to enable spectroscopic monitoring of said liquid particle concentrate.

9. The apparatus of claim 1, wherein said particle trap comprises an optical window configured to enable spectroscopic monitoring of said liquid particle concentrate, and said first liquid comprises a detection reagent for generating an optical signal in the presence of a target analyte.

10. The apparatus of claim 1, wherein said first liquid comprises an elution reagent.

11. The apparatus of claim 10, wherein said elution reagent contains water, nonaqueous solvent, or a mixture thereof.

12. The apparatus of claim 10, wherein said elution reagent is a mixture of acetonitrile and water.

13. The apparatus of claim 10, wherein said elution reagent is an emulsion or a microemulsion.

14. The apparatus of claim 1, further comprising a means for injecting a second liquid into said particle trap.

15. The apparatus of claim 14, wherein said second liquid comprises an analytical pre-processing reagent.

16. The apparatus of claim 15, wherein said analytical pre-processing reagent is a chaeotropic salt, urea, an alkaline SDS lysis reagent, a lysozyme reagent, a chitinase reagent, or a mucopolysaccharidase reagent.

17. The apparatus of claim 14, wherein said second liquid comprises a detection reagent.

18. The apparatus of claim 17, wherein said detection reagent is an antibody reagent, a nucleic acid probe reagent, a nucleic acid intercalating reagent, a chromogenic reagent, a stain reagent, a catalase detection reagent, or a dehydrogenase detection reagent.

19. The apparatus of claim 17, wherein said detection reagent is tetrazolium blue.

20. The apparatus of claim 1, wherein said impactor surface is coated with a sacrificial layer.

21. The apparatus of claim 20, wherein said sacrificial layer comprises a lysis reagent, an analytical pre-processing reagent, or a detection reagent.

22. The apparatus of claim 20, wherein said sacrificial layer is a glass.

23. The apparatus of claim 22, wherein said glass is composed of trehalose, glycerol, and polyvinylpyrrolidinone.

24. The apparatus of claim 1, wherein said particle trap is enclosed in a plastic body, said plastic body enclosing a microfluidic assay circuit, and further comprising a means for conveying said liquid particle concentrate from said particle trap to said micro fluidic assay circuit.

25. The apparatus of claim 24, wherein said microfluidic analysis circuit comprises a nucleic acid extraction circuit.

26. The apparatus of claim 24, wherein said microfluidic circuit comprises a nucleic acid analysis and detection circuit.

27. The apparatus of claim 1, further comprising a means for conveying said liquid particle concentrate from said particle trap for downstream analysis by mass spectrometry.

\* \* \* \* \*